(12) United States Patent
Wehner et al.

(10) Patent No.: US 6,962,937 B2
(45) Date of Patent: Nov. 8, 2005

(54) IMIDAZOLIDINE DERIVATIVES, THEIR PREPARATION AND THEIR USE

(75) Inventors: Volkmar Wehner, Sandberg (DE); Stefanie Flohr, Eppstein (DE); Horst Blum, Frankfurt (DE); Hartmut Rütten, Idstein (DE); Hans Ulrich Stilz, Frankfurt (DE)

(73) Assignee: Aventis Pharma Deutschland GmbH (DE)

( * ) Notice: Subject to any disclaimer, the term of this patent is extended or adjusted under 35 U.S.C. 154(b) by 0 days.

(21) Appl. No.: 10/208,182

(22) Filed: Jul. 31, 2002

(65) Prior Publication Data

US 2003/0109497 A1 Jun. 12, 2003

(30) Foreign Application Priority Data

Aug. 1, 2001 (DE) .......................................... 101 37 595

(51) Int. Cl.⁷ .................. A61K 31/4166; C07D 233/02
(52) U.S. Cl. .................................... 514/398; 548/319.5
(58) Field of Search ...................... 548/319.5; 514/398, 514/392

(56) References Cited

U.S. PATENT DOCUMENTS

| | | |
|---|---|---|
| 5,389,614 A | 2/1995 | Koenig et al. |
| 5,397,796 A | 3/1995 | Zoller et al. |
| 5,424,293 A | 6/1995 | Zoller et al. |
| 5,554,594 A | 9/1996 | Zoller et al. |
| 5,658,935 A | 8/1997 | Klingler et al. |
| 5,686,421 A | 11/1997 | Koenig et al. |
| 5,939,556 A | 8/1999 | Zoller et al. |
| 5,981,492 A | 11/1999 | Zoller et al. |
| 5,998,447 A | 12/1999 | Stilz et al. |
| 6,034,238 A | 3/2000 | Wehner et al. |
| 6,218,415 B1 | 4/2001 | Wehner et al. |
| 6,331,552 B1 | 12/2001 | Wehner et al. |
| 6,423,712 B1 | 7/2002 | Wehner et al. |

FOREIGN PATENT DOCUMENTS

| | | |
|---|---|---|
| DE | 235 866 | 5/1986 |
| DE | DD 235 866 | 5/1986 |
| EP | 0 796 855 | 3/1997 |
| EP | 0 842 943 | 11/1997 |
| EP | 0 842 944 | 11/1997 |
| EP | 0 842 945 | 11/1997 |
| EP | 0 903 353 | 9/1998 |
| EP | 0 905 139 | 9/1998 |
| EP | 0 918 059 | 11/1998 |
| WO | WO 93/13798 | 7/1993 |
| WO | WO 93/15764 | 8/1993 |
| WO | WO 93/18057 | 9/1993 |
| WO | WO 94/15958 | 7/1994 |
| WO | WO 94/16094 | 7/1994 |
| WO | WO 94/17828 | 8/1994 |
| WO | WO 95/14008 | 5/1995 |
| WO | WO 95/15973 | 6/1995 |
| WO | WO 95/19790 | 7/1995 |
| WO | WO 96/00581 | 1/1996 |
| WO | WO 96/06108 | 2/1996 |
| WO | WO 96/20216 | 7/1996 |
| WO | WO 96/22966 | 8/1996 |
| WO | WO 96/33976 | 10/1996 |
| WO | WO 97/03094 | 1/1997 |
| WO | WO 98/04247 | 2/1998 |
| WO | WO 98/04913 | 2/1998 |
| WO | WO 98/42656 | 10/1998 |
| WO | WO 99/23063 | 5/1999 |
| WO | WO 99/24398 | 5/1999 |
| WO | WO 99/54321 | 10/1999 |
| WO | WO 99/60015 | 11/1999 |
| WO | WO 00/00477 | 1/2000 |
| WO | WO 00/02903 | 1/2000 |
| WO | WO 00/69831 | 11/2000 |

OTHER PUBLICATIONS

Abraham, William M. et al., "$\alpha_4$– Integrins Mediate Antigen–induced Late Bronchial Responses and Prolonged Airway Hyperresponsiveness in Sheep", *J. Clin. Invest.*, vol. 93, Feb. 1994, 776–787, The American Society for Clinical Investigation, Inc., Ann Arbor MI USA.

(Continued)

*Primary Examiner*—Golam M M Shameem
(74) *Attorney, Agent, or Firm*—Heller Ehrman LLP

(57) ABSTRACT

The present invention relates to novel imidazolidine derivatives of the formula I,

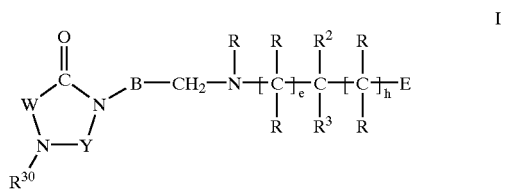

in which B, E, W, Y, R, $R^2$, $R^3$, $R^{30}$, e and h have the meanings given herein. The compounds of the formula I are valuable pharmaceutically active compounds which are suitable, for example, for treating inflammatory diseases, for example, rheumatoid arthritis, or allergic diseases. The compounds of the formula I are inhibitors of the adhesion and migration of leukocytes and/or antagonists of the adhesion receptor VLA-4, which belongs to the integrin group. They are generally suitable for treating diseases which are caused by, or associated with, an undesirable degree of leukocyte adhesion and/or leukocyte migration or in which cell-cell or cell-matrix interactions, which are based on the interactions of VLA-4 receptors with their ligands, play a role. The invention furthermore relates to processes for preparing the compounds of the formula I, to their use and to pharmaceutical preparations which comprise compounds of the formula I.

5 Claims, No Drawings

OTHER PUBLICATIONS

Adams, David H. et al., "Experimental Graft Arteriosclerosis,", *Transplantation*, vol. 56, 794–799, No. 4, Oct., 1993, Lippincott Williams & Wilkins, Baltimore MD USA.

Albelda, Steven M. et al., "Molecular and Cellular Properties of PECAM–1 (endoCAM/CD31): A Novel Vascular Cell–Cell Adhesion Molecule", *The Journal of Cell Biology*, vol. 114, No. 5, Sep. 1991, 1059–1068, The Rockefeller University Press, New York NY USA.

Barbadillo, Carmen et al., "Anti–integrin immunotherapy in rheumatoid arthtiris: protective effect of anti–α4 antibody in adjuvant arthritis", *Springer Semin Immunopathol.*, (1995) 16:427–436, Springer–Verlag, New York NY USA.

Bergelson, J.M. et al., "Do integrins use a 'MIDAS touch' to grasp as Asp?", *Current Biology*, 1995, vol. 5, No. 6, 615–617, Cell Press, Cambridge MA USA.

Bergeron, Raymond J. et al., "Total Synthesis of (±)–15–Deoxyspergualin", *J. Org. Chem.*, 1987, 52, 1700–1703, American Chemical Society. Washington DC USA.

Borne, R. F. et al., "Conformational Analogues of Antihypertensive Agents Related to Guanethidine", *Journal of Medicinal Chemistry*, 1977, vol. 20, No. 6, pp. 771–776, American Chemical Society, Columbus OH USA.

Büllesback, E.E., "Schutzgruppen in der Peptidsynthese (Teil 2): Mehrfunktionelle Aminosäuren—zur Abspaltung—Perspektiven der Schutzgruppentechnik", *KONTAKTE 1/80*, Torino IT.

Bundgaard, Hans, "Novel chemical approaches in prodrug design", *Drugs of the Future*, 1991, 16(5), 443–458, Prous Science, Philadelphia PA USA.

Cronstein, Bruce N. et al., "The adhesion molecules of inflammation", *Arthritis and Rheumatism*, vol. 36, No. 2, Feb. 1993, pp. 147–157, American College of Rheumatology, Atlanta GA USA.

Damle, Nitin K. et al., "Vascular cell adhesion molecule 1 induces T–cell antigen receptor–dependent activation of $CD4^+$ T lymphocytes", *Proc. Natl. Acad. Sci. USA*, vol. 88, pp. 6403–6407, Aug. 1991, National Academy of Sciences, Washington DC USA.

Davies, Stephen G. et al., "Asymmetric Synthesis of R–β–amino Butanoic Acid and S–β–tyrosine: Homochiral Lithium Amide Equivalents for Michael Additions to α,β–Unsaturated Esters", *Tetrahedron:Asymmetry*, vol. 2, No. 3, pp. 183–188, 1991, Elsevier Sciences Ltd., London UK.

Davies, Stephen G. et al., "Asymmetric Synthesis of anti–α–Alkyl–β–amino Acids", *J. Chem. Soc. Perkin Trans, 1*, 1994, pp. 1129–1139, Royal Society of Chemistry, London UK.

Dinther–Janssen, Anna C. H. M. Van et al., "The VLA–4/VCAM–1 pathway is involved in lymphocyte adhesion to endothelium in rheumatoid synovium[1]", *The Journal of Immunology*, vol. 147, 4207–4210, No. 12, Dec. 5, 1991, The American Association of Immunologists, Bethesda, MD, USA.

Elices, Mariano J., "The integrin α4β1 (VLA–4) as a therapeutic target", *Cell Adhesion and Human Disease*, 1995, Wiley, Chichester (Ciba Foundation Symposium 189) p. 79–90, John Wiley & Sons, Inc., Hoboken NJ USA.

Elices, M. J. et al., "The integrin VLA–4 mediates leukocyte recruitment to skin inflammatory sites in vivo", *Clinical and Experimental Rheumatology*, 11, (Suppl. 8): S77–S80, 1993, Pisa IT.

Elices, Mariano J. et al., "Expression and Functional Significance of alternatively spliced CS1 fibronectin in rheumatoid arthritis microvasculature", *J. Clin. Invest.*, vol. 93, Jan. 1994, 405–416, The American Society for Clinical Investigation, Inc., Ann Arbor MI USA.

Elices, Mariano J. et al., "VCAM–1 on activated endothelium interacts with the leukocyte integrin VLA–4 at a site distinct from the VLA–4/Fibronectin binding site", *Cell*, vol. 60, 577–584, Feb. 23, 1990, Cell Press, Cambridge MA USA.

Fehrentz, Jean–Alain, "An Efficient Synthesis of Optically Active α–(t–Butoxycarbonylamino)–aldehydes from α–Amino Acids", *Synthesis*, Aug. 1993, pp. 676–678.

Fleisher, David et al., "Improved oral drug delivery: solubility limitations overcome by the use of prodrugs", *Advanced Drug Delivery Reviews*, 19 (1996), 115–130, Elsevier Science B.V., Amsterdam, The Netherlands.

Foster, Carolyn A. Ph.D., "VCAM–1/α4–integrin pathway: Therapeutic target for allergic inflammatory disorders", *J. Allergy Clin. Immunol.*, vol. 98, No. 6, Part 2, S270–S277, Mosby–Year Book, Inc, Oxford, UK.

Freedman, Arnold S., "Follicular Non–Hodgkin's lymphoma cell adhesion to normal germinal centers and neoplastic follicles involves very late antigen–r and vascular cell adhesion molecule–1", *BLOOD*, vol. 79, No. 1 (Jan. 1), 1992: pp. 206–212, Birmingham, AL USA.

Hafner, L.S. et al., "Preparation of 2–Imino– and 2–Nitrimon–1,3–diazacycloalkanes", *J. Org. Chem.*, vol. 24, (1959), pp. 1157–1159, American Chemical Society, Washington DC USA.

Harlan, John M., "Leukocyte–Endothial Interactions", *BLOOD*, vol. 65, No. 3 (Mar.), 1985: pp 513–525, Birmingham, AL USA.

Hubbuch, A., "Schutzgruppen in der Peptidsynthese (Teil1): Schutgruppentaktik, Amino– und Carboxyl–Schutzgruppen", *KONTAKTE 3/79*, Torino IT.

Isobe, M. et al., "Effect of Anti–VCAM–1 and Anti–VLA–4 Monoclonal Antibodies on Cardiac Allograft Survival and Response to Soluble Antigens In Mice", *Transplantation Proceedings*, vol. 26, No. 2 (Apr.), 1994: pp. 867–868, Elsevier Science, Inc., New York, NY, USA.

Issekutz, Thomas B., "Inhibition of in vivo lymphocyte migration to inflammation and homing to lymphoid tissues by the TA–2 monoclonal antibody—a likely role for VLA–4 in vivo", *The Journal of Immunology*, vol. 147, No. 12, Dec. 15, 1991, 4178–4184, The American Association of Immunologists, Bethesda, MD, USA.

Issekutz, Thomas B. et al., "Rat Blood Neutrophils Express Very Late Antigen 4 and it Mediates Migration to Arthritic Joint and Dermal Inflammation", *J. Exp. Med.*, vol. 183, May 1996, 2174–2184, The Rockefeller University Press, New York NY USA.

Kilger, G et al., "Molecular analysis of the physiological and pathophysiological role of $α_4$integrins", *J. Mol. Med.*, (1995) 73:347–354, Springer–Verlag, New York NY USA.

Kim, Keekyung et al., "Monosubstituted Guanidines From Primary Amines and Aminolminomethanesulfonic Acid", *Tetranecron Letters*, vol. 29, No. 26, pp. 3183–3186, Pergamon Press pic, London UK.

Kolter, Thomas et al., "Synthesis of Substituted Chiral Piperazinones as Building Blocks for Peptidomimetics", *Liebigs Ann.*, 1995, 625–629, VCCH Verlagagesselschaft mbH, D–69451 Weinheim DE.

Kosynkina, Larisa et al., "A Convenient Synthesis Of Chiral Peptide Nucleic Acid (PNA) Monomers", *Tetrahedron Letters*, vol. 35, No. 29, pp. 5173–5176, 1994, Elsevier Science Ltd., London, UK.

Kuijpers, Taco W., "Pathophysiological aspects of VLA–4 interactions and possibilities for therapeutical interventions", *Springer Semin Immunopathol.*, (1995) 16:379–389, Spring–Verlag, New York NY USA.

Laffon, Armando et al., "Upregulated Expression and Function of VLA–4 Fibronectin Receptors on Human Activated T Cells in Rheumatoid Arthritis", *J. Clin. Invest.*, vol. 88, Aug. 1991, 546–552, The American Society for Clinical Investigation, Inc., Ann Arbor, MI, USA.

Martinez, Jean et al., "Synthesis and Biological Activities of Some Pseudo–Peptide Analogues of Tegragastrin: The Importance of the Peptide Backbone", *J. Med. Chem.*, 1985 28, 1874–1879, American Chemical Society Publications Support Services, Washington DC USA.

McMurray, Robert W., "Adhesion Molecules in Autoimmune Disease", *Seminars in Arthritis and Rheumatism*, vol. 25, No. 4 (Feb.), 1996: pp. 215–233, Elsevier Science USA, New York, NY USA.

Metzger, W. James, "Therapeutic approaches to asthma based on VLA–4 integrin and its counter receptors", *Springer Semin Immunopathol.* (1995) 16:467–478, Springer–Verlag, New York NY USA.

Molossi, Silvana, et al., "Blockade of Very Late Antigen–4 Integrin Binding to Fibronectin with Connecting Segment–1 Peptide Reduces Accelerated Coronary Arteriopathy in Rabbit Cardiac Allografts", *J. Clin. Invest.*, vol. 95, Jun. 1995, 2601–2610, The American Society for Clinical Investigation, Inc., Ann Arbor MI USA.

Morales–Ducret, Jeanette, "$\alpha_4/\beta_1$ Integrin (VLA–4) Ligands in Arthritis—Vascular Cell Adhesion Molecule–1 Expression in Synovium and on Fibroblast–Like Synoviocytes[1]", *The Journal of Immunology*, vol. 149, No. 4, Aug. 15, 1992, 1424–1431, The American Association of Immunologists, Bethesda, MD, USA.

Muacevic, G., "New Apparatus and Method for the toxicological Investigation of Metered Aerosols in Rats", *Arch. Toxicol.*, 34 1–8 (1975), Springer–Verlag, New York NY USA.

O'Brien, Kevin D. et al., "Vascular Cell Adhesion Molecule–1 is Expessed in Human Coronary Atherosclerotic Plaques", *J. Clin. Invest.*, vol. 92, Aug. 1993, 945–951, The American Society for Clinical Investigation, Inc., Ann Arbor MI USA.

Ockenhouse, Christian F. et al., Human Vascular Endothelial Cell Adhesion Receptors for *Plasmodium falciparum*–infected Erythrocytes: Roles for Endothelial Leukocyte Adhesion Molecule 1 and Vascular Cell Adhesion Molecule 1, *The Journal of Experimental Medicine*, vol. 176, Oct. 1992, 1183–1189, Rockefeller University Press, New York NY USA.

Osborn, Laurelee, et al., "Direct Expression Cloning of Vascular Cell Adhesion Molecule 1, a Cytokin–induced Endothelial Protein that Binds to Lymphocytes", *CELL*, vol. 59, 12–3=1211, Dec. 22, 1989, Cell Press, Cambridge MA USA.

Osborn, Laurelee, "Leukocyte Adhesion to Endothelium in Inflammation", *CELL*, vol. 62, 3–6, Jul. 13, 1980, Cell Press, Cambridge MA USA.

Poon, B.Y. et al., "Emigrated Neutrophils Regulate Ventricular Contractility via $\alpha_4$ Integrin", American Heart Association, Inc., *Lippincott Williams & Wilkins*, Baltimore MD USA.

Postigo, Antonio A. et al., "Increased Binding of Synovial T Lymphocytes from Rheumatoid Arthritis to Endothelial–Leukocyte Adhesion Molecule–1 (ELAM–1) and Vascular Cell Adhesion Molecule–1 (VCAM–1)", *J. Clin. Invest.*, vol. 89, May 1992, 1445–1452, The American Society for Clinical Investigation, Inc., Ann Arbor MI USA.

Renkonen, Risto et al., "Rapid Communication: Expression of Endothelial Adhesion Molecules In Vivo: *Increased Endothelial ICAM–2 Expression in Lymphoid Malignancies*", *American Journal of Pathology*, vol. 140, No. 4, Apr. 1992, 763–767.

Rice, G. Edgar et al., "An Inducible Endothelial Cell Surface Glycoprotein Mediates Melanoma Adhesion", *SCIENCE*, vol. 246, Dec. 8, 1989, 1303–1306, American Association for the Advancement of Science, Stanford University's High Wire Press, Palo Alto CA USA.

Ruoslahti, Erkki, "Fibronectin and its receptors", *Ann. Rev. Biochem.*, 1988, 57:375–413, Annual Reviews Inc., Palo Alto CA USA.

Scott, F. L. et al., "Studies in the Pyrazole Series. III. Substituted Guanidines", *Pyrazole Series: Substituted Guanidines*, Aug. 20, 1953, pp. 4053–4054.

Seiffge, D. et al., "Effects of Different Mediators or Cytokines and Monoclonal Antibodies to Adhesion Molecules on Leukocyte Adhesion in Rat Mesenteric Venules", *Int. J. Microcirc.*, 1995, 15, 301–308, S. Karger AG, Basel Switzerland.

Shih, Peggy T. et al., "Blocking Very Late Antigen–4 Integrin Decreases Leukocyte Entry and Fatty Streak Formation in Mice Fed an Atherogenic Diet", American Heart Association, Inc., *Lippincott Williams & Wilkins*, Baltimore MD USA.

Springer, Timothy A., "Traffic Signals for Lymphocyte Recirculation and Leukocyte Emigration: The Multistep Paradigm", *Cell*, vol. 76, 301–314, Jan. 28, 1994, Cell Press, Cambridge MA USA.

Steglich, Wolfgang et al., "Eine einfache Synthese für N–Acylimine des Hexafluor–und symm. Dichlortetrafluoraceions", *Chem. Ber.*, 107, 1488–1496 (1974).

Stoolman, Lloyd M. "Adhesion Molecules Controlling Lymphocyte Migration", *Cell*, vol. 56, 907–910, Mar. 24, 1989, Cell Press, Cambridge MA USA.

Takeuchi, Tsutomu et al., "Upregulated Expression and Function of Integrin Adhesion Receptors in Systemic Lupus Erythematosus Patients with Vasculitis", *J. Clin. Invest.*, vol. 92, Dec. 1993, 3008–3016, The American Society for Clinical Investigation, Inc., Ann Arbor MI USA.

Wagner, G. et al., "Synthese von 3–[Amidinophynyl]–ataninen und 3–[Amidinophenyl]–milchsäuren", *Pharmazie*, 29, H. 1 (1974), pp. 12–15, Wiley–VCH Verlag GmbH, Weinheim DE.

Weiss, Von Stefan et al., "Zur Guanylierung von Aminen mit O–Methyl–isoharnstoff–sulfat", *Chemiker–Zeitung*, 98 Jahrgang (1974) Nr 12, pp. 617–618, WILEY–VCH Verlag GmbH & Co. KGzA, Weinheim DE.

Wollber, Von H. et al., "2–(Guanodina)–anilide und verwandte Verbindungen", *Arzneim–Forsch, Drug Res*, 34 (I), Nr 5 (1984), pp. 531–542, Editio Cantor Verlag, Aulendorf DE.

Yang, Xiao–Dong et al., "Inhibition of insulitis and prevention of diabetes in nonobese diabetic mice by blocking L–selectin and very late antigen 4 adhesion receptors", *Proc. Natl. Acad. Sci. USA.*, vol. 90, pp. 10494–10498, Nov. 1993, National Academy of Sciences, Washington DC, USA.

Yednock, Ted A., "Prevention of experimental autoimmune encephalomyelitis by antibodies against α4β1 Integrin", *NATURE*, vol. 356, Mar. 5, 1992, pp. 63–66, Stanford CA USA.

Zettlmeissl, Gerd et al., "Expression and Characterization of Human CD4: Immunoglobulin Fusion Proteins", *DNA and Cell Biology*, vol. 9, No. 5, 1990, pp. 347–353, Mary Ann Liebert, Inc., Publishers, Larchmont NY USA.

Abraham, William M. et al., "$\alpha_4$– Integrins Mediate Antigen–Induced Late Bronchial Responses and Prolonged Airway Hyperresponsiveness in Sheep", *J. Clin. Invest.*, vol. 93, 776–787 (Feb. 1994), The American Society for Clinical Investigation, Inc., Ann Arbor MI USA.

Adams, David H. et al., "Experimental Graft Arteriosclerosis,", *Transplantation*, vol. 56, 794–799, No. 4 (Oct., 1993), Lippincott Williams & Wilkins, Baltimore MD USA.

Albelda, Steven M. et al., "Molecular and Cellular Properties of PECAM–1 (endoCAM/CD31): A Novel Vascular Cell–Cell Adhesion Molecule", *The Journal of Cell Biology*, vol. 114, No. 5, 1059–1068 (Sep. 1991), The Rockefeller University Press, New York NY USA.

Barbadillo, Carmen et al., "Anti–Integrin Immunotherapy in Rheumatoid Arthritis: Protective Effect of Anti–α4 Antibody in Adjuvant Arthritis", *Springer Semin Immunopathol.*, 16:427–436 (1995), Springer–Verlag, New York NY USA.

Bergelson, J.M. et al., "Do Integrins Use a 'MIDAS Touch' to Grasp as Asp?", *Current Biology*, vol. 5, No. 6, 615–617 (1995).

Bergeron, Raymond J. et al., "Total Synthesis of (±)–15–Deoxyspergualin", *J. Org. Chem.*, 52, 1700–1703, (1987).

Borne, R. F. et al., "Conformational Analogues of Antihypertensive Agents Related to Guanethidine", *Journal of Medicinal Chemistry*, vol. 20, No. 6, pp. 771–776 (1977).

Bundgaard, Hans, "Novel Chemical Approaches in Prodrug Design", *Drugs of the Future*, 16(5), 443–458 (1991).

Cronstein, Bruce N. et al., "The Adhesion Molecules of Inflammation", *Arthritis and Rheumatism*, vol. 36, No. 2, pp. 147–157, Feb. 1993.

Damle, Nitin K. et al., "Vascular Cell adhesin Molecule 1 Induces T–cell Antigen Receptor–Dependent Activation of CD4$^+$ T Lymphocytes", *Proc. Natl. Acad. Sci. USA*, vol. 88, pp. 6403–6407, Aug. 1991, National Academy of Sciences, Washington DC USA.

Davies, Stephen G. et al., "Asymmetric Synthesis of R–β–amino Butanoic Acid and S–β–tyrosine: Homochiral Lithium Amide Equivalents for Michael Additions to α,β–Unsaturated Esters", *Tetrahedron: Asymmetry*, vol. 2, No. 3, pp. 183–186 (1991), Elsevier Sciences Ltd., London UK.

Davies, Stephen G. et al., "Asymmetric Synthesis of anti–α–Alkyl–β–amino Acids ", *J. Chem. Soc. Perkin Trans.* 1, pp. 1129–1139 (1994).

Dinther–Janssen, Anna C. H. M. Van et al., "The VLA–4/VCAM–1 Pathway is involved in Lymphocyte Adhesion to Endothelium in Rheumatoid Synovium", *The Journal of Immunology*, vol. 147, 4207–4210, No. 12, Dec. 5, 1991.

Elices, Mariano J., "The Integrin α4β1 (VLA–4) as a Therapeutic Target", *Cell Adhesion and Human Disease,*, Ciba Foundation Symposium, 189, p. 79–90 (1995), John Wiley & Sons, Inc., Hoboken NJ USA.

Elices, M. H. et al., "The integrin VLA–4 Mediates Leukocyte Recruitment to Skin Inflammatory Sites in Vivo", *Clinical and Experimental Rheumatology*, 11, (Suppl. 8): S77–S80, 1993.

Elices, Mariano J. et al., "Expression and Functional Significance of Alternatively Spliced CS1 Fibronectin in Rheumatoid Arthritis Microvasculature", *J. Clin. Invest.*, vol. 93, 405–416 (1994).

Elices, Mariano J. et al., "VCAM–1 on Activated Endothelium Interacts with the Leukocyte Integrin VLA–4 at a Site Distinct from the VLA–4/Fibronectin Binding Site", *Cell*, vol. 60, 577–584 (1990), Cell Press, Cambridge MA USA.

Fehrentz, Jean–Alain et al., "An Efficient Synthesis of Optically Active α–(t–Butoxycarbonylamino)–Aldehydes from α–Amino Acids", *Synthesis*, pp. 676–678 (1993).

Fleisher, David et al., "Improved Oral Drug Delivery: Solubility Limitations Overcome by the Use of Prodrugs", *Advanced Drug Delivery Reviews*, 19, 115–130 (1996), Elsevier Science B.V., Amsterdam, The Netherlands.

Foster, Carolyn A. Ph.D., "VCAM–1/α4–Integrin Adhesion Pathway: Therapeutic Target for Allergic Inflammatory Disorders", *J. Allergy Clin. Immunol.*, vol. 98, No. 6, Part 2, S270–S277 (1996), Mosby–Year Book, Inc, Oxford, UK.

Freedman, Arnold S. et al., "Folicular Non–Hodgkin's Lymphoma Cell Adhesion to Normal Germinal Centers and Neoplastic Follicles Involves Very Late Antigen–4 and Vascular Cell Adhesion Molecule–1", *Blood*, vol. 79, No. 1 pp. 206–212. (1992), Birmingham, AL USA.

Hafner, L.S. et al., "Preparation of 2–Imino– and 2–Nitrimon–1,3–diazacycloalkanes", *J. Org. Chem.* , vol. 24, pp. 1157–1159 (1959), American Chemical Society, Washington DC USA.

Harlan, John M., "Leukocyte–Endothelial Interactions", *Blood*, vol. 65, No. 3 , pp 513–525 (1985), Birmingham, AL USA.

Isobe, M. et al., "Effect of Anti–VCAM–1 and Anti–VLA–4 Monoclonal Antibodies on Cardiac Allograft Survival and Response to Soluble Antigens in Mice", *Transplantation Proceedings*, vol. 28, No. 2, pp. 867–868 (1994), Elsevier Science, Inc., New York, NY, USA.

Issekutz, Thomas B., "Inhibition of in Vivo Lymphocyte Migration to Inflammation and Homing to Lymphoid Tissues by the TA–2 Monoclonal Antibody—a Likely Role for VLA–4 In Vivo", *The Journal of Immunology*, vol. 147, No. 12, 4178–4184 (Dec. 15, 1991), The American Association of Immunologists, Bethesda, MD, USA.

Issekutz, Thomas B. et al., "Rat Blood Neutrophils Express Very Late Antigen 4 and it Mediates Migration to Arthritic Joint and Dermal Inflammation", *J. Exp. Med.*, vol. 183, 2174–2184 (1996), The Rockefeller University Press, New York NY USA.

Kilger, G et al., "Molecular Analysis of the Physiological and Pathophysiological Role of $\alpha_4$–Integrins", *J. Mol. Med.*, 73:347–354 (1995), Springer–Verlag, New York NY USA.

Kim, Keekyung et al., "Monosubstituted Guanidines From Primary Amines and Aminoiminomethanesulfonic Acid", *Tetrahedron Letters*, vol. 29, No. 26, pp. 3183–3186, Pergamon Press pic, London UK.

Kolter, Thomas et al., "Synthesis of Substituted Chiral Piperazinones as Building Blocks for Peptidomimetics", *Liebigs Ann.*, 625–629, 1995, VCCH Verlagsgesselschaft mbH, D–69451 Weinheim DE.

Kosynkina, Larisa et al., "A Convenient Synthesis Of Chiral Peptide Nucleic Acid (PNA) Monomers", *Tetrahedron Letters*, vol. 35, No. 29, pp. 5173–5176 (1994), Elsevier Science LTD., London, UK.

Kuijpers, Taco W., "Pathophysiological Aspects of VLA–4 Interactions and Possibilities for Therapeutical Interventions", *Springer Semin Immunopathol.*, 16:379–389 (1995), Spring–Verlag, New York NY USA.

Laffón, Armando et al., "Upregulated Expression and Function of VLA–4 Fibronectin Receptors on Human Activated T Cells in Rheumatoid Arthritis", *J. Clin. Invest.*, vol. 88, 546–552 (1991), The American Society for Clinical Investigation, Inc., Ann Arbor, MI, USA.

Martinez, Jean et al., "Synthesis and Biological Activities of Some Pseudo–Peptide Analogues of Tegragastrin: The Importance of the Peptide Backbone", *J. Med. Chem.*, 26, 1874–1879 (1985), American Chemical Society Publications Support Services, Washington DC USA.

McMurray, Robert W., "Adhesion Molecules in Autoimmune Disease", *Seminars in Arthritis and Rheumatism*, vol. 25, No. 4, pp. 215–233 (1996), Elsevier Science USA, New York, NY USA.

Metzger, W. James, "Therapeutic Approaches to Asthma Based on VLA–4 Integrin and Its Counter Receptors", *Springer Semin Immunopathol.*, 16:467–478, (1995) Springer–Verlag, New York NY USA.

Molossi, Silvana, et al., "Blockade of Very Late Antigen–4 Integrin Binding to Fibronectin with Connecting Segment–1 Peptide Reduces Accelerated Coronary Arteriopathy in Rabbit Cardiac Allografts", *J. Clin. Invest.*, vol. 95, 2601–2610 (1995), The American Society for Clinical Investigation, Inc., Ann Arbor MI USA.

Morales–Ducret, Jeanette et al., "$\alpha_4/\beta_1$ Integrin (VLA–4) Ligands in Arthritis—Vascular Cell Adhesion Molecule–1 Expression in Synovium and on Fibroblast–Like Synoviocytes[1]", *The Journal of Immunology*, vol. 149, No. 4, 1424–1431 (Aug. 15, 1992), The American Association of Immunologists, Bethesda, MD, USA.

Muacevic, G., "New Apparatus and Method for the Toxicological Investigation of Metered Aerosols in Rats", *Arch. Toxicol.*, vol. 34, 1–8 (1975), Springer–Verlag, New York NY USA.

O'Brien, Kevin D. et al., "Vascular Cell Adhesion Molecule–1 is Expressed in Human Coronary Atherosclerotic Plaques", *J. Clin. Invest.*, vol. 92, 945–951 (Aug. 1993), The American Society for Clinical Investigation, Inc., Ann Arbor MI USA.

Ockenhouse, Christian F. et al., Human Vascular Endothelial Cell Adhesion Receptors for *Plasmodium falciparum*–infected Erythrocytes: Roles for Endothelial Leukocyte Adhesion Molecule 1 and Vascular Cell Adhesion Molecule 1, *J. Exp. Med.*, vol. 176, 1183–1189 (Oct. 1992), Rockefeller University Press, New York NY USA.

Osborn, Laurelee, et al., "Direct Expression Cloning of Vascular Cell Adhesion Molecule 1, a Cytokin–Induced Endothelial Protein that Binds to Lymphocytes", *Cell*, vol. 59, pp. 1203–1211 (Dec. 22, 1989), Cell Press, Cambridge MA USA.

Poon, B.Y. et al., "Emigrated Neutrophils Regulate Ventricular Contractility via $\alpha_4$ Integrin", *Circulation Research*, vol. 84, pp. 1245–1251 (1999).

Postigo, Antonio A. et al., "Increased Binding of Synovial T Lymphocytes from Rheumatoid Arthritis to Endothelial–Leukocyte Adhesion Molecule–1 (ELAM–1) and Vascular Cell Adhesion Molecle–1 (VCAM–1", *J. Clin. Invest.*, vol. 89, 1445–1452 (1992).

Renkonen, Risto et al., "Rapid Communication: Expression of Endothelial Adhesion Molecules in Vivo: *Increased Endothelial ICAM–2 Expression in Lymphoid Malignancies*", American Journal of Pathology, vol. 140, No. 4, 763–767 (1992).

Rice, G. Edgar et al., "An Inducible Endothelial Cell Surface Glycoprotein Mediates Melanoma Adhesion", *Science*, vol. 246, 1303–1306 (1989).

Ruoslahti, Erkki, "Fibronectin and its Receptors", *Ann. Rev. Biochem.*, 57:375–413 (1988).

Scott, F. L. et al., "Studies in the Pyrazole Series. III. Substituted Guanidines", *Pyrazole Series: Substituted Guanidines*, pp. 4053–4054 (Aug. 20, 1953).

Seiffge, D. et al., "Effects of Different Mediators or Cytokines and Monoclonal Antibodies to Adhesion Molecules on Leukocyte Adhesion in Rat Mesenteric Venules", *Int. J. Microcirc.*, 15, 301–308 (1995), S. Karger AG, Basel Switzerland.

Shih, Peggy T. et al., "Blocking Very Late Antigen–4 Integrin Decreases Leukocyte Entry and Fatty Streak Formation in Mice Fed an Atherogenic Diet", *Circulation Research*, vol. 84, p. 345–351 (1999).

Springer, Timothy A., "Traffic Signals for Lymphocyte Recirculation and Leukocyte Emigration: The Multistep Paradigm", *Cell*, vol. 76, 301–314 (1994).

Steglich, Wolfgang et al., "Eine einfache Syntheses für N–Acylimine des Hexafluor–und symm. Dichlortetrafluoracetons", *Chem. Ber.*, vol. 107, pp. 1488–1498 (1974).

Stoolman, Lloyd M., "Adhesion Molecules Controlling Lymphocyte Migration", *Cell*, vol. 56, pp. 907–910 (1989).

Takeuchi, Tsutomu et al., "Upregulated Expression and Function of Integrin Adhesion Receptors in Systemic Lupus Erythematosus Patients with Vasculitis", *J. Clin. Invest.*, vol. 92, 3008–3016 (1993).

Wagner, G. et al., "Synthese von 3–[Amindinophynyl]–alaninen und 3–[Amidinophenyl]–milchsäuren", *Pharmazie*, vol. 29, H. 1 (1974), pp. 12–15, WILEY–VCH Verlag GmbH, Weinheim DE.

Weiss, Von Stefan et al., "Zur Guanylierung von Aminen mit O–Methyl–isoharnstoff–sulfat", *Chemiker–Zeitung*, 98 Nr 12, pp. 617–618 (1974), WILEY–VCH Verlag GmbH & Co. KGaA, Weinheim DE.

Wollweber, Von H. et al., "2–(Guanidino)–anilide und verwandte Verbindungen", *Arzneim–Forsch. Drug Res*, 34 (I), Nr 5, pp. 531–542 (1984), Editio Cantor Vergal, Aulendorf DE.

Yang, Xiao–Dong et al., "Inhibition of Insulitis and Prevention of Diabetes in Nonobese Diabetic Mice by Blocking L–selectin and Very Late Antigen 4 Adhesion Receptors", *Proc. Natl. Acad. Sci. USA*, vol. 90, pp. 10494–10498 (1993).

Yednock, Ted A. et al., "Prevention of Experimental Autoimmune Encephalomyelitis by Antibodies Against $\alpha 4 \beta 1$ integrin", *Nature*, vol. 356, pp. 63–66 (1992).

Zettlmeissl, Gerd et al., "Expression and Characterization of Human CD4: Immunoglobulin Fusion Proteins", *DNA and Cell Biology*, vol. 9, No. 5, pp. 347–353 (1990).

US 6,962,937 B2

IMIDAZOLIDINE DERIVATIVES, THEIR PREPARATION AND THEIR USE

This application claims priority to German Patent Application 10137595.6, filed Aug. 1, 2001, which is hereby incorporated by reference, in its entirety. All references cited below, including patents, patent applications and scientific journals and books also are herein incorporated by reference in their entirety.

FIELD OF THE INVENTION

The present invention relates to novel imidazolidine derivatives of the formula I,

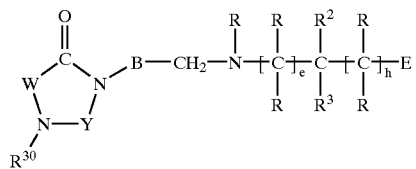

in which B, E, W, Y, R, $R^2$, $R^3$, $R^{30}$, e and h have the meanings given below. The compounds of the formula I are valuable pharmaceutically active compounds which are suitable, for example, for treating inflammatory diseases (e.g., rheumatoid arthritis, or allergic diseases). The compounds of the formula I are inhibitors of the adhesion and migration of leukocytes and/or antagonists of the adhesion receptor VLA-4 belonging to the integrin group. They are generally suitable for treating diseases, which are caused by, or associated with, an undesirable degree of leukocyte adhesion and/or leukocyte migration or in which cell-cell or cell-matrix interactions, which are based on interactions of VLA-4 receptors with their ligands, play a role. The invention furthermore relates to processes for preparing the compounds of the formula I, to the use of the compounds and to pharmaceutical preparations, which comprise the compounds of the formula I.

BACKGROUND OF THE INVENTION

The integrins are a group of adhesion receptors, which play an essential role in cell-cell-binding and cell-extracellular matrix-binding processes. They possess an αβ-heterodimeric structure, have a wide cellular distribution and display a high degree of evolutionary conservation. The integrins include, for example, the fibrinogen receptor on blood platelets, which receptor interacts, in particular, with the RGD sequence of fibrinogen, and the vitronectin receptor on osteoclasts, which receptor interacts, in particular, with the RGD sequence of vitronectin or osteopontin. The integrins are divided into three major groups, i.e., the β2 subfamily, containing the representatives LFA-1, Mac-1 and p150/95, which are responsible, in particular, for cell-cell interactions in the immune system, and the subfamilies β1 and β3, whose representatives principally mediate the adhesion of cells to components of the extracellular matrix (Ruoslahti, *Annu. Rev. Biochem.*, 1988, 57:375). The integrins belonging to the β1 subfamily, which also are called VLA (very late (activation) antigen) proteins, include at least six receptors which interact specifically with fibronectin, collagen and/or laminin as ligands. Within the VLA family, the integrin VLA-4 (α4β1) is a typical, insofar as it is mainly restricted to lymphoid and myeloid cells, and in these cells is responsible for cell-cell interactions with a large number of other cells. For example, VLA-4 mediates the interaction of T lymphocytes and B lymphocytes with the heparin II-binding fragment of human plasma fibronectin (FN). The binding of VLA-4 to the heparin II-binding fragment of plasma fibronectin is based, in particular, on an interaction with an LDVP sequence. In contrast to the fibrinogen receptor or the vitronectin receptor, VLA-4 is not a typical RGD-binding integrin (Kilger and Holzmann, *J. Mol. Meth.*, 1995, 73:347).

Normally, the leukocytes, which are circulating in the blood, only exhibit a low degree of affinity for the vascular endothelial cells, which line the blood vessels. Cytokines, which are released from inflamed tissue, activate endothelial cells and thus the expression of a large number of cell surface antigens. These antigens include, for example, the adhesion molecules ELAM-1 (endothelial cell adhesion molecule 1; also called E selectin), which binds neutrophils, inter alia, ICAM-1 (intercellular adhesion molecule 1), which interacts with LFA-1 (leukocyte function-associated antigen 1) on leukocytes, and VCAM-1 (vascular cell adhesion molecule 1), which binds various leukocytes, inter alia lymphocytes (Osborn et al., *Cell*, 1989, 59:1203). Like ICAM-1, VCAM-1 is a member of the immunoglobulin gene superfamily. VCAM-1 (first known as INCAM-110) was identified as an adhesion molecule, which is induced on endothelial cells by inflammatory cytokines, such as TNF and IL-1 and lipopolysaccharides (LPS). Elices et al. (*Cell*, 1990, 60:577) demonstrated that VLA-4 and VCAM-1 form a receptor-ligand pair which mediates the adhesion of lymphocytes to activated endothelium. The binding of VCAM-1 to VLA-4 does not take place here by means of an interaction of the VLA-4 with an RGD sequence since VCAM-1 does not contain such a sequence (Bergelson et al., *Current Biology*, 1995, 5:615). However, VLA-4 also appears on other leukocytes, and the adherence of leukocytes other than lymphocytes also is mediated by way of the VCAM-1/VLA-4 adhesion mechanism. VLA-4 thus represents a solitary example of a β1 integrin receptor which, by way of the ligands VCAM-1 and fibronectin, plays an essential role both in cell-cell interactions and in cell-extracellular matrix interactions.

The cytokine-induced adhesion molecules play an important role in recruiting leukocytes into extravascular tissue regions. Leukocytes are recruited into inflammatory tissue regions by cell adhesion molecules which are expressed on the surface of endothelial cells and serve as ligands for leukocyte-cell surface proteins or protein complexes (receptors) (the terms ligand and receptor also can be used vice versa). Leukocytes from the blood have first of all to adhere to endothelial cells before they are able to migrate into the synovium. Since VCAM-1 binds to cells, which carry the integrin VLA-4 (α4β1), such as eosinophils, T lymphocytes, B lymphocytes, monocytes and neutrophils, it, and the VCAM-1/VLA-4-mechanism, are responsible for the function of recruiting such cells from the blood stream into infected regions and inflammation foci (Elices et al., *Cell*, 1990, 60:577; Osborn, *Cell*, 1990, 62:3; Issekutz et al., *J. Exp. Med.*, 1996, 183:2175).

The VCAM-1/VLA-4 adhesion mechanism has been connected to a number of physiological and pathological processes. In addition to cytokine-induced endothelium, VCAM-1 also is expressed, inter alia, by the following cells: myoblasts, lymphoid dendritic cells and tissue macrophages, rheumatoid synovium, cytokine-stimulated neural cells, parietal epithelial cells of the Bowman's capsule, the renal tubular epithelium, inflamed tissue in connection with heart and kidney transplant rejection, and intestinal tissue in connection with graft-versus-host disease. VCAM-1 also is found to be expressed on those areas of the arterial endothelial tissue, which correspond to early atherosclerotic plaques in a rabbit model. In addition, VCAM-1 is expressed on the follicular dendritic cells in human lymph nodes and is present on stroma cells of the bone marrow, for example, in the mouse. The latter finding suggests that VCAM-1 has a function in B cell development. Apart from cells of hematopoietic origin, VLA-4 also is found, for example, on melanoma cell lines, and the VCAM-1/VLA-4 adhesion mechanism is connected to the metastasis of such tumors (Rice et al., Science, 1989, 246:1303).

The principle form in which VCAM-1 occurs in vivo on endothelial cells, and which is the dominant form in vivo, is designated as VCAM-7D and carries seven immunoglobulin domains. The amino acid sequences of domains 4, 5 and 6 resemble those of domains 1, 2 and 3. The fourth domain is removed, by alternative splicing, in another form, which is composed of six domains and which is designated here as VCAM-6D. VCAM-6D also is able to bind VLA-4-expressing cells.

Further information with regard to VLA-4, VCAM-1, integrins and adhesion proteins can be found, for example, in the articles by Kilger and Holzmann, *J. Mol. Meth.*, 1995, 73:347; Elices, Cell Adhesion in Human Disease, Wiley, Chichester 1995, p. 79 and Kuijpers, *Springer Semin. Immunopathol.*, 1995, 16:379.

On account of the role of the VCAM-1/VLA-4 mechanism in cell adhesion processes, which are of importance, for example, in infections, inflammations and atherosclerosis, attempts have been made to control these diseases, in particular, for example, inflammations (Osborn et al., *Cell*, 1989, 59:1203), by intervening in these adhesion processes. A method for doing this is the use of monoclonal antibodies, which are directed against the VLA-4. Monoclonal antibodies (Mabs) of this type, which, as VLA-4 antagonists, block the interaction between VCAM-1 and VLA-4, are known. Thus, the anti-VLA-4 Mabs HP2/1 and HP1/3, for example, inhibit the adhesion of VLA-4-expressing Ramos cells (B cell-like cells) to human umbilical cord endothelial cells and to VCAM-1-transfected COS cells. In the same way, the anti-VCAM-1 Mab 4B9 inhibits the adhesion of Ramos cells, Jurkat cells (T cell-like cells) and HL60 cells (granulocyte-like cells) to COS cells, which have been transfected with genetic constructs that cause VCAM-6D and VCAM-7D to be expressed. In vitro data, obtained using antibodies, which are directed against the $\alpha 4$ subunit of VLA-4, show that the adhesion of lymphocytes to synovial endothelial cells, which adhesion plays a role in rheumatoid arthritis, is blocked (van Dinther-Janssen et al., *J. Immunol.*, 1991, 147:4207).

In vivo experiments have demonstrated that anti-$\alpha 4$ Mab can inhibit an experimental autoimmune encephalomyelitis. A monoclonal antibody directed against the $\alpha 4$ chain of VLA-4 likewise blocks the migration of leukocytes into an inflammation focus. The ability of antibodies to exert an effect on the VLA-4-dependent adhesion mechanism also has been examined in an asthma model, in order to investigate the role of VLA-4 in recruiting leukocytes into inflamed lung tissue (WO-A-93/13798). The administration of anti-VLA-4 antibodies inhibited the late phase reaction and the airway hyperreaction in allergic sheep. The significance of VLA-4 as a target for treating asthma is discussed in detail in Metzger, *Springer Semin. Immunopathol.*, 1995, 16:467.

The VLA-4 dependent cell adhesion mechanism also has been investigated in a primate model of inflammatory bowel disease (IBD). In this model, which corresponds to ulcerative colitis in humans, the administration of anti-$\alpha 4$ antibodies resulted in a significant reduction in the acute inflammation.

In addition to the conditions discussed above, it has been demonstrated that VLA-4-dependent cell adhesion plays a role in the following clinical conditions, including the following chronic inflammatory processes: rheumatoid arthritis (Cronstein and Weismann, *Arthritis Rheum.*, 1993, 36:147; Elices et al., *J. Clin. Invest.*, 1994, 93:405), diabetes mellitus (Yang et al., *Proc. Natl. Acad. Sci. USA*, 1993, 90:10494), systemic lupus erythematosus (Takeuchi et al., *J. Clin. Invest.*, 1993, 92:3008), delayed-type allergies (type IV allergy) (Elices et al., *Clin. Exp. Rheumatol.*, 1993, 11:S77), multiple sclerosis (Yednock et al., *Nature*, 1992, 356:63), malaria (Ockenhouse et al., *J. Exp. Med.*, 1992, 176:1183), atherosclerosis (O'Brien et al., *J. Clin. Invest.*, 1993, 92:945; Shih et al., *Circ. Res.*, 1999, 84:345), transplantation (Isobe et al., *Transplantation Proceedings*, 1994, 26:867), various malignancies, for example, melanoma (Renkonen et al., *Am. J. Pathol.*, 1992, 140:763), lymphoma (Freedman et al., *Blood*, 1992, 79:206) and others (Albelda et al., *J. Cell Biol.*, 1991, 114:1059).

The interaction of VLA-4 with VCAM-1 and fibronectin has been connected to some pathophysiological processes in cardiovascular diseases. In an in vitro cell system, immigrated neutrophils inhibit the shortening (negative inotropy) of cardiomyocytes by 35%. It was possible to inhibit this negative inotropic effect of neutrophils by an anti-$\alpha 4$ antibody, but not an anti-CD18 antibody, (Poon et al., *Circ. Res.*, 1999, 84:1245). The importance of VLA-4 in the pathogenesis of atherosclerosis has been demonstrated in a mouse model of atherosclerosis. Thus, the CS-1 peptide, which is directed against the VLA-4-binding site on fibronectin, inhibits the recruiting of leukocytes and the accumulation of fat in the aorta and consequently the formation of atherosclerotic plaques in atherogenically fed LDL receptor-knockout mice (Shih et al., *Circ. Res.*, 1999, 84:345). Using the same CS-1 peptide, it was furthermore possible to show in a heterotopic rabbit heart transplantation model that the formation of a transplant vasculopathy can be significantly reduced by blockade of the interaction of VLA-4 and fibronectin (Molossi et al., *J. Clin. Invest.*, 1995, 95:2601). WO-A-00/02903 describes CS-1 peptidomimetics which contain an aspartic acid unit, or a derivative thereof, in the molecule and which inhibit the binding of VLA-4 to the CS-1 sequence of the matrix protein fibronectin.

Accordingly, blocking VLA-4 by suitable antagonists offers possibilities of achieving an effective treatment, in particular, for example, of treating various inflammatory conditions, including asthma and IBD. The particular relevance of VLA-4 antagonists for treating rheumatoid arthritis follows from the fact that leukocytes from the blood initially adhere to endothelial cells before they are able to migrate into the synovium, and that the VLA-4 receptor plays a role in this adhesion. As mentioned above, inflammatory agents induce VCAM-1 on endothelial cells (Osborn, *Cell*, 1990, 62:3; Stoolman, *Cell*, 1989, 56:907), and various leukocytes are recruited into areas of infection and foci of inflammation. In this connection, T cells adhere to an activated endothelium, mainly via the LFA-1/ICAM-1 and VLA-4/VCAM-1 adhesion mechanisms (Springer, *Cell*, 1994, 76:301). In rheumatoid arthritis, the binding capacity of VLA-4 for VCAM-1 is increased on most synovial T cells (Postigo et al., *J. Clin. Invest*, 1992, 89:1445). In addition, an increased adhesion of synovial T cells to fibronectin has been observed (Laffon et al., *J. Clin. Invest.*, 1991, 88:546; Morales-Ducret et al., *J. Immunol.*, 1992, 149:1424). Thus, VLA-4 is up-regulated with respect to its expression and its function on T lymphocytes of the rheumatoid synovial membrane. By blocking the binding of VLA-4 to its physiological ligands VCAM-1 and fibronectin, particular inflammatory processes can be effectively prevented or alleviated. This also is confirmed by experiments, using the antibody HP2/1, which were carried out on Lewis rats suffering from adjuvant arthritis and in which effective disease prevention was observed (Barbadillo et al., *Springer Semin. Immunopathol.*, 1995, 16:427). Thus, VLA-4 is an important therapeutic target molecule.

The abovementioned VLA-4 antibodies, and the use of antibodies as VLA-4 antagonists, are described in the patent applications WO-A-93/13798, WO-A-93/15764, WO-A-94/16094, WO-A-94/17828 and WO-A-95/19790. Patent applications WO-A-94/15958, WO-A-95/15973, WO-A-96/00581, WO-A-96/06108 and WO-A-96/20216 describe peptide compounds, which are VLA-4 antagonists. However, the use of antibodies and peptide compounds as pharmaceuticals suffers from disadvantages, for example, lack of oral availability, easy degradability or an immunogenic action on longer-term administration, and thus there is a need for VLA-4 antagonists possessing a favorable property profile for use in the therapy and prophylaxis of various disease states.

WO-A-95/14008, WO-A-93/18057, U.S. Pat. No. 5,658,935, U.S. Pat. No. 5,686,421, U.S. Pat. No. 5,389,614, U.S. Pat. No. 5,397,796, U.S. Pat. No. 5,424,293 and U.S. Pat. No. 5,554,594 describe substituted 5-membered ring heterocycles, which possess an amino, amidino or guanidino function at the N-terminal end of the molecule and which exhibit platelet aggregation-inhibiting effects. EP-A-796 855 describes other heterocycles, which are inhibitors of bone resorption. EP-A-842 943, EP-A-842 945 and EP-A-842 944 describe that compounds from these series, and other compounds, surprisingly also inhibit leukocyte adhesion and are VLA-4 antagonists.

EP-A-903 353, EP-A-905 139, EP-A-918 059, WO-99/23063, WO-A-99/24398, WO-A-99/54321, WO-A-99160015 and WO-A-00/69831 describe other compounds that inhibit leukocyte adhesion and are VLA-4 antagonists. Further investigations also have shown that the compounds of the present invention surprisingly are strong inhibitors of leukocyte adhesion and antagonists of VLA-4.

SUMMARY OF THE INVENTION

The present invention relates to novel imidazolidine derivatives of the formula I,

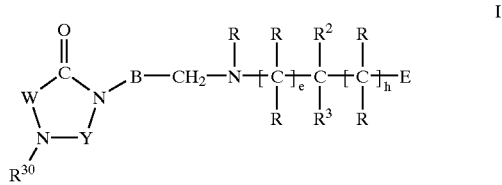

in which B, E, W, Y, R, $R^2$, $R^3$, $R^{30}$, e and h have the meanings given herein. The compounds of the formula I are valuable pharmaceutically active compounds which are suitable, for example, for treating inflammatory diseases, for example, rheumatoid arthritis, or allergic diseases. The compounds of the formula I are inhibitors of the adhesion and migration of leukocytes and/or antagonists of the adhesion receptor VLA-4, which belongs to the integrin group. They are generally suitable for treating diseases which are caused by, or associated with, an undesirable degree of leukocyte adhesion and/or leukocyte migration or in which cell-cell or cell-matrix interactions, which are based on the interactions of VLA-4 receptors with their ligands, play a role. The invention furthermore relates to processes for preparing the compounds of the formula I, to their use and to pharmaceutical preparations which comprise compounds of the formula I.

DETAILED DESCRIPTION OF THE EMBODIMENTS

The present invention relates to compounds of the formula I,

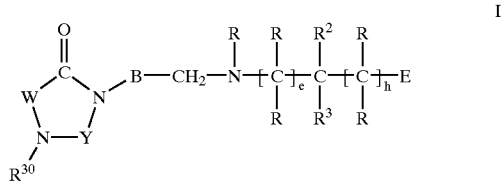

in which

W is a divalent residue selected from the group consisting of $R^1$-A-C($R^{13}$), $R^1$-A-C($R^{13}$)=C,

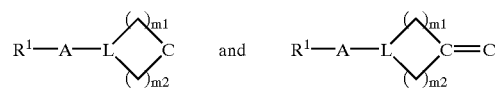

in which the ring systems

can contain one or two identical or different ring heteroatoms selected from the group consisting of nitrogen, oxygen and sulfur, can be saturated, monounsaturated or polyunsaturated, and can be substituted by 1, 2 or 3 identical or different $R^{13}$ substituents and/or by one or two oxo substituents and/or thioxo substituents, and in which L is $C(R^{13})$ or N, and in which m1 and m2 are, independently of each other, 0, 1, 2, 3, 4, 5 or 6, but the sum m1+m2 is 1, 2, 3, 4, 5 or 6;

Y is a carbonyl group, thiocarbonyl group or methylene group;

A is a direct linkage, one of the divalent residues $(C_1-C_6)$-alkylene, $(C_3-C_7)$-cycloalkylene, phenylene, phenylene-$(C_1-C_6)$-alkyl and phenylene-$(C_2-C_6)$-alkenyl, or a divalent residue of a 5-membered or 6-membered, saturated or unsaturated heterocycle, which can contain one or two ring nitrogen atoms and can be monosubstituted or disubstituted by identical or different substituents selected from the group consisting of $(C_1-C_6)$-alkyl, oxo and thioxo, where in the residues phenylenealkyl and phenylenealkenyl the residue $R^1$ is bonded to the phenylene group;

B is a divalent residue selected from the group consisting of $(C_1-C_6)$-alkylene, $(C_2-C_6)$-alkenylene, phenylene, phenylene-$(C_1-C_3)$-alkyl, $(C_1-C_3)$-alkylenephenyl and $(C_1-C_3)$-alkylenephenyl-$(C_1-C_3)$-alkyl, where the $(C_1-C_6)$-alkylene residue and the $(C_2-C_6)$-alkenylene residue are unsubstituted or substituted by one or more identical or different residues selected from the group consisting of $(C_1-C_8)$-alkyl, $(C_2-C_8)$-alkenyl, $(C_2-C_8)$-alkynyl, $(C_3-C_{10})$-cycloalkyl, $(C_3-C_{10})$-cycloalkyl-$(C_1-C_6)$-alkyl, optionally substituted $(C_6-C_{14})$-aryl, $(C_6-C_{14})$-aryl-$(C_1-C_6)$-alkyl which is optionally substituted in the aryl residue, optionally substituted heteroaryl and heteroaryl-$(C_1-C_6)$-alkyl which is optionally substituted in the heteroaryl residue;

E is tetrazolyl, $(R^8O)_2P(O)$, $R^{10}OS(O)_2$, $R^9NHS(O)_2$, $R^6CO$, $R^7CO$, $R^{10}CO$, HCO, $R^8O$—$CH_2$, $R^8CO$—O—$CH_2$, $R^{8a}O$—CO—O—$CH_2$ or $(R^8O)_2P(O)$—O—$CH_2$;

R is hydrogen, $(C_1-C_8)$-alkyl, $(C_3-C_{12})$-cycloalkyl, $(C_3-C_{12})$-cycloalkyl-$(C_1-C_8)$-alkyl, optionally substituted $(C_6-C_{14})$-aryl, $(C_6-C_{14})$-aryl-$(C_1-C_8)$-alkyl which is optionally substituted in the aryl residue, optionally substituted heteroaryl or heteroaryl-$(C_1-C_8)$-alkyl which is optionally substituted in the heteroaryl residue, where all the residues R are independent of each other and the residues R can be identical or different;

$R^1$ is hydrogen, $(C_1-C_{10})$-alkyl which can be optionally monosubstituted or polysubstituted by fluorine, $(C_3-C_{12})$-cycloalkyl, $(C_3-C_{12})$-cycloalkyl-$(C_1-C_8)$-alkyl, $R^{21}$—$((C_6-C_{14})$-aryl) which is optionally substituted in the aryl residue, $(R^{21}$—$((C_6-C_{14})$-aryl))-$(C_1-C_8)$-alkyl which is optionally substituted in the aryl residue, the residue Het, or the residue Het-$(C_1-C_8)$-alkyl, or is one of the residues X—NH—C(=NH)—$R^{20}$—, $X^1$—NH—$R^{20}$—, $R^{21}O$—$R^{20}$—, $R^{21}N(R^{21})$—$R^{20}$—, $R^{21}C(O)$—, $R^{21}O$—$C(O)$—, $R^{22}N(R^{21})$—$C(O)$—, $R^{22}C(O)$—$N(R^{21})$—, $R^{21}O$—N=, oxo or thioxo;

X is hydrogen, $(C_1-C_6)$-alkyl, $(C_1-C_6)$-alkylcarbonyl, $(C_1-C_6)$-alkoxycarbonyl, $(C_1-C_{10})$-alkylcarbonyloxy-$(C_1-C_6)$-alkoxycarbonyl, optionally substituted $(C_6-C_{14})$ arylcarbonyl, optionally substituted $(C_6-C_{14})$-aryloxycarbonyl, $(C_6-C_{14})$-aryl-$(C_1-C_6)$-alkoxycarbonyl which also can be substituted in the aryl residue, cyano, hydroxyl, $(C_1-C_6)$-alkoxy, $(C_6-C_{14})$-aryl-$(C_1-C_6)$-alkoxy optionally substituted in the aryl residue, or amino;

$X^1$ has one of the meanings of X or is R'—NH—C(=N—R"), in which R' and R", independently of each other, have one of the meanings of X;

$R^2$ is hydrogen, $(C_1-C_8)$-alkyl, optionally substituted $(C_6-C_{14})$-aryl, $(C_6-C_{14})$-aryl-$(C_1-C_8)$-alkyl which is optionally substituted in the aryl residue, or $(C_3-C_8)$-cycloalkyl;

$R^3$ is hydrogen, $(C_1-C_{10})$-alkyl which can be optionally monosubstituted or polysubstituted by fluorine, optionally substituted $(C_6-C_{14})$-aryl, $(C_6-C_{14})$-aryl-$(C_1-C_8)$-alkyl which is optionally substituted in the aryl residue, optionally substituted heteroaryl, heteroaryl-$(C_1-C_8)$-alkyl which is optionally substituted in the heteroaryl residue, $(C_3-C_8)$-cycloalkyl, $(C_3-C_8)$-cycloalkyl-$(C_1-C_8)$-alkyl, $(C_6-C_{12})$-bicycloalkyl, $(C_6-C_{12})$-bicycloalkyl-$(C_1-C_8)$-alkyl, $(C_6-C_{12})$-tricycloalkyl, $(C_6-C_{12})$-tricycloalkyl-$(C_1-C_8)$-alkyl, $(C_2-C_8)$-alkenyl, $(C_2-C_8)$-alkynyl, $R^{11}NH$, CON$(CH_3)R^4$, CONHR$^4$, COOR$^{21}$, COOR$^{15}$, CON$(CH_3)R^{15}$ or CONHR$^{15}$;

$R^4$ is hydrogen or $(C_1-C_{10})$-alkyl which is unsubstituted or monosubstituted or polysubstituted by identical or different residues selected from the group consisting of hydroxyl, $(C_1-C_8)$-alkoxy, $R^5$, optionally substituted $(C_3-C_8)$-cycloalkyl, hydroxycarbonyl, aminocarbonyl, mono- or di-$((C_1-C_{10})$-alkyl)aminocarbonyl, $(C_6-C_{14})$-aryl-$(C_1-C_8)$-alkoxycarbonyl optionally substituted in the aryl residue, $(C_1-C_8)$-alkoxycarbonyl, $R^6$—CO, $R^7$—CO, tetrazolyl and trifluoromethyl;

$R^5$ is optionally substituted $(C_6-C_{14})$-aryl, $(C_6-C_{14})$-aryl-$(C_1-C_8)$-alkyl which is optionally substituted in the aryl residue, or a residue of an optionally substituted monocyclic or bicyclic, 5-membered to 12-membered heterocyclic ring, which can be aromatic, partially saturated or completely saturated, and which can contain 1, 2 or 3 identical or different ring heteroatoms selected from the group consisting of nitrogen, oxygen and sulfur;

$R^6$ is the residue of a natural or unnatural amino acid, the residue of an imino acid, the residue of an optionally N—$(C_1-C_8)$-alkylated or N—$((C_6-C_{14})$-aryl-$(C_1-C_8)$-alkylated) azamino acid where the aryl residue can optionally be substituted, or is the residue of a dipeptide, tripeptide or tetrapeptide, or is an ester or amide thereof, where functional groups can be protected by protecting groups, and where the nitrogen atoms in the amide groups in the group $R^6$—CO can carry a residue R as substituent;

$R^7$ is the residue of a 5-membered to 10-membered, saturated monocyclic or polycyclic heterocycle which is bonded via a ring nitrogen atom, which can contain one, two, three or four identical or different additional ring heteroatoms selected from the group consisting of oxygen, nitrogen and sulfur, and which can be optionally substituted at carbon atoms and at additional ring nitrogen atoms, where additional ring nitrogen atoms can carry, as substituents, identical or different residues selected from the group consisting of hydrogen, $R^h$, HCO, $R^hCO$, $R^hO$—CO, HO—CO—$(C_1$–$C_4)$-alkyl and $R^hO$—CO—$(C_1$–$C_4)$-alkyl, and $R^h$ is $(C_1$–$C_8)$-alkyl, $(C_3$–$C_8)$-cycloalkyl, $(C_3$–$C_8)$-cycloalkyl-$(C_1$–$C_8)$-alkyl, optionally substituted $(C_6$–$C_{14})$-aryl or $(C_6$–$C_{14})$-aryl-$(C_1$–$C_8)$-alkyl which is optionally substituted in the aryl residue;

$R^8$ is hydrogen, $(C_1$–$C_{10})$-alkyl, optionally substituted $(C_6$–$C_{14})$-aryl or $(C_6$–$C_{14})$-aryl-$(C_1$–$C_8)$-alkyl optionally substituted in the aryl residue, where the residues $R^8$ are independent of each other and can be identical or different;

$R^{8a}$ has, independently of $R^8$, one of the meanings of $R^8$ with the exception of hydrogen;

$R^9$ is hydrogen, aminocarbonyl, $(C_1$–$C_{10})$-alkylaminocarbonyl, $(C_3$–$C_8)$-cycloalkylaminocarbonyl, optionally substituted $(C_6$–$C_{14})$-arylaminocarbonyl, $(C_1$–$C_{10})$-alkyl, optionally substituted $(C_6$–$C_{14})$-aryl or $(C_3$–$C_8)$-cycloalkyl;

$R^{10}$ is hydroxyl, $(C_1$–$C_{10})$-alkoxy, $(C_6$–$C_{14})$-aryl-$(C_1$–$C_8)$-alkoxy optionally substituted in the aryl residue, optionally substituted $(C_6$–$C_{14})$-aryloxy, $(C_1$–$C_8)$-alkylcarbonyloxy-$(C_1$–$C_6)$-alkoxy, $(C_6$–$C_{14})$-arylcarbonyloxy-$(C_1$–$C_6)$-alkoxy which is optionally substituted in the aryl residue, $(C_6$–$C_{14})$-aryl-$(C_1$–$C_6)$-alkylcarbonyloxy-$(C_1$–$C_6)$-alkoxy which is optionally substituted in the aryl residue, $(C_1$–$C_8)$-alkoxycarbonyloxy-$(C_1$–$C_6)$-alkoxy, $(C_6$–$C_{14})$-aryloxycarbonyloxy-$(C_1$–$C_6)$-alkoxy which is optionally substituted in the aryl residue, $(C_6$–$C_{14})$-aryl-$(C_1$–$C_6)$-alkoxycarbonyloxy-$(C_1$–$C_6)$-alkoxy which is optionally substituted in the aryl residue, amino, mono- or di-$((C_1$–$C_{10})$-alkyl)amino, or $R^8R^8N$—CO—$(C_1$–$C_6)$-alkoxy in which the residues $R^8$ are independent of each other and can be identical or different;

$R^{11}$ is hydrogen, $R^{12a}$, $R^{12a}$—CO H—CO, $R^{12a}$—O—CO, $R^{12b}$—CO, $R^{12b}$—CS, $R^{12a}$—$S(O)_2$ or $R^{12b}$—$S(O)_2$;

$R^{12a}$ is $(C_1$–$C_{10})$-alkyl, $(C_2$–$C_8)$-alkenyl, $(C_2$–$C_8)$-alkynyl, $(C_3$–$C_{12})$-cycloalkyl, $(C_3$–$C_{12})$-cycloalkyl-$(C_1$–$C_8)$-alkyl, optionally substituted $(C_6$–$C_{14})$-aryl, $(C_6$–$C_{14})$-aryl-$(C_1$–$C_8)$-alkyl which is optionally substituted in the aryl residue, optionally substituted heteroaryl, heteroaryl-$(C_1$–$C_8)$-alkyl which is optionally substituted in the heteroaryl residue, or the residue $R^{15}$;

$R^{12b}$ is amino, di-$((C_1$–$C_{10})$-alkyl)amino or $R^{12a}$—NH;

$R^{13}$ is hydrogen, $(C_1$–$C_6)$-alkyl which can be optionally monosubstituted or polysubstituted by fluorine, optionally substituted $(C_6$–$C_{14})$-aryl, $(C_6$–$C_{14})$-aryl-$(C_1$–$C_6)$-alkyl which is optionally substituted in the aryl residue, $(C_3$–$C_8)$-cycloalkyl or $(C_3$–$C_8)$-cycloalkyl-$(C_1$–$C_6)$-alkyl;

$R^{15}$ is $R^{16}$—$(C_1$–$C_6)$-alkyl or is $R^{16}$;

$R^{16}$ is a 6-membered to 24-membered bicyclic or tricyclic residue which is saturated or partially unsaturated and which also can contain one, two, three or four identical or different ring heteroatoms selected from the group consisting of nitrogen, oxygen and sulfur and which also can be substituted by one or more identical or different substituents selected from the group consisting of $(C_1$–$C_4)$-alkyl and oxo;

$R^{20}$ is a direct linkage or a divalent $(C_1$–$C_6)$-alkylene residue;

$R^{21}$ is hydrogen, $(C_1$–$C_8)$-alkyl, $(C_3$–$C_{12})$-cycloalkyl, $(C_3$–$C_{12})$-cycloalkyl-$(C_1$–$C_8)$-alkyl, optionally substituted $(C_6$–$C_{14})$-aryl, $(C_6$–$C_{14})$-aryl-$(C_1$–$C_8)$-alkyl which is optionally substituted in the aryl residue, the residue Het or the residue Het-$(C_1$–$C_8)$-alkyl, in which alkyl residues can be monosubstituted or polysubstituted by fluorine, and, when the residues $R^{21}$ occur more than once, they are independent of each other and can be identical or different;

$R^{22}$ is $R^{21}$—, $R^{21}O$—, $R^{21}N(R^{21})$—, $R^{21}C(O)$—, $R^{21}O$—C(O)—, $R^{21}N(R^{21})$—C(O)—, $R^{21}N(R^{21})$—C(=N($R^{21}$))—or $R^{21}C(O)$—N($R^{21}$)—;

$R^{30}$ is one of the residues $R^{32}(R)N$—CO—N(R)—$R^{31}$, $R^{32}(R)N$—CS—N(R)—$R^{31}$, $R^{32}(R)N$—$S(O)_n$—N(R)—$R^{31}$, $R^{32}$—CO—N(R)—$R^{31}$, $R^{32}$—CS—N(R)—$R^{31}$, $R^{32}$—$S(O)_n$—N(R)—$R^{31}$, $R^{32}(R)N$—CO—$R^{31}$, $R^{32}(R)N$—CS—$R^{31}$, $R^{32}(R)N$—$S(O)_n$—$R^{31}$, $R^{32}$—CO—$R^{31}$, $R^{32}$—CS—$R^{31}$, $R^{32}$—$S(O)_n$—$R^{31}$ or $R^{12a}$—O—CO—N(R)—$R^{31}$;

$R^{31}$ is the divalent residue —$R^{33}$—$R^{34}$—$R^{35}$—$R^{36}$—, where $R^{36}$ is bonded to the nitrogen atom in the imidazolidine ring in the formula I;

$R^{32}$ is hydrogen, $(C_1$–$C_8)$-alkyl which can be optionally substituted by from 1 to 8 fluorine atoms, $(C_2$–$C_8)$-alkenyl, $(C_2$–$C_8)$-alkynyl, $(C_3$–$C_{12})$-cycloalkyl, $(C_3$–$C_{12})$-cycloalkyl-$(C_1$–$C_8)$-alkyl, $(C_6$–$C_{12})$-bicycloalkyl, $(C_6$–$C_{12})$-bicycloalkyl-$(C_1$–$C_8)$-alkyl, $(C_6$–$C_{12})$-tricycloalkyl, $(C_6$–$C_{12})$-tricycloalkyl-$(C_1$–$C_8)$-alkyl, optionally substituted $(C_6$–$C_{14})$-aryl, $(C_6$–$C_{14})$-aryl-$(C_1$–$C_8)$-alkyl which is optionally substituted in the aryl residue, optionally substituted heteroaryl or heteroaryl-$(C_1$–$C_8)$-alkyl which is optionally substituted in the heteroaryl residue;

$R^{33}$ is a direct linkage or a divalent $(C_1$–$C_6)$-alkylene residue;

$R^{34}$ is a divalent residue selected from the group consisting of $(C_1$–$C_8)$-alkylene, $(C_3$–$C_{12})$-cycloalkylene, $(C_6$–$C_{12})$-bicycloalkylene, $(C_6$–$C_{12})$-tricycloalkylene, optionally substituted $(C_6$–$C_{14})$-arylene and optionally substituted heteroarylene;

$R^{35}$ is a direct linkage or a divalent $(C_1$–$C_8)$-alkylene residue;

$R^{36}$ is a direct linkage, the group —CO— or the group —$S(O)_n$—;

Het is a residue of a monocyclic or polycyclic, 4-membered to 14-membered, aromatic or non-aromatic ring which contains 1, 2, 3 or 4 identical or different ring heteroatoms selected from the group consisting of nitrogen, oxygen and sulfur and can optionally be substituted by one or more identical or different substituents;

e and h are, independently of each other, 0 or 1;

n is 1 or 2, where, when they occur more than once, the numbers n are independent of each other and can be identical or different;

in all their stereoisomeric forms and mixtures thereof in all ratios, and their physiologically tolerated salts.

When residues or substituents can occur more than once in the compounds of the formula I, they all generally can have, independently of each other, the given meanings and be identical or different. If residues are made up of two or more components, such as, for example, arylalkyl, the free linkage via which the residue is bonded is located on the component which is specified at the right-hand end of the name, i.e., in the case of the arylalkyl residue, on the alkyl group to which an aryl group is then bonded as a substituent.

Alkyl residues can be straight-chain or branched. This also applies when they carry substituents or occur as substituents of other residues, for example, in alkoxy residues, alkoxycarbonyl residues or arylalkyl residues. Examples of suitable alkyl residues are methyl, ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, isopropyl, isobutyl, isopentyl, isohexyl, 3-methylpentyl, neopentyl, neohexyl, 2,3,5-trimethylhexyl, sec-butyl, tert-butyl and tert-pentyl. Preferred alkyl residues are selected from the group consisting of methyl, ethyl, n-propyl, isopropyl (=1-methylethyl), n-butyl, isobutyl (i.e., 2-methylpropyl), sec-butyl, tert-butyl (i.e., 1,1-dimethylethyl), n-pentyl, isopentyl, n-hexyl and isohexyl. If alkyl residues are substituted by fluorine atoms, they can then contain, for example, 1, 2, 3, 4, 5, 6 or 7 fluorine atoms, unless otherwise indicated. For example, a methyl group in a fluorine-substituted alkyl residue can be present as a trifluoromethyl group. Examples of fluorine-substituted alkyl residues are trifluoromethyl, 2-fluoroethyl, 2,2,2-trifluoroethyl and heptafluoroisopropyl.

Alkylene residues (i.e., alkanediyl residues or divalent residues which are derived from an alkane), can likewise be straight-chain or branched. They can be bonded via any desired position. Examples of alkylene residues are the divalent residues which correspond to the abovementioned monovalent residues, for example, methylene, ethylene (i.e., 1,2-ethylene or 1,1-ethylene), trimethylene (i.e., 1,3-propylene), tetramethylene (i.e., 1,4-butylene), pentamethylene, hexamethylene, or methylene or ethylene which is substituted by alkyl residues. Examples of substituted methylene are methylene groups which carry a methyl group, an ethyl group, an n-propyl group, an isopropyl group, an n-butyl group, an isobutyl group, a tert-butyl group, an n-pentyl group, an isopentyl group, an n-hexyl group or two methyl groups as substituents. Substituted ethylene can be substituted on the one or on the other carbon atom or on both carbon atoms.

Alkenyl residues and alkenylene residues (i.e., alkenediyl residues) and alkynyl residues also can be straight-chain or branched. Examples of alkenyl residues are vinyl, 1-propenyl, allyl, butenyl, 2-methyl-1-propenyl, 2-methyl-2-propenyl and 3-methyl-2-butenyl. Examples of alkenylene residues are vinylene, propenylene and butenylene. Examples of alkynyl residues are ethynyl, 1-propynyl and propargyl.

Examples of cycloalkyl residues are cyclopropyl, cyclobutyl, cyclopentyl, cyclohexyl, cycloheptyl, cyclooctyl, cyclononyl, cyclodecyl, cycloundecyl and cyclododecyl, which also can be substituted by, for example, one or more (e.g., one, two, three or four) identical or different ($C_1$–$C_4$)-alkyl residues. Examples of substituted cycloalkyl residues are 4-methylcyclohexyl and 2,3-dimethylcyclopentyl. These explanations with regard to the monovalent cycloalkyl residues apply, in a corresponding manner, to cycloalkylene residues (i.e., cycloalkanediyl residues or divalent residues which are derived from cycloalkanes). Cycloalkylene residues can be bonded via any desired positions.

Bicycloalkyl residues and tricycloalkyl residues and the 6-membered to 24-membered bicyclic and tricyclic residues which represent $R^{16}$ are formally obtained by abstracting a hydrogen atom from bicycles and tricycles, respectively. The underlying bicycles and tricycles can contain only carbon atoms as ring members, (i.e., they can be bicycloalkanes or tricycloalkanes) or they can, in the case of the residues which represent $R^{16}$, also contain one to four identical or different ring heteroatoms selected from the group consisting of nitrogen, oxygen and sulfur, i.e., they can be aza-, oxa- and thia-bicycloalkanes and -tricycloalkanes. When ring heteroatoms are present, preferably one or two ring heteroatoms, in particular nitrogen atoms or oxygen atoms, are present. The ring heteroatoms can occupy any desired positions in the bicyclic or tricyclic system; they can be present in the bridges or, in the case of nitrogen atoms, at the bridgeheads as well. Both the bicycloalkanes and tricycloalkanes and also their heteroanalogs can be completely saturated or contain one or more double bonds. Preferably, they are completely saturated or contain one or two double bonds; particularly preferably, they are completely saturated. Both the bicycloalkanes and tricycloalkanes and also the heteroanalogs, and both the saturated and the unsaturated representatives, can be unsubstituted or they can be substituted in any desired and suitable positions, by one or more oxo groups and/or one or more, for example, one, two, three or four, identical or different ($C_1$–$C_4$)-alkyl groups, for example, methyl groups and/or isopropyl groups, preferably methyl groups. The free bond of the bicyclic or tricyclic residue can be located in any arbitrary position in the molecule; the residue can consequently be bonded via a bridgehead atom or an atom in a bridge. The free bond can be located in any stereochemical position, for example, in an exo position or an endo position.

Examples of parent bicyclic ring systems from which a bicyclic residue can be derived, are norbornane (i.e., bicyclo[2.2.1]heptane), bicyclo[2.2.2]octane and bicyclo[3.2.1]octane; examples of unsaturated systems or substituted systems or systems which contain heteroatoms are 7-azabicylo[2.2.1]heptane, bicyclo[2.2.2.]oct-5-ene and camphor (i.e., 1,7,7-trimethyl-2-oxobicyclo[2.2.1]heptane).

Examples of tricyclic ring systems from which a tricyclic residue can be derived are twistane (i.e., tricyclo[4.4.0.0$^{3,8}$]decane), adamantane (i.e., tricyclo[3.3.1.1$^{3,7}$]decane), noradamantane (i.e., tricyclo[3.3.1.0$^{3,7}$]nonane), tricyclo[2.2.1.0$^{2,6}$]heptane, tricyclo[5.3.2.0$^{4,9}$]dodecane, tricyclo[5.4.0.0$^{2,9}$]undecane and tricyclo[5.5.1.0$^{3,11}$]tridecane.

Bicyclic or tricyclic residues are preferably derived from bridged bicycles and tricycles, respectively, i.e., from systems in which rings possess two or more than two atoms in common. Unless otherwise indicated, preference is furthermore given to bicyclic or tricyclic residues having from 6 to 18 ring members, with more preference being given to those having from 6 to 14 ring members, and even more preference being given to those having from 7 to 12 ring members. Specifically preferred bicyclic or tricyclic residues which can, for example, represent a bicycloalkyl group or a tricycloalkyl group, are the 2-norbornyl residue, both that having the free bond in the exo position and that having the free bond in the endo position, the 2-bicyclo[3.2.1]octyl residue, the adamantyl residue, both the 1-adamantyl residue and the 2-adamantyl residue, the homoadamantyl residue and the noradamantyl residue, for example, the 3-noradamantyl residue. Moreover preferred are the 1-adamantyl residue and the 2-adamantyl residue.

The above clarifications with regard to the monovalent bicycloalkyl residues and tricycloalkyl residues apply, in a corresponding manner, to the divalent bicycloalkylene residues and tricycloalkylene residues (=bicycloalkanediyl residues and tricycloalkanediyl residues).

Examples of $(C_6-C_{14})$-aryl groups are phenyl, naphthyl including 1-naphthyl and 2-naphthyl, biphenylyl including 2-biphenylyl, 3-biphenylyl and 4-biphenylyl, anthryl and fluorenyl; examples of $(C_6-C_{10})$-aryl groups are 1-naphthyl, 2-naphthyl and phenyl. Biphenylyl residues, naphthyl residues and, in particular, phenyl residues are preferred aryl residues. Aryl residues, in particular phenyl residues, can be unsubstituted or be substituted once or more than once, for example, once, twice, three times or four times, by identical or different residues. Substituted aryl residues, in particular phenyl residues, are preferably substituted by substituents selected from the group consisting of $(C_1-C_8)$-alkyl, in particular $(C_1-C_4)$-alkyl such as methyl; $(C_1-C_8)$-alkoxy, in particular $(C_1-C_4)$-alkoxy such as methoxy; $(C_1-C_8)$-alkoxy, in particular $(C_1-C_4)$-alkoxy, which is substituted by one or more fluorine atoms, for example, 1, 2, 3, 4 or 5 fluorine atoms, such as trifluoromethoxy; halogen; nitro; amino; trifluoromethyl; hydroxyl; hydroxy-$(C_1-C_4)$-alkyl, such as hydroxymethyl or 1-hydroxyethyl or 2-hydroxyethyl; methylenedioxy; dimethylmethylenedioxy; ethylenedioxy; formyl; acetyl; cyano; hydroxycarbonyl; aminocarbonyl; $(C_1-C_4)$-alkoxycarbonyl; phenyl; phenoxy; benzyl; benzyloxy; and tetrazolyl.

In monosubstituted phenyl residues, the substituent can be located in the 2 position, the 3 position or the 4 position. Phenyl which is substituted twice can contain the substituents in the 2,3 position, the 2,4 position, the 2,5 position, the 2,6 position, the 3,4 position or the 3,5 position. In phenyl residues which are substituted three times, the substituents can be located in the 2,3,4 position, the 2,3,5 position, the 2,4,5 position, the 2,4,6 position, the 2,3,6 position or the 3,4,5 position.

Examples of substituted phenyl residues are 2-methylphenyl, 3-methylphenyl, 4-methylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2,4,5-trimethylphenyl, 2,4,6-trimethylphenyl, 3,4,5-trimethylphenyl, 2-(n-butyl)phenyl, 3-(n-butyl)phenyl, 4-(n-butyl)phenyl, 2-isobutylphenyl, 3-isobutylphenyl, 4-isobutylphenyl, 3-tert-butylphenyl, 4-tert-butylphenyl, 2-methoxyphenyl, 3-methoxyphenyl, 4-methoxyphenyl, 2,3-dimethoxyphenyl, 2,4-dimethoxyphenyl, 2,5-dimethoxyphenyl, 2,6-dimethoxyphenyl, 3,4-dimethoxyphenyl, 3,5-dimethoxyphenyl, 2,4,5-trimethoxyphenyl, 2,4,6-trimethoxyphenyl, 3,4,5-trimethoxyphenyl, 2-(n-butoxy)phenyl, 3-(n-butoxy)phenyl, 4-(n-butoxy)phenyl, 2-isobutoxyphenyl, 3-isobutoxyphenyl, 4-isobutoxyphenyl, 2-tert-butoxyphenyl, 3-tert-butoxyphenyl, 4-tert-butoxyphenyl, 2,3-methylenedioxyphenyl, 3,4-methylenedioxyphenyl, 2,3-ethylenedioxyphenyl, 3,4-ethylenedioxyphenyl, 2-fluorophenyl, 3-fluorophenyl, 4-fluorophenyl, 2,3-difluorophenyl, 2,4-difluorophenyl, 2,5-difluorophenyl, 2,6-difluorophenyl, 3,4-difluorophenyl, 3,5-difluorophenyl, 2,4,5-trifluorophenyl, 2,4,6-trifluorophenyl, 3,4,5-trifluorophenyl, 2,3,5,6-tetrafluorophenyl, 2,3,4,5,6-pentafluorophenyl, 2-chlorophenyl, 3-chlorophenyl, 4-chlorophenyl, 2,3-dichlorophenyl, 2,4-dichlorophenyl, 2,5-dichlorophenyl, 2,6-dichlorophenyl, 3,4-dichlorophenyl, 3,5-dichlorophenyl, 2-bromophenyl, 3-bromophenyl, 4-bromophenyl, 3-iodophenyl, 4-iodophenyl, 2-trifluoromethylphenyl, 3-trifluoromethylphenyl, 4-trifluoromethylphenyl, 3,4-bis(trifluoromethyl)phenyl, 3,5-bis(trifluoromethyl)phenyl, 2-trifluoromethoxyphenyl, 3-trifluoromethoxyphenyl, 4-trifluoromethoxyphenyl, etc. However, in substituted phenyl residues just so different substituents, in any desired and suitable combination, can be present such as, for example, in the residues, 3-methoxy-4-methylphenyl, 4-fluoro-3-methoxyphenyl, 3-fluoro-4-methoxyphenyl, 3,5-difluoro-4-methoxyphenyl, 3-fluoro-4,5-methylenedioxyphenyl, 3-fluoro-4,5-ethylenedioxyphenyl, 2-chloro-3-methylphenyl, 3-chloro-4-methylphenyl, 3-chloro-4-fluorophenyl, etc.

The above explanations apply in a corresponding manner to substituted aryl residues in groups such as, for example, arylalkyl, arylcarbonyl, etc. Examples of arylalkyl residues are 1- and 2-naphthylmethyl, 2-, 3- and 4-biphenylylmethyl and 9-fluorenylmethyl and, in particular, benzyl, all of which also can be substituted. Examples of substituted arylalkyl residues are benzyl residues and naphthylmethyl residues which are substituted in the aryl moiety by one or more $(C_1-C_8)$-alkyl residues, in particular $(C_1-C_4)$-alkyl residues, for example, 2-, 3- and 4-methylbenzyl, 4-isobutylbenzyl, 4-tert-butylbenzyl, 4-octylbenzyl, 3,5-dimethylbenzyl, pentamethylbenzyl, 2-, 3-, 4-, 5-, 6-, 7- and 8-methylnaphth-1-ylmethyl, 1-, 3-, 4-, 5-, 6-, 7- and 8-methylnaphth-2-ylmethyl; benzyl residues and naphthylmethyl residues which are substituted in the aryl moiety by one or more $(C_1-C_8)$-alkoxy residues, in particular $(C_1-C_4)$-alkoxy residues, for example, 4-methoxybenzyl, 4-neopentyloxybenzyl, 3,5-dimethoxybenzyl, 2,3,4-trimethoxybenzyl; 3,4-methylenedioxybenzyl; trifluoromethoxybenzyl residues; nitrobenzyl residues, for example, 2-, 3- and 4-nitrobenzyl; halobenzyl residues, for example, 2-, 3- and 4-chloro- and 2-, 3- and 4-fluorobenzyl, 3,4-dichlorobenzyl and pentafluorobenzyl; trifluoromethylbenzyl residues, for example, 3- and 4-trifluoromethylbenzyl and 3,5-bistrifluoromethylbenzyl. However, substituted arylalkyl residues also can contain substituents which are different from each other. In general, preference is given to compounds of the formula I which do not contain more than two nitro groups in the molecule.

The above explanations with regard to the monovalent aryl residues apply, in a corresponding manner, to divalent arylene residues, i.e., divalent residues which are derived from aromatic compounds. Arylene residues can be linked via any desired positions. An example of arylene residues are phenylene residues which include 1,4-phenylene, 1,3-phenylene and 1,2-phenylene.

Phenylenealkyl is, for example, phenylenemethyl (—C$_6$H$_4$—CH$_2$—) or phenyleneethyl (for example, —C$_6$H$_4$—CH$_2$—CH$_2$—). Alkylenephenyl is, for example, methylenephenyl (—CH$_2$—C$_6$H$_4$—). Phenylenealkenyl is, for example, phenyleneethenyl or phenylenepropenyl.

Heteroaryl represents a residue of a monocyclic or polycyclic aromatic system which has from 5 to 14 ring members and which contains 1, 2, 3, 4 or 5 heteroatoms as ring members. Examples of ring heteroatoms are nitrogen, oxygen and sulfur. When several heteroatoms are present, they can be identical or different. Heteroaryl residues can be unsubstituted or monosubstituted or polysubstituted, for example, substituted once, twice or three times by identical or different substituents selected from the group consisting of (C$_1$–C$_8$)-alkyl, in particular (C$_1$–C$_4$)-alkyl; (C$_1$–C$_8$)-alkoxy, in particular (C$_1$–C$_4$)-alkoxy; (C$_1$–C$_8$)-alkoxy, in particular (C$_1$–C$_4$)-alkoxy which is substituted by one or more, for example, 1, 2, 3, 4 or 5, fluorine atoms; halogen; nitro; amino; trifluoromethyl; hydroxyl; hydroxy-(C$_1$–C$_4$)-alkyl such as hydroxymethyl or 1-hydroxyethyl or 2-hydroxyethyl; methylenedioxy; dimethylmethylenedioxy; ethylenedioxy; formyl; acetyl; cyano; hydroxycarbonyl; aminocarbonyl; (C$_1$–C$_4$)-alkoxycarbonyl; phenyl; phenoxy; benzyl; benzyloxy; and tetrazolyl. Heteroaryl preferably represents a monocyclic or bicyclic aromatic residue which contains 1, 2, 3 or 4, in particular 1, 2 or 3, identical or different ring heteroatoms selected from the group consisting of nitrogen, oxygen and sulfur and which can be substituted by 1, 2, 3 or 4, in particular 1, 2 or 3, identical or different substituents selected from the group consisting of (C$_1$–C$_6$)-alkyl, (C$_1$–C$_6$)-alkoxy, fluorine, chlorine, nitro, amino, trifluoromethyl, hydroxyl, hydroxy-(C$_1$–C$_4$)-alkyl, (C$_1$–C$_4$)-alkoxycarbonyl, phenyl, phenoxy, benzyloxy, and benzyl. Particularly preferably, heteroaryl represents a monocyclic or bicyclic aromatic residue having from 5 to 10 ring members, and in particular represents a 5-membered to 6-membered monocyclic aromatic residue which contains 1, 2 or 3, in particular 1 or 2, identical or different ring heteroatoms selected from the group consisting of nitrogen, oxygen and sulfur and which can be substituted by 1 or 2 identical or different substituents selected from the group consisting of (C$_1$–C$_4$)-alkyl, (C$_1$–C$_4$)-alkoxy, phenyl, phenoxy, benzyloxy, and benzyl.

Heterocycles which represent monocyclic or bicyclic 5-membered to 12-membered heterocyclic rings can be aromatic or partially saturated or completely saturated. They can be unsubstituted or substituted, at one or more carbon atoms or at one or more nitrogen atoms, by identical or different substituents as specified for the residue heteroaryl. In particular, the heterocyclic ring can be monosubstituted or polysubstituted, for example, substituted once, twice, three times or four times, on carbon atoms by identical or different residues selected from the group consisting of (C$_1$–C$_8$)-alkyl, for example, (C$_1$–C$_4$)-alkyl, (C$_1$–C$_8$)-alkoxy, for example, (C$_1$–C$_4$)-alkoxy such as methoxy, phenyl-(C$_1$–C$_4$)-alkoxy, for example, benzyloxy, hydroxyl, oxo, halogen, nitro, amino and trifluoromethyl, and/or ring nitrogen atoms in heterocyclic rings as well as in heteroaryl residues can be substituted by (C$_1$–C$_8$)-alkyl, for example, (C$_1$–C$_4$)-alkyl such as methyl or ethyl, or by optionally substituted phenyl or phenyl-(C$_1$–C$_4$)-alkyl such as, for example, benzyl.

The group Het encompasses aromatic heterocycles and consequently also groups representing heteroaryl insofar as these groups come within the definition of Het with regard to the number of the ring members and heteroatoms. Het additionally also encompasses non-aromatic heterocycles which are completely saturated or which contain one or more double bonds in the ring system. Het can be substituted on nitrogen atoms and/or carbon atoms by one or more (e.g., 1, 2, 3 or 4) identical or different substituents, for example, by (C$_1$–C$_8$)-alkyl, in particular (C$_1$–C$_4$)-alkyl, (C$_3$–C$_{12}$)-cycloalkyl, (C$_3$–C$_{12}$)-cycloalkyl-(C$_1$–C$_8$)-alkyl, optionally substituted (C$_6$–C$_{14}$)-aryl, (C$_6$–C$_{14}$)-aryl-(C$_1$–C$_8$)-alkyl which is optionally substituted in the aryl residue, heteroaryl, heteroaryl-(C$_1$–C$_8$)-alkyl, (C$_1$–C$_8$)-alkoxy, in particular (C$_1$–C$_4$)-alkoxy, optionally substituted phenoxy, benzyloxy, halogen, nitro, amino, (C$_1$–C$_8$)-alkylamino, di-((C$_1$–C$_8$)-alkyl)amino, trifluoromethyl, hydroxyl, methylenedioxy, dimethylmethylenedioxy, ethylenedioxy, cyano, hydroxycarbonyl, aminocarbonyl, (C$_1$–C$_4$)-alkoxycarbonyl and ester groups in general, acyl groups, oxo (i.e., doubly bonded oxygen atom) and thioxo (=doubly bonded sulfur atom), where alkyl residues can be monosubstituted or polysubstituted by fluorine.

Examples of parent compounds of heterocycles, from which a heteroaryl residue, a residue Het, a residue of a monocyclic or bicyclic 5-membered to 12-membered heterocyclic ring, a divalent residue of a 5-membered or 6-membered heterocycle, a heterocyclic residue representing R$^7$, or a heterocyclic residue representing R$^{16}$, can be derived are, insofar as they come within the respective definition in the particular case, pyrrole, furan, thiophene, imidazole, pyrazole, oxazole, isoxazole, thiazole, isothiazole, tetrazole, pyridine, pyrazine, pyrimidine, pyridazine, indole, isoindole, indazole, phthalazine, quinoline, isoquinoline, quinoxaline, quinazoline, cinnoline and β-carboline and benzo-fused, cyclopenta-, cyclohexa- or cyclohepta-fused derivatives of these heterocycles. In a general manner, nitrogen heterocycles also can be present as N-oxides or as quaternary salts.

Examples of heterocyclic residues which can, for example, represent heteroaryl or the residue of a monocyclic or bicyclic 5-membered to 12-membered heterocyclic ring, insofar as they come within the respective definition in the particular case, are 2- or 3-pyrrolyl, phenylpyrrolyl, for example, 4- or 5-phenyl-2-pyrrolyl, 2- or 3-furyl, 2- or 3-thienyl, 4-imidazolyl, methylimidazolyl, for example, 1-methyl-2-, -4- or -5-imidazolyl, 1,3-thiazol-2-yl, pyridyl, 2-pyridyl, 3-pyridyl, 4-pyridyl, 2-, 3- or 4-pyridyl-N-oxide, 2-pyrazinyl, 2-, 4- or 5-pyrimidinyl, indolyl, 2-, 3- or 5-indolyl, substituted 2-indolyl, for example, 1-methyl-, 5-methyl-, 5-methoxy-, 5-benzyloxy-, 5-chloro- or 4,5-dimethyl-2-indolyl, 1-benzyl-2- or -3-indolyl, 4,5,6,7-tetrahydro-2-indolyl, cyclohepta[b](5-pyrrolyl), 2-, 3- or 4-quinolyl, 1-, 3- or 4-isoquinolyl, 1-oxo-1,2-dihydroisoquinol-3-yl, 2-quinoxalinyl, 2-benzofuranyl, 2-benzothienyl, 2-benzoxazolyl and 2-benzothiazolyl. Examples of residues of partially saturated or completely saturated heterocyclic rings are dihydropyridinyl, pyrrolidinyl, for example, 2- or 3-(N-methylpyrrolidinyl), piperazinyl, morpholinyl, thiomorpholinyl, tetrahydrothienyl and benzodioxolanyl.

The explanations with regard to the monovalent heterocyclic residues including heteroaryl residues apply in a corresponding manner to divalent heterocyclic residues, for example, heteroarylene residues (i.e., divalent residues which are derived from heteroaromatic compounds).

Heterocyclic residues which represent the residue $R^7$ can be unsubstituted or monosubstituted or polysubstituted (e.g., substituted once, twice, three times, four times or five times) on the carbon atoms and/or on additional ring nitrogen atoms by identical or different substituents. Carbon atoms can be substituted, for example, by $(C_1-C_8)$-alkyl, in particular $(C_1-C_4)$-alkyl, $(C_1-C_8)$-alkoxy, in particular $(C_1-C_4)$-alkoxy, halogen, nitro, amino, trifluoromethyl, hydroxyl, oxo, cyano, hydroxycarbonyl, aminocarbonyl, $(C_1-C_4)$-alkoxycarbonyl, phenyl, phenoxy, benzyl, benzyloxy or tetrazolyl, in particular by $(C_1-C_4)$-alkyl, for example, methyl, ethyl or tert-butyl, $(C_1-C_4)$-alkoxy, for example, methoxy, hydroxyl, oxo, phenyl, phenoxy, benzyl, or benzyloxy. Sulfur atoms can be oxidized to the sulfoxide or to the sulfone. Examples of such residues $R^7$ which are bonded by way of a ring nitrogen atom are 1-pyrrolidinyl, 1-piperidinyl, 1-piperazinyl, 4-substituted 1-piperazinyl, 4-morpholinyl, 4-thiomorpholinyl, 1-oxo-4-thiomorpholinyl, 1,1-dioxo-4-thiomorpholinyl, perhydroazepin-1-yl, 2,6-dimethyl-1-piperidinyl, 3,3-dimethyl-4-morpholinyl, 4-isopropyl-2,2,6,6-tetramethyl-1-piperazinyl, 4-acetyl-1-piperazinyl and 4-ethoxycarbonyl-1-piperazinyl.

Halogen represents fluorine, chlorine, bromine or iodine, in particular fluorine or chlorine.

In one embodiment of the invention, the substituent on a substituted alkylene residue or alkenylene residue representing B contains a cyclic moiety as is the case when the substituent is selected from the group consisting of $(C_3-C_{10})$-cycloalkyl, $(C_3-C_{10})$-cycloalkyl-$(C_1-C_6)$-alkyl, optionally substituted $(C_6-C_{14})$-aryl, $(C_6-C_{14})$-aryl-$(C_1-C_6)$-alkyl which is optionally substituted in the aryl residue, optionally substituted heteroaryl and heteroaryl-$(C_1-C_6)$ which is optionally substituted in the heteroaryl residue. In another embodiment of the invention, the substituent on a substituted alkylene residue or alkenylene residue representing B is acyclic as is the case when the substituent is selected from the group consisting of $(C_1-C_8)$-alkyl, $(C_2-C_8)$-alkenyl and $(C_2-C_8)$-alkynyl. The acyclic substituents can contain 2, 3, 4, 5, 6, 7 or 8 carbon atoms, and, in the case of a saturated alkyl substituent, 1 carbon atom as well. In the case of the alkenyl substituents and alkynyl substituents, the double bond or triple bond can be located in any desired position and, in the case of the double bond, have the cis configuration or the trans configuration. As explained above, these alkyl residues, alkenyl residues and alkynyl residues can be straight-chain or branched.

Examples of substituents which can be carried by the $(C_1-C_6)$-alkylene residue or $(C_2-C_6)$-alkenylene residue representing B are in particular methyl, ethyl, n-propyl, n-butyl, n-pentyl, n-hexyl, n-heptyl, n-octyl, isopropyl, isobutyl, isopentyl, isohexyl, sec-butyl, tert-butyl, tert-pentyl, neopentyl, neohexyl, 3-methylpentyl, 2-ethylbutyl, vinyl, allyl, 1-propenyl, 2-butenyl, 3-butenyl, 3-methyl-2-butenyl, ethynyl, 1-propynyl, 2-propynyl, 6-hexynyl, phenyl, benzyl, 1-phenylethyl, 2-phenylethyl, 3-phenylpropyl, 4-biphenylylmethyl, cyclopropyl, cyclopropylmethyl, cyclobutyl, cyclobutylmethyl, cyclopentyl, cyclopentylmethyl, cyclohexyl, cyclohexylmethyl, 2-cyclohexylethyl, 3-cyclooctylpropyl, 2-pyridyl, 3-pyridyl, 4-pyridyl, 2-pyridylmethyl, 3-pyridylmethyl, 4-pyridylmethyl, 2-(4-pyridyl)ethyl, 2-furylmethyl, 3-furylmethyl, 2-thienylmethyl, 3-thienylmethyl and 2-(3-indolyl)ethyl.

The residue of an amino acid, imino acid, azamino acid, dipeptide, tripeptide or tetrapeptide representing $R^6$ is obtained, as is customary in peptide chemistry, from the corresponding amino acid, imino acid, azamino acid, dipeptide, tripeptide or tetrapeptide by formally removing a hydrogen atom from an amino group, for example, the N-terminal amino group, or from the imino group. This group is then linked via the resulting free bond on the amino group or the imino group, by means of an amide bond, in the manner of a peptide, to the CO group in the $R^6$—CO group.

The natural and unnatural amino acids can be present in all the stereochemical forms, for example, in the D form or the L form or in the form of a mixture of stereoisomers, for example, in the form of a racemate. Preferred amino acids are α-amino acids and β-amino acids, with α-amino acids being particularly preferred. Suitable amino acids which may be mentioned, by way of example, are (cf. Houben-Weyl, Methoden der organischen Chemie [Methods of organic chemistry], Volumes 15/1 and 15/2, Georg Thieme Verlag, Stuttgart, 1974):

Aad, Abu, γAbu, ABz, 2ABz, εAca, Ach, Acp, Adpd, Ahb, Aib, βAib, Ala, βAla, ΔAla, Alg, All, Ama, Amt, Ape, Apm, Apr, Arg, Asn, Asp, Asu, Aze, Azi, Bai, Bph, Can, Cit, Cys, (Cys)$_2$, Cyta, Daad, Dab, Dadd, Dap, Dapm, Dasu, Djen, Dpa, Dtc, Fel, Gln, Glu, Gly, Guv, hAla, hArg, hcys, hGln, hGlu, His, hIle, hLeu, hLys, hMet, hphe, hPro, hSer, hThr, hTrp, hTyr, Hyl, Hyp, 3Hyp, Ile, Ise, Iva, Kyn, Lant, Lcn, Leu, Lsg, Lys, βLys, ΔLys, Met, Mim, Min, nArg, NIe, Nva, Oly, Orn, Pan, Pec, Pen, Phe, Phg, Pic, Pro, ΔPro, Pse, Pya, Pyr, Pza, Qin, Ros, Sar, Sec, Sem, Ser, Thi, βThi, Thr, Thy, Thx, Tia, Tie, Tly, Trp, Trta, Tyr, Val, tert-butylglycine (Tbg), neopentylglycine (Npg), cyclohexylglycine (Chg), cyclohexylalanine (Cha), 2-thienylalanine (Thia), 2,2-diphenylaminoacetic acid, 2-(p-tolyl)-2-phenylaminoacetic acid and 2-(p-chlorophenyl)aminoacetic acid.

When $R^6$ represents the residue of a natural or unnatural α-amino acid, this residue can then, for example, correspond to the formula —N(R)—CH(SC)—CO-AG, in which CO-AG represents the acid group of the amino acid or a derivative thereof, (e.g., an ester group, an amide group or a group containing a peptide residue), and SC represents the side chain of the α-amino acid (e.g., represents a substituent which is present in the α-position in one of the above-listed α-amino acids). Examples of side chains are alkyl residues, for example, the methyl group in alanine or the isopropyl group in valine, the benzyl residue in phenylalanine, the phenyl residue in phenylglycine, the 4-aminobutyl residue in lysine or the hydroxycarbonylmethyl group in aspartic acid. As well as on the basis of structural features, the side chains, and thus the underling amino acids, also can be grouped on the basis, for example, of their physicochemical properties. For example, lipophilic side chains can be distinguished from hydrophilic side chains which latter contain polar groups, and the side chains and the amino acids be grouped accordingly. Examples of lipophilic side chains which can be present in amino acids representing $R^6$ are alkyl residues, arylalkyl residues and aryl residues. The same applies, in a corresponding manner, to amino acids which are part of a dipeptide, tripeptide or tetrapeptide residue representing $R^6$.

Azamino acids are natural or unnatural amino acids in which a CH unit has been replaced with a nitrogen atom such as is, for example, in α-amino acids the replacement of the central building block

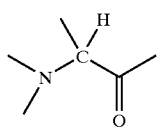  with  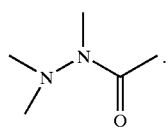

Suitable residues of imino acids include residues of the following heterocyclic compounds whose preparation is described in the literature: pyrrolidine-2-carboxylic acid; piperidine-2-carboxylic acid; 1,2,3,4-tetrahydroisoquinoline-3-carboxylic acid; decahydroisoquinoli ne-3-carboxylic acid; octahydroindole-2-carboxylic acid; decahydroquinoline-2-carboxylic acid; octahydrocyclopenta[b]pyrrole-2-carboxylic acid; 2-azabicyclo[2.2.2]octane-3-carboxylic acid; 2-azabicyclo[2.2.1]heptane-3-carboxylic acid; 2-azabicyclo[3.1.0]hexane-3-carboxylic acid; 2-azaspiro[4.4]nonane-3-carboxylic acid; 2-azaspiro[4.5]decane-3-carboxylic acid; spiro(bicyclo[2.2.1]heptane)-2,3-pyrrolidine-5-carboxylic acid; spiro(bicyclo[2.2.2]octane)-2,3-pyrrolidine-5-carboxylic acid; 2-azatricyclo[4.3.0.1$^{6,9}$]decane-3-carboxylic acid; decahydrocyclohepta[b]pyrrole-2-carboxylic acid; decahydrocycloocta[c]pyrrole-2-carboxylic acid; octahydrocyclopenta[c]pyrrole-2-carboxylic acid; octahydroisoindole-1-carboxylic acid; 2,3,3a,4,6a-hexahydrocyclopenta[b]pyrrole-2-carboxylic acid; 2,3,3a,4,5,7a-hexahydroindole-2-carboxylic acid; tetrahydrothiazole-4-carboxylic acid; isoxazolidine-3-carboxylic acid; pyrazolidine-3-carboxylic acid; and hydroxypyrrolidine-2-carboxylic acid, all of which can be optionally substituted, specifically the residues which are depicted in the following formulae:

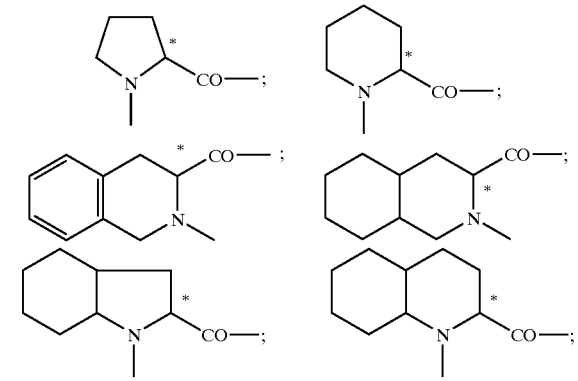

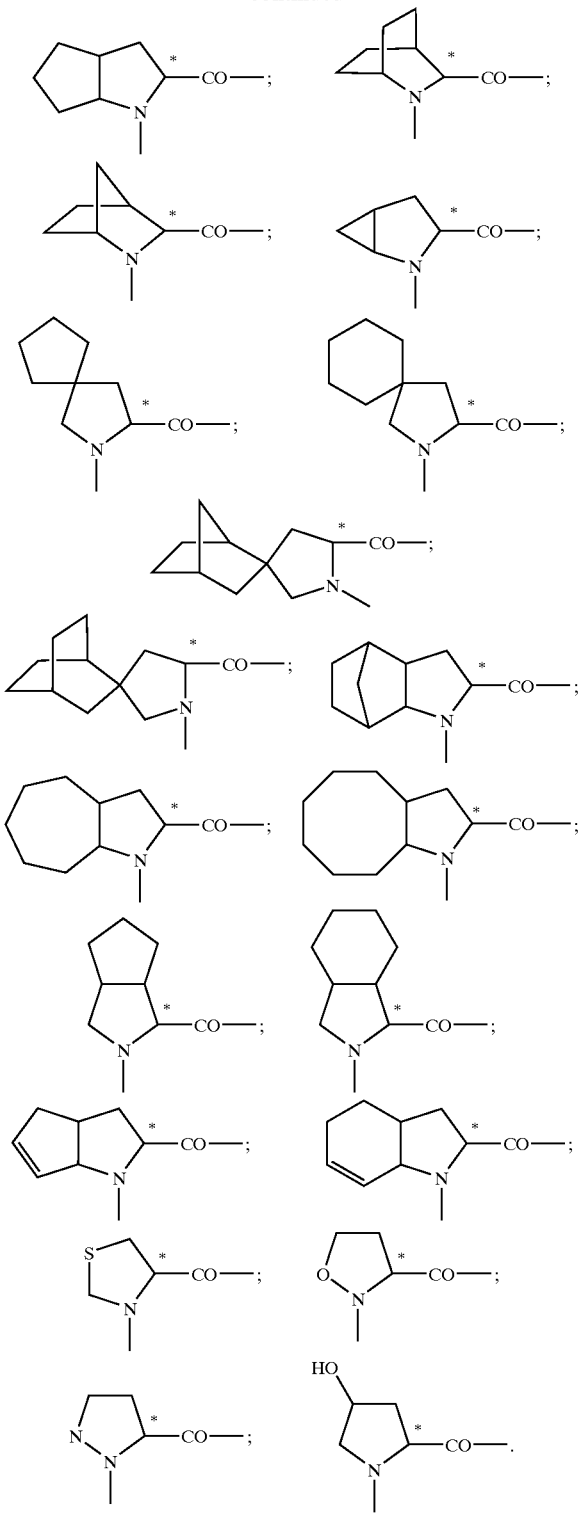

Dipeptides, tripeptides and tetrapeptides can contain natural or unnatural amino acids or azamino acids as building blocks. The natural or unnatural amino acids, imino acids, azamino acids, dipeptides, tripeptides and tetrapeptides can, in a general manner, also be present in the form of derivatives of the carboxylic acid group, for example, as an ester or amide (e.g., as $(C_1-C_4)$-alkyl ester, such as methyl ester, ethyl ester, n-propyl ester, isopropyl ester, isobutyl ester or tert-butyl ester, benzyl ester, unsubstituted amide, N—$(C_1-C_4)$-alkylamide, such as methylamide or ethylamide, semicarbazide or ω-amino-$(C_2-C_8)$-alkylamide).

Functional groups in the residues of amino acids, imino acids, azamino acids, dipeptides, tripeptides and tetrapeptides, and also in other parts of the compounds of formula I, can be present in protected form. Suitable protecting groups, such as urethane protecting groups, carboxyl protecting groups and side chain protecting groups, are described in Hubbuch, Kontakte (Merck) 1979, No. 3, pages 14 to 23, and in Bollesbach, Kontakte (Merck) 1980, No. 1, pages 23 to 35. The following may be mentioned, in particular: Aloc, Pyoc, Fmoc, Tcboc, Z, Boc, Ddz, Bpoc, Adoc, Msc, Moc, $Z(NO_2)$, $Z(Hal_n)$, Bobz, Iboc, Adpoc, Mboc, Acm, tert-Butyl, OBzl, ONbzl, OMbzl, Bzl, Mob, Pic, Trt.

Physiologically tolerated salts of the compounds of the formula I are, in particular, pharmaceutically utilizable salts or nontoxic salts. Compounds of the formula I which contain acid groups such as carboxylic acid groups can be present, for example, as alkali metal salts or alkaline earth metal salts, such as sodium salts, potassium salts, magnesium salts and calcium salts, or as ammonium salts, such as salts with physiologically tolerated quaternary ammonium ions and acid addition salts with ammonia and physiologically tolerated organic amines, such as methylamine, ethylamine, triethylamine, 2-hydroxyethylamine, tris(2-hydroxyethyl) amine, α,α,α-tris(hydroxymethyl)methylamine (tromethamine) or amino acids, in particular basic amino acids. Salts composed of an acid compound of the formula I and an organic amine can contain the two components in the ratio 1:1 or approximately 1:1 or else in another ratio, for example, in a ratio of from approximately 1:0.5 to approximately 1:4 (1 molecule of the formula I per 0.5 to 4 molecules of the amine), in particular in a ratio of from approximately 1:0.5 to approximately 1:2 (1 molecule of the formula I per 0.5 to 2 molecules of the amine).

Compounds of formula I, which contain basic groups (e.g., an amino group, amidino group, guanidino group or pyridyl group) can be present, for example, as salts with inorganic acids, such as hydrochloric acid, sulfuric acid or phosphoric acid, or with organic carboxylic acids or sulfonic acids, such as acetic acid, citric acid, benzoic acid, maleic acid, fumaric acid, tartaric acid, methanesulfonic acid or p-toluenesulfonic acid. Compounds which contain both acid groups and basic groups also can be present in the form of inner salts, zwitterions or betaines, which are likewise encompassed by the present invention.

Salts can be obtained from compounds of the formula I using customary methods which are known to skilled persons, for example, by combining a compound of the formula I with an organic or inorganic acid or base in a solvent or diluent, or just so from other salts by means of anion exchange or cation exchange. The present invention also encompasses salts of compounds of the formula I which are not directly suitable for use as pharmaceuticals on account of lower physiological tolerability but which can be used, for example, as intermediates for chemical reactions or for preparing physiologically tolerated salts.

Compounds of the formula I can be present in stereoisomeric forms. When the compounds of the formula I contain one or more centers of asymmetry, the S configuration or the R configuration, or an RS mixture, can be present, independent of each other, at each of the asymmetric centers. The invention includes all the possible stereoisomers of the compounds of the formula I, for example enantiomers and diastereomers, and mixtures of two or more stereoisomeric forms, for example, mixtures of enantiomers and/or diastereomers, in all ratios. The invention thus relates to enantiomers in enantiomerically pure form or substantially enantiomerically pure form, the levorotatory antipode as well as the dextrorotatory antipode, and to enantiomers in the form of racemates and in the form of mixtures of the two enantiomers in any ratio. The invention likewise relates to diastereomers in diastereomerically pure form or substantially diastereomerically pure form and in the form of mixtures in any ratio. When a cis/trans isomerism is present, the invention relates both to the cis form and to the trans form and to mixtures of these forms in all ratios. If desired, individual stereoisomers can be prepared by using stereochemically homogeneous starting substances in the synthesis, by means of stereoselective synthesis, or by separation of a mixture using customary methods, for example, by means of chromatography or crystallization including chromatography on chiral phases in the case of a separation of enantiomers. Where appropriate, a derivatization can take place before stereoisomers are separated. A stereoisomeric mixture can be separated at the level of the compounds of the formula I or at the level of a starting substance or of an intermediate during the course of the synthesis.

The compounds of the formula I according to the invention can contain mobile hydrogen atoms, i.e., be present in various tautomeric forms. The present invention relates to all the tautomers of the compounds of the formula I. The present invention furthermore encompasses derivatives of compounds of the formula I, for example, solvates, such as hydrates and adducts with alcohols, esters, prodrugs and other physiologically tolerated derivatives of compounds of the formula I, and also active metabolites of compounds of the formula I. The invention relates, in particular, to prodrugs of the compounds of the formula I which are not necessarily pharmacologically active in vitro but which are converted in vivo, under physiological conditions, into active compounds of the formula I. The skilled person is familiar with suitable prodrugs for the compounds of the formula I, i.e., chemically modified derivatives of the compounds of the formula I possessing properties which have been improved in a desired manner. Further details with regard to prodrugs can be found, for example, in Fleisher et al., *Advanced Drug Delivery Reviews,* 19 (1996) 115–130; Design of Prodrugs, H. Bundgaard, Ed., Elsevier, 1985; or H. Bundgaard, *Drugs of the Future* 16 (1991) 443. Prodrugs, which are especially suitable for the compounds of the formula I, are ester prodrugs of carboxylic acid groups, amide prodrugs of carboxylic acid groups and alcohol prodrugs of carboxylic acid groups, as well as acyl prodrugs and carbamate prodrugs of acylatable nitrogen-containing groups, such as amino groups, amidino groups and guanidino groups. In the acyl prodrugs or carbamate prodrugs, a hydrogen atom which is located on a nitrogen atom is replaced with an acyl group or carbamate group. Suitable acyl groups and carbamate groups for the acyl prodrugs and carbamate prodrugs are, for example, the groups $R^P$—CO and $R^{Pa}$O—CO, in which $R^P$ is hydrogen, $(C_1-C_{18})$-alkyl, $(C_3-C_{12})$-cycloalkyl, $(C_3-C_{12})$-cycloalkyl-$(C_1-C_8)$-alkyl, $(C_6-C_{14})$-aryl, $(C_6-C_{14})$-aryl-$(C_1-C_8)$-alkyl, heteroaryl or heteroaryl-$(C_1-C_8)$-alkyl, and $R^{Pa}$ has the meanings given for $R^P$ with the exception of hydrogen. Thus, for example, the compounds of the formula I in which the group E is hydroxymethyl, alkoxymethyl or formyl, and which exhibit a VLA-4 antagonism in vivo, are prodrugs of the compounds of the formula I in which the group E is hydroxycarbonyl. Examples of ester prodrugs and amide prodrugs are $(C_1-C_4)$-alkyl esters (e.g., methyl esters, ethyl esters, n-propyl esters, isopropyl esters, n-butyl esters and isobutyl esters, substituted alkyl esters (e.g., hydroxyalkyl esters, acyloxyalkyl esters, aminoalkyl esters, acylaminoalkyl esters and dialkylaminoalkyl esters), unsubstituted amides and N—$(C_1-C_4)$-alkylamides (e.g., methylamides or ethylamides).

The individual structural elements in the compounds of the formula I preferably have the following meanings, which each can have independently. Residues, which occur more than once, can possess the meanings independently of each other and can be identical or different.

W is preferably a divalent residue selected from the group consisting of $R^1$-A-C($R^{13}$) and

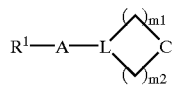

in which the ring systems

can contain one or two identical or different ring heteroatoms selected from the group consisting of nitrogen and oxygen, can be saturated or monounsaturated, and can be substituted by 1 or 2 identical or different $R^{13}$ substituents and/or can contain one or two oxo substituents, and in which L is C($R^{13}$) or N, and in which m1 and m2, independently of each other, are 0, 1, 2, 3 or 4, but the sum m1+m2 is 1, 2, 3 or 4, in particular one of the numbers 1, 3 and 4. More preferably, W is the divalent residue $R^1$-A-C($R^{13}$) in which $R^{13}$ has the abovementioned meanings. Most preferably, W is the divalent residue $R^1$-A-C($R^{13}$) in which $R^{13}$ has the abovementioned meanings but is different from hydrogen. Examples of specific W groups of this type are the divalent residues di-(($C_1-C_4$)-alkyl)methylene (i e., (($C_1-C_4$)-alkyl)$_2$ C<), e.g., dimethylmethylene or bis(trifluoromethyl) methylene (i.e., $(CH_3)_2$C< or $(CF_3)_2$C<), or (methyl)(phenyl)methylene (i.e., $(CH_3)(C_6H_5)$C<).

A subgroup of compounds in which W is the residue

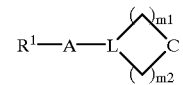

is formed by compounds in which W represents the carbocyclic groups of the formula $(CH_2)_{m3}$C<, which are optionally substituted as specified and in which the number m3, (i.e., the number of methylene groups in the polymethylene chain which is bonded to the spiro carbon atom C<by way of its terminal groups) is 2, 3, 4, 5 or 6. Examples of specific W groups of this type are the divalent residues 1,1-cyclopropylidene (i.e., dimethylenemethylene), 1,1-cyclopentylidene (i.e., tetramethylenemethylene) and 1,1-cyclohexylidene (i.e., pentamethylenemethylene), that is the residues

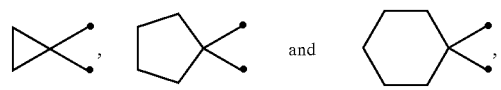

in which the free bonds are symbolized by the lines having a dot at the end, with the residues which are derived from the 5-membered ring and from the 6-membered ring being able to carry a doubly bonded oxygen atom as substituent. Altogether, compounds of formula I in which W has a meaning other than $CH_2$ form a group of preferred compounds.

Y is preferably a carbonyl group or thiocarbonyl group, and more preferably a carbonyl group.

A is preferably a direct linkage, one of the divalent residues $(C_1-C_6)$-alkylene (e.g., $(C_1-C_4)$-alkylene), $(C_5-C_6)$-cycloalkylene, phenylene, phenylene-$(C_1-C_4)$-alkyl (e.g., phenylene-$(C_1-C_2)$-alkyl), or is a divalent residue of a 5-membered or 6-membered saturated or unsaturated heterocycle which can contain one or two nitrogen atoms and which can be substituted once or twice by $(C_1-C_6)$-alkyl and/or oxo and/or thioxo. More preferably, A is a direct linkage or one of the divalent residues $(C_1-C_4)$-alkylene, phenylene and phenylene-$(C_1-C_2)$-alkyl. When W is the residue $R^1$-A-C($R^{13}$), a series of preferred residues $R^1$-A- is then formed from the residues $(C_1-C_4)$-alkyl, optionally substituted phenyl and phenyl-$(C_1-C_2)$-alkyl which is optionally substituted in the phenyl residue, in particular from the residues $(C_1-C_4)$-alkyl and optionally substituted phenyl, with it being possible for the $(C_1-C_4)$-alkyl residue to be substituted by one or more fluorine atoms and, for example, to be a methyl residue or a trifluoromethyl residue.

B is preferably a divalent methylene residue $(CH_2)$ or 1,2-ethylene residue ($CH_2$—$CH_2$), where the methylene residue and the ethylene residue are unsubstituted or substituted by one or more identical or different residues selected from the group consisting of $(C_1-C_8)$-alkyl, in particular $(C_1-C_6)$-alkyl, $(C_2-C_8)$-alkenyl, $(C_2-C_8)$-alkynyl, $(C_3-C_{10})$-cycloalkyl, in particular $(C_3-C_6)$-cycloalkyl, $(C_3-C_{10})$-cycloalkyl-$(C_1-C_6)$-alkyl, in particular $(C_3-C_6)$-cycloalkyl-$(C_1-C_6)$-alkyl, optionally substituted $(C_6-C_{14})$-aryl, in particular optionally substituted $(C_6-C_{10})$-aryl, ($C_6$–$C_{14}$)-aryl-($C_1$–$C_6$)-alkyl which is optionally substituted in the aryl residue, in particular ($C_6$–$C_{10}$)-aryl-($C_1$–$C_6$)-alkyl which is optionally substituted in the aryl residue, optionally substituted heteroaryl and heteroaryl-($C_1$–$C_6$)-alkyl which is optionally substituted in the heteroaryl residue. B is particularly preferably a methylene residue or ethylene residue which is substituted as described before, in particular a methylene residue which is substituted as described before. If an alkylene residue or alkenylene residue representing B is monosubstituted or polysubstituted, it is preferably substituted one, twice or three times, more preferably once or twice, most preferably once. If a methylene residue or ethylene residue representing B is substituted, it is preferably substituted by one or two identical or different substituents, in particular one substituent, selected from the group consisting of ($C_1$–$C_8$)-alkyl, that is straight-chain or branched alkyl having 1, 2, 3, 4, 5, 6, 7 or 8 carbon atoms, in particular ($C_1$–$C_6$)-alkyl, and ($C_3$–$C_6$)-cycloalkyl-($C_1$–$C_4$)-alkyl, in particular ($C_3$–$C_6$)-cycloalkyl-($C_1$–$C_2$)-alkyl.

E is preferably tetrazolyl, $R^6CO$, $R^7CO$, $R^{10}CO$, HCO, $R^8O$—$CH_2$, $R^8CO$—O—$CH_2$ or $(R^8O)_2P(O)$—O—$CH_2$, more preferably tetrazolyl, $R^{10}CO$, $R^8O$—$CH_2$, $R^8CO$—O—$CH_2$ or $(R^8O)_2P(O)$—O—$CH_2$, even more preferably $R^{10}CO$, $R^8O$—$CH_2$ or $R^8CO$—O—$CH_2$. A residue $R^8O$—$CH_2$ representing the group E is preferably the hydroxymethyl residue HO—$CH_2$. Most preferably, E is $R^{10}CO$, HO—$CH_2$ or $R^8CO$—O—$CH_2$, in particular $R^{10}CO$.

The residues R are preferably, independently of each other, hydrogen or ($C_1$–$C_8$)-alkyl, more preferably hydrogen, methyl or ethyl.

$R^2$ is preferably hydrogen or ($C_1$–$C_8$)-alkyl, in particular hydrogen or ($C_1$–$C_6$)-alkyl, more preferably hydrogen, methyl or ethyl.

$R^3$ is preferably hydrogen, ($C_1$–$C_8$)-alkyl which can be optionally substituted by from 1 to 8 fluorine atoms, optionally substituted ($C_6$–$C_{12}$)-aryl, ($C_6$–$C_{12}$)-aryl-($C_1$–$C_6$)-alkyl which is optionally substituted in the aryl residue, optionally substituted heteroaryl, heteroaryl-($C_1$–$C_6$)-alkyl which is optionally substituted in the heteroaryl residue, ($C_3$–$C_8$)-cycloalkyl, ($C_3$–$C_8$)-cycloalkyl-($C_1$–$C_6$)-alkyl, ($C_6$–$C_{12}$)-bicycloalkyl, ($C_6$–$C_{12}$)-bicycloalkyl-($C_1$–$C_6$)-alkyl, ($C_6$–$C_{12}$)-tricycloalkyl, ($C_6$–$C_{12}$)-tricycloalkyl-($C_1$–$C_6$)-alkyl, ($C_2$–$C_8$)-alkenyl, ($C_2$–$C_8$)-alkynyl or $R^{11}NH$. More preferably, $R^3$ is hydrogen, ($C_1$–$C_8$)-alkyl which can be optionally substituted by from 1 to 8 fluorine atoms, optionally substituted ($C_6$–$C_{12}$)-aryl, ($C_6$–$C_{12}$)-aryl-($C_1$–$C_6$)-alkyl which is optionally substituted in the aryl residue, optionally substituted heteroaryl, heteroaryl-($C_1$–$C_6$)-alkyl which is optionally substituted in the heteroaryl residue, ($C_3$–$C_8$)-cycloalkyl, ($C_3$–$C_8$)-cycloalkyl-($C_1$–$C_6$)-alkyl, ($C_6$–$C_{12}$)-bicycloalkyl, ($C_6$–$C_{12}$)-bicycloalkyl-($C_1$–$C_6$)-alkyl, ($C_2$–$C_8$)-alkenyl, ($C_2$–$C_8$)-alkynyl or $R^{11}NH$. Even more preferably, $R^3$ is hydrogen, ($C_1$–$C_8$)-alkyl which can be optionally substituted by from 1 to 6 fluorine atoms, optionally substituted ($C_6$–$C_{10}$)-aryl, ($C_6$–$C_{10}$)-aryl-($C_1$–$C_4$)-alkyl which is optionally substituted in the aryl residue, optionally substituted heteroaryl, heteroaryl-($C_1$–$C_4$)-alkyl which is optionally substituted in the heteroaryl residue, ($C_3$–$C_8$)-cycloalkyl, ($C_3$–$C_8$)-cycloalkyl-($C_1$–$C_4$)-alkyl, ($C_6$–$C_{12}$)-bicycloalkyl, ($C_6$–$C_{12}$)-bicycloalkyl-($C_1$–$C_4$)-alkyl or $R^{11}NH$. Next to most preferably, $R^3$ is hydrogen, ($C_1$–$C_8$)-alkyl which can be optionally substituted by from 1 to 6 fluorine atoms, optionally substituted ($C_6$–$C_{10}$)-aryl, ($C_6$–$C_{10}$)-aryl-($C_1$–$C_4$)-alkyl which is optionally substituted in the aryl residue, optionally substituted heteroaryl, heteroaryl-($C_1$–$C_4$)-alkyl which is optionally substituted in the heteroaryl residue, ($C_3$–$C_8$)-cycloalkyl or ($C_3$–$C_8$)-cycloalkyl-($C_1$–$C_4$)-alkyl. Most preferably, $R^3$ is, for example, ($C_1$–$C_8$)-alkyl, in particular ($C_1$–$C_4$)-alkyl, for example, methyl, which can be optionally substituted by from 1 to 6 fluorine atoms, or is ($C_6$–$C_{10}$)-aryl, in particular phenyl, which can be unsubstituted or substituted.

$R^4$ is preferably ($C_1$–$C_8$)-alkyl which is unsubstituted or is substituted as specified in the above definition of $R^4$. More preferably, $R^4$ is ($C_1$–$C_8$)-alkyl, in particular ($C_1$–$C_6$)-alkyl, which is unsubstituted or substituted by one or two identical or different substituents selected from the group consisting of hydroxyl, ($C_1$–$C_8$)-alkoxy, $R^5$, optionally substituted ($C_3$–$C_8$)-cycloalkyl, hydroxycarbonyl, aminocarbonyl, ($C_6$–$C_{10}$)-aryl-($C_1$–$C_4$)-alkoxycarbonyl optionally substituted in the aryl residue, ($C_1$–$C_6$)-alkoxycarbonyl, $R^6$—CO, $R^7$—CO, tetrazolyl and trifluoromethyl. It iseven more preferred when one of the substituents in the alkyl group representing $R^4$ is bonded in the 1 position of the alkyl group, i.e., to that carbon atom of the alkyl group to which the nitrogen atom in the group $CONHR^4$ or in the group $CON(CH_3)R^4$ is bonded, and when said substituent in the 1 position is one of the residues hydroxycarbonyl, aminocarbonyl, ($C_6$–$C_{10}$)-aryl-($C_1$–$C_4$)-alkoxycarbonyl optionally substituted in the aryl residue, $R^6$—CO, $R^7$—CO, ($C_1$–$C_6$)-alkoxycarbonyl or tetrazolyl. In this even more preferred case, the residue —$NHR^4$ or the residue —$N(CH_3)R^4$ represents the residue of an α-amino acid or of an N-methyl-α-amino acid, respectively, or of a derivative thereof, with the residue of the amino acid being formally obtained by abstracting a hydrogen atom from the amino group of the amino acid (if the substituent in the 1 position is the group $R^6$—CO, the residue —$NHR^4$ or the residue —$N(CH_3)R^4$ then correspondingly represents the residue of a dipeptide, tripeptide, tetrapeptide or pentapeptide). It is specifically preferred when such α-amino acids are those having a lipophilic side chain, for example, phenylglycine, phenylalanine, valine, leucine, isoleucine and homologs thereof, including derivatives of these amino acids such as esters, amides or the derivatives in which the carboxylic acid group is converted into the residue $R^6$—CO or $R^7$—CO.

$R^5$ is preferably optionally substituted ($C_6$–$C_{12}$)-aryl, more preferably optionally substituted ($C_6$–$C_{10}$)-aryl, most preferably optionally substituted phenyl.

$R^8$ is preferably hydrogen, ($C_1$–$C_8$)-alkyl, optionally substituted ($C_6$–$C_{12}$)-aryl or ($C_6$–$C_{12}$)-aryl-($C_1$–$C_8$)-alkyl optionally substituted in the aryl residue, more preferably hydrogen, ($C_1$–$C_6$)-alkyl, optionally substituted ($C_6$–$C_{10}$)-aryl or ($C_6$–$C_{10}$)-aryl-($C_1$–$C_6$)-alkyl optionally substituted in the aryl residue, most preferably hydrogen, ($C_1$–$C_6$)-alkyl or phenyl-($C_1$–$C_4$)-alkyl which is optionally substituted in the phenyl residue. $R^{8a}$ preferably has one of the preferred meanings of $R^8$ with the exception of hydrogen.

$R^{10}$ is preferably hydroxyl, ($C_1$–$C_8$)-alkoxy, ($C_6$–$C_{12}$)-aryl-($C_1$–$C_8$)-alkoxy optionally substituted in the aryl residue, optionally substituted ($C_6$–$C_{12}$)-aryloxy, ($C_1$–$C_8$)- alkylcarbonyloxy-($C_1$–$C_6$)-alkoxy, ($C_6$–$C_{12}$)-aryl-($C_1$–$C_6$)-alkylcarbonyloxy-($C_1$–$C_6$)-alkoxy which is optionally substituted in the aryl residue, ($C_1$–$C_8$)-alkoxycarbonyloxy-($C_1$–$C_6$)-alkoxy, ($C_6$–$C_{12}$)-aryl-($C_1$–$C_6$)-alkoxycarbonyloxy-($C_1$–$C_6$)-alkoxy which is optionally substituted in the aryl residue, amino, mono- or di-(($C_1$–$C_8$)-alkyl)amino, aminocarbonyl-($C_1$–$C_6$)-alkoxy, (mono- or di-(($C_1$–$C_8$)-alkyl)amino)carbonyl-($C_1$–$C_6$)-alkoxy, (mono- or di-(($C_6$–$C_{12}$)-aryl-($C_1$–$C_6$)-alkyl))amino)carbonyl-($C_1$–$C_6$)-alkoxy or (N—(($C_1$–$C_8$)-alkyl)-N—(($C_6$–$C_{12}$)-aryl-($C_1$–$C_6$)-alkyl)amino)carbonyl-($C_1$–$C_6$)-alkoxy, both of which are optionally substituted in the aryl residue. More preferably, $R^{10}$ is hydroxyl, ($C_1$–$C_8$)-alkoxy, ($C_6$–$C_{10}$)-aryl-($C_1$–$C_6$)-alkoxy optionally substituted in the aryl residue, optionally substituted ($C_6$–$C_{10}$)-aryloxy, ($C_1$–$C_6$)-alkylcarbonyloxy-($C_1$–$C_6$)-alkoxy, ($C_1$–$C_6$)-alkoxycarbonyloxy-($C_1$–$C_6$)-alkoxy, amino, mono- or di-(($C_1$–$C_6$)-alkyl)amino, aminocarbonyl-($C_1$–$C_6$)-alkoxy or (mono- or di-(($C_1$–$C_6$)-alkyl)-amino)carbonyl-($C_1$–$C_6$)-alkoxy. Next to most preferably, $R^{10}$ is hydroxyl, ($C_1$–$C_8$)-alkoxy, ($C_6$–$C_{10}$)-aryl-($C_1$–$C_6$)-alkoxy optionally substituted in the aryl residue, optionally substituted ($C_6$–$C_{10}$)-aryloxy, ($C_1$–$C_6$)-alkylcarbonyloxy-($C_1$–$C_6$)-alkoxy or ($C_1$–$C_6$)-alkoxycarbonyloxy-($C_1$–$C_6$)-alkoxy. Most preferably, $R^{10}$ is hydroxyl or ($C_1$–$C_8$)-alkoxy, for example, hydroxyl or ($C_1$–$C_6$)-alkoxy.

$R^{11}$ is preferably hydrogen, $R^{12a}$, $R^{12a}$—CO, $R^{12a}$—O—CO, $R^{12b}$—CO, $R^{12b}$—CS or $R^{12a}$—S(O)$_2$; more preferably hydrogen, $R^{12a}$, $R^{12a}$—CO, $R^{12a}$—O—CO, $R^{12b}$—CO or $R^{12a}$—S(O)$_2$; and most preferably $R^{12a}$, $R^{12a}$—CO, $R^{12a}$—O—CO or $R^{12a}$—S(O)$_2$.

$R^{12a}$ is preferably ($C_1$–$C_{10}$)-alkyl, ($C_2$–$C_8$)-alkenyl, ($C_2$–$C_8$)-alkynyl, ($C_5$–$C_{10}$)-cycloalkyl, ($C_5$–$C_{10}$)-cycloalkyl-($C_1$–$C_8$)-alkyl, optionally substituted ($C_6$–$C_{12}$)-aryl, ($C_6$–$C_{12}$)-aryl-($C_1$–$C_8$)-alkyl which is optionally substituted in the aryl residue, optionally substituted heteroaryl, heteroaryl-($C_1$–$C_8$)-alkyl which is optionally substituted in the heteroaryl residue, or the residue $R^{15}$; more preferably ($C_1$–$C_{10}$)-alkyl, ($C_2$–$C_8$)-alkenyl, ($C_2$–$C_8$)-alkynyl, ($C_5$–$C_{10}$)-cycloalkyl, ($C_5$–$C_{10}$)-cycloalkyl-($C_1$–$C_8$)-alkyl, optionally substituted ($C_6$–$C_{12}$)-aryl, ($C_6$–$C_{12}$)-aryl-($C_1$–$C_8$)-alkyl which is optionally substituted in the aryl residue, optionally substituted heteroaryl or heteroaryl-($C_1$–$C_8$)-alkyl which is optionally substituted in the heteroaryl residue.

$R^{13}$ is preferably hydrogen or ($C_1$–$C_6$)-alkyl which can be optionally substituted by one or more fluorine atoms where preferred alkyl residues representing $R^{13}$ are the methyl residue and the trifluoromethyl residue. More preferably, $R^{13}$ is ($C_1$–$C_6$)-alkyl; and most preferably ($C_1$–$C_4$)-alkyl, both of which can be optionally substituted by one or more fluorine atoms, for example, methyl or trifluoromethyl.

$R^{15}$ is preferably $R^{16}$—($C_1$–$C_3$)-alkyl or $R^{16}$, in particular $R^{16}$—$C_1$-alkyl or $R^{16}$.

$R^{20}$ is preferably a direct linkage or a divalent ($C_1$–$C_4$)-alkylene residue, more preferably a direct linkage or a divalent ($C_1$–$C_2$)-alkylene residue (e.g., a direct linkage or a methylene residue or 1,2-ethylene residue), most preferably a direct linkage or a methylene residue.

$R^{21}$ is preferably hydrogen, ($C_1$–$C_8$)-alkyl, ($C_3$–$C_{10}$)-cycloalkyl, ($C_3$–$C_{10}$)-cycloalkyl-($C_1$–$C_6$)-alkyl, optionally substituted ($C_6$–$C_{10}$)-aryl, ($C_6$–$C_{10}$)-aryl-($C_1$–$C_6$)-alkyl which is optionally substituted in the aryl residue, the residue Het or the residue Het-($C_1$–$C_6$)-alkyl, where alkyl residues can be monosubstituted or polysubstituted by fluorine and, when they occur more than once, the residues $R^{21}$ are independent of each other and can be identical or different. $R^{21}$ is more preferably hydrogen, ($C_1$–$C_6$)-alkyl, ($C_3$–$C_6$)-cycloalkyl, ($C_3$–$C_6$)-cycloalkyl-($C_1$–$C_4$)-alkyl, optionally substituted ($C_6$–$C_{10}$)-aryl or ($C_6$–$C_{10}$)-aryl-($C_1$–$C_4$)-alkyl which is optionally substituted in the aryl residue, where alkyl residues can be monosubstituted or polysubstituted by fluorine. $R^{21}$ is most preferably hydrogen, ($C_1$–$C_6$)-alkyl, ($C_3$–$C_6$)-cycloalkyl, ($C_3$–$C_6$)-cycloalkyl-($C_1$–$C_2$)-alkyl, optionally substituted ($C_6$–$C_{10}$)-aryl or ($C_6$–$C_{10}$)-aryl-($C_1$–$C_2$)-alkyl optionally substituted in the aryl residue, where alkyl residues can be monosubstituted or polysubstituted by fluorine and where, when they occur more than once, the residues $R^{21}$ are independent of each other and can be identical or different.

$R^{30}$ is preferably one of the residues $R^{32}$(R)N—CO—N(R)—$R^{31}$, $R^{32}$(R)N—CS—N(R)—$R^{31}$, $R^{32}$(R)N—S(O)$_n$—N(R)—$R^{31}$, $R^{32}$—CO—N(R)—$R^{31}$, $R^{32}$—CS—N(R)—$R^{31}$, $R^{32}$—S(O)$_n$—N(R)—$R^{31}$, $R^{32}$(R)N—CO—$R^{31}$, $R^{32}$(R)N—CS—$R^{31}$, $R^{32}$(R)N—S(O)$_n$—$R^{31}$, $R^{32}$—CO—$R^{31}$, $R^{32}$—S(O)$_n$—$R^{31}$ and $R^{12a}$—O—CO—N(R)—$R^{31}$, in which n is 1 or 2. More preferably $R^{30}$ is one of the residues $R^{32}$(R)N—CO—N(R)—$R^{31}$, $R^{32}$(R)N—CS—N(R)—$R^{31}$, $R^{32}$—CO—N(R)—$R^{31}$, $R^{32}$—CS—N(R)—$R^{31}$, $R^{32}$(R)N—CO—$R^{31}$ or $R^{32}$(R)N—CS—$R^{31}$. Even more preferably, $R^{30}$ is one of the residues $R^{32}$(R)N—CO—N(R)—$R^{31}$, $R^{32}$(R)N—CS—N(R)—$R^{31}$, $R^{32}$—CO—N(R)—$R^{31}$ or $R^{32}$(R)N—CO—$R^{31}$. Next to most preferably, $R^{30}$ is $R^{32}$(R)N—CO—N(R)—$R^{31}$ or $R^{32}$(R)N—CS—N(R)—$R^{31}$, most preferably $R^{32}$(R)N—CO—N(R)—$R^{31}$, in particular $R^{32}$NH—CO—NH—$R^{31}$.

$R^{32}$ is preferably hydrogen, ($C_1$–$C_8$)-alkyl which can be optionally substituted by from 1 to 8 fluorine atoms, ($C_2$–$C_8$)-alkenyl, ($C_2$–$C_8$)-alkynyl, ($C_3$–$C_{10}$)-cycloalkyl, ($C_3$–$C_{10}$)-cycloalkyl-($C_1$–$C_8$)-alkyl, ($C_6$–$C_{12}$)-bicycloalkyl, ($C_6$–$C_{12}$)-bicycloalkyl-($C_1$–$C_8$)-alkyl, ($C_6$–$C_{12}$)-tricycloalkyl, ($C_6$–$C_{12}$)-tricycloalkyl-($C_1$–$C_8$)-alkyl, optionally substituted ($C_6$–$C_{12}$)-aryl, ($C_6$–$C_{12}$)-aryl-($C_1$–$C_8$)-alkyl optionally substituted in the aryl residue, optionally substituted heteroaryl or heteroaryl-($C_1$–$C_8$)-alkyl which is optionally substituted in the heteroaryl residue. More preferably, $R^{32}$ is hydrogen, ($C_1$–$C_6$)-alkyl which can be optionally substituted by from 1 to 6 fluorine atoms, ($C_2$–$C_6$)-alkenyl, ($C_2$–$C_6$)-alkynyl, ($C_5$–$C_6$)-cycloalkyl, ($C_5$–$C_6$)-cycloalkyl-($C_1$–$C_6$)-alkyl, optionally substituted ($C_6$–$C_{10}$)-aryl, ($C_6$–$C_{10}$)-aryl-($C_1$–$C_6$)-alkyl which is optionally substituted in the aryl residue, optionally substituted heteroaryl or heteroaryl-($C_1$–$C_6$)-alkyl which is optionally substituted in the heteroaryl residue. Even more preferably, $R^{32}$ is hydrogen, ($C_1$–$C_6$)-alkyl which can be optionally substituted by from 1 to 6 fluorine atoms, ($C_2$–$C_6$)-alkenyl, ($C_2$–$C_6$)-alkynyl, ($C_5$–$C_6$)-cycloalkyl, ($C_5$–$C_6$)-cycloalkyl-($C_1$–$C_4$)-alkyl, optionally substituted ($C_6$–$C_{10}$)-aryl, ($C_6$–$C_{10}$)-aryl-($C_1$–$C_4$)-alkyl which is optionally substituted in the aryl residue, optionally substituted heteroaryl or heteroaryl-($C_1$–$C_4$)-alkyl which is optionally substituted in the heteroaryl residue. An especially preferred residue representing $R^{32}$ is optionally substituted $(C_6-C_{10})$-aryl, in particular unsubstituted phenyl or phenyl which is substituted by one or more (e.g., one, two or three) identical or different substituents selected from the above-mentioned substituents which can be present on aryl groups (e.g., by alkyl substituents, such as methyl). If the residue $R^{32}$ is bonded to a sulfur atom, it then preferably has a meaning other than hydrogen.

$R^{33}$ is preferably a direct linkage or a divalent $(C_1-C_4)$-alkylene residue, particularly preferably a direct linkage or a divalent $(C_1-C_2)$-alkylene residue, very particularly preferably a direct linkage.

$R^{34}$ is preferably a divalent residue selected from the group consisting of $(C_1-C_8)$-alkylene, $(C_5-C_{10})$-cycloalkylene, $(C_6-C_{12})$-bicycloalkylene, optionally substituted $(C_6-C_{14})$-arylene and optionally substituted heteroarylene; more preferably a divalent residue selected from the group consisting of $(C_1-C_6)$-alkylene, $(C_5-C_6)$-cycloalkylene, optionally substituted $(C_6-C_{10})$-arylene and optionally substituted heteroarylene. Even more preferably, $R^{34}$ is a divalent residue selected from the group consisting of $(C_1-C_6)$-alkylene, optionally substituted $(C_6-C_{10})$-arylene and optionally substituted heteroarylene. Most preferably $R^{34}$ is a divalent residue selected from the group consisting of $(C_1-C_4)$-alkylene and optionally substituted $(C_6-C_{10})$-arylene, in particular optionally substituted $(C_6-C_{10})$-arylene, for example, unsubstituted phenylene or phenylene which is substituted by one or more (e.g., one, two or three) identical or different substituents selected from the above-mentioned substituents which can be present on aryl groups (e.g., by alkoxy substitutents, such as methoxy or trifluoromethoxy). Preferably, in a phenylene residue representing $R^{34}$, the residues $R^{33}$ and $R^{35}$ are in the 1,3 position or the 1,4 position with respect to each other, in particular in the 1,4 position.

$R^{35}$ is preferably a direct linkage or a divalent $(C_1-C_4)$-alkylene residue, particularly preferably a direct linkage or a divalent $(C_1-C_2)$-alkylene residue, very particularly preferably $(C_1-C_2)$-alkylene, in particular methylene or 1,2-ethylene.

$R^{36}$ is preferably a direct linkage.

$R^{31}$ is preferably a divalent residue —$R^{33}$—$R^{34}R$—$R^{36}$—, in which one or more of the residues $R^{33}$, $R^{34}$, $R^{35}$ and $R^{36}$ have preferred meanings. More preferably, $R^{31}$ is a divalent residue selected from the group consisting of $(C_1-C_8)$-alkylene, $(C_5-C_6)$-cycloalkylene, $(C_5-C_6)$-cycloalkylene-$(C_1-C_6)$-alkyl, optionally substituted $(C_6-C_{10})$-arylene, $(C_6-C_{10})$-arylene-$(C_1-C_6)$-alkyl which is optionally substituted in the arylene residue, optionally substituted heteroarylene, heteroarylene-$(C_1-C_6)$-alkyl which is optionally substituted in the heteroarylene residue, $(C_1-C_8)$-alkylene-CO, optionally substituted $(C_6-C_{10})$-arylene-CO, $(C_6-C_{10})$-arylene-$(C_1-C_6)$-alkyl-CO which is optionally substituted in the arylene residue, optionally substituted heteroarylene-CO, heteroarylene-$(C_1-C_6)$-alkyl-CO which is optionally substituted in the heteroarylene residue, optionally substituted $(C_6-C_{10})$-arylene-$S(O)_n$, $(C_6-C_{10})$-arylene-$(C_1-C_6)$-alkyl-$S(O)_n$ which is optionally substituted in the arylene residue, optionally substituted heteroarylene-$S(O)_n$ and heteroarylene-$(C_1-C_6)$-alkyl-$S(O)_n$ which is optionally substituted in the heteroarylene residue, in which n is 1 or 2, and in which the CO group and the $S(O)_n$ group are bonded to the nitrogen atom in the imidazolidine ring in the formula I and, in the case of the residues cycloalkylenealkyl, arylenealkyl and heteroarylenealkyl, the alkyl group is bonded to the nitrogen atom in the imidazolidine ring in the formula I. Even more preferably, $R^{31}$ is a divalent residue selected from the group consisting of $(C_1-C_6)$-alkylene, optionally substituted $(C_6-C_{10})$-arylene and $(C_6-C_{10})$-arylene-$(C_1-C_4)$-alkyl which is optionally substituted in the aryl residue, in which, in the case of the arylenealkyl residue, the alkyl group is bonded to the nitrogen atom in the imidazolidine ring in the formula I. Next to most preferably $R^{31}$ is a divalent residue selected from the group consisting of $(C_1-C_6)$-alkylene and $(C_6-C_{10})$-arylene-$(C_1-C_4)$-alkyl which is optionally substituted in the aryl residue, in particular $(C_6-C_{10})$-arylene-$(C_1-C_2)$-alkyl which is optionally substituted in the aryl residue, in which, in the case of the arylenealkyl residue, the alkyl group is bonded to the nitrogen atom in the imidazolidine ring in the formula I. Most preferably, $R^{31}$ is the divalent residue phenylenemethyl (—$C_6H_4$—$CH_2$—), in particular the residue -(1,4-phenylene)-methyl-, in which the methyl group is bonded to the nitrogen atom in the imidazolidine ring in the formula I and in which the phenylene residue is unsubstituted or monosubstituted or polysubstituted as described above, for example, by alkoxy such as methoxy or trifluoromethoxy.

If $R^3$ is hydrogen, $(C_1-C_{10})$-alkyl which can be optionally substituted by fluorine, optionally substituted $(C_6-C_{14})$-aryl, $(C_6-C_{14})$-aryl-$(C_1-C_8)$-alkyl which is optionally substituted in the aryl residue, optionally substituted heteroaryl, heteroaryl-$(C_1-C_8)$-alkyl which is optionally substituted in the heteroaryl residue, $(C_3-C_8)$-cycloalkyl, $(C_3-C_8)$-cycloalkyl-$(C_1-C_8)$-alkyl, $(C_6-C_{12})$-bicycloalkyl, $(C_6-C_{12})$-bicycloalkyl-$(C_1-C_8)$-alkyl, $(C_6-C_{12})$-tricycloalkyl, $(C_6-C_{12})$-tricycloalkyl-$(C_1-C_8)$-alkyl, $(C_2-C_8)$-alkenyl, $(C_2-C_8)$-alkynyl, $COOR^{21}$, $CON(CH_3)R^4$, $CONHR^4$, $COOR^{15}$, $CON(CH_3)R^{15}$ or $CONHR^{15}$, preference is given to e being 0 and h being 1. If $R^3$ is $R^{11}NH$, preference is given to e being 1 and h being 0. In one embodiment of the invention, e is 0 and h is 1 and the group —NR—$[C(R)(R)]_e$—$C(R^2)(R^3)$—$[C(R)(R)]_h$-E in the formula I is preferably the group —NH—$CH(R^3)$—$CH_2$-E.

Preferred compounds of the formula I are those compounds in which one or more of the residues have preferred meanings or have one or more specific meanings from their definitions, with all combinations of preferred meanings and/or specific meanings being a subject of the invention.

Particular preference is given to compounds of the formula I in which

W is a divalent residue selected from the group consisting of $R^1$-A-$C(R^{13})$ and

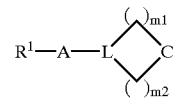

where the ring systems

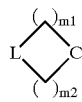

can contain one or two identical or different ring heteroatoms selected from the group consisting of nitrogen, oxygen and sulfur, can be saturated or monounsaturated or polyunsaturated, and can be substituted by 1, 2 or 3 identical or different $R^{13}$ substituents and/or by one or two oxo substituents and/or thioxo substituents, and in which L is $C(R^{13})$ or N, and in which m1 and m2, independently of each other, are 0, 1, 2, 3, 4, 5 or 6, but the sum m1+m2 is 1, 2, 3, 4, 5 or 6;

Y is a carbonyl group or thiocarbonyl group;

A is a direct linkage or one of the divalent residues $(C_1-C_6)$-alkylene, $(C_3-C_7)$-cycloalkylene, phenylene, phenylene-$(C_1-C_6)$-alkyl or phenylene-$(C_2-C_6)$-alkenyl, where in the residues phenylenealkyl and phenylenealkenyl the residue $R^1$ is bonded to the phenylene group;

B is a divalent residue selected from the group consisting of $(C_1-C_6)$-alkylene, $(C_2-C_6)$-alkenylene, phenylene, phenylene-$(C_1-C_3)$-alkyl, $(C_1-C_3)$-alkylenephenyl and $(C_1-C_3)$-alkylene-phenyl-$(C_1-C_3)$-alkyl, where the $(C_1-C_6)$-alkylene residue and the $(C_2-C_6)$-alkenylene residue are unsubstituted or are substituted by one or more identical or different residues selected from the group consisting of $(C_1-C_8)$-alkyl, $(C_2-C_8)$-alkenyl, $(C_2-C_8)$-alkynyl, $(C_3-C_{10})$-cycloalkyl, $(C_3-C_{10})$-cycloalkyl-$(C_1-C_6)$-alkyl, optionally substituted $(C_6-C_{14})$-aryl, $(C_6-C_{14})$-aryl-$(C_1-C_6)$-alkyl which is optionally substituted in the aryl residue, optionally substituted heteroaryl and heteroaryl-$(C_1-C_6)$-alkyl which is optionally substituted in the heteroaryl residue;

E is $R^8OCH_2$, $R^8CO-OCH_2$ or $R^{10}CO$;

R is hydrogen, $(C_1-C_8)$-alkyl, $(C_3-C_{12})$-cycloalkyl, $(C_3-C_{12})$-cycloalkyl-$(C_1-C_8)$-alkyl, optionally substituted $(C_6-C_{14})$-aryl or $(C_6-C_{14})$-aryl-$(C_1-C_8)$-alkyl which is optionally substituted in the aryl residue, where all the residues R are independent of each other and the residues R can be identical or different;

$R^1$ is hydrogen, $(C_1-C_{10})$-alkyl which can be optionally monosubstituted or polysubstituted by fluorine, $(C_3-C_{12})$-cycloalkyl, $(C_3-C_{12})$-cycloalkyl-$(C_1-C_8)$-alkyl, $R^{21}-((C_6-C_{14})$-aryl) which is optionally substituted in the aryl residue, $(R^{21}-((C_6-C_{14})$-aryl))-$(C_1-C_8)$-alkyl which is optionally substituted in the aryl residue, oxo or thioxo;

$R^2$ is hydrogen, $(C_1-C_8)$-alkyl, optionally substituted $(C_6-C_{14})$-aryl, $(C_6-C_{14})$-aryl-$(C_1-C_8)$-alkyl which is optionally substituted in the aryl residue, or $(C_3-C_8)$-cycloalkyl;

$R^3$ is hydrogen, $(C_1-C_8)$-alkyl, optionally substituted $(C_6-C_{14})$-aryl, $(C_6-C_{14})$-aryl-$(C_1-C_8)$-alkyl which is optionally substituted in the aryl residue, optionally substituted heteroaryl, heteroaryl-$(C_1-C_8)$-alkyl which is optionally substituted in the heteroaryl residue, $(C_3-C_8)$-cycloalkyl, $(C_3-C_8)$-cycloalkyl-$(C_1-C_8)$-alkyl, $(C_6-C_{12})$-bicycloalkyl, $(C_6-C_{12})$-bicycloalkyl-$(C_1-C_8)$-alkyl, $(C_6-C_{12})$-tricycloalkyl, $(C_6-C_{12})$-tricycloalkyl-$(C_1-C_8)$-alkyl, $(C_2-C_8)$-alkenyl, $(C_2-C_8)$-alkynyl or $R^{11}NH$;

$R^8$ is hydrogen, $(C_1-C_{10})$-alkyl, optionally substituted $(C_6-C_{14})$-aryl or $(C_6-C_{14})$-aryl-$(C_1-C_8)$-alkyl optionally substituted in the aryl residue, where the residues $R^8$ are independent of each other;

$R^{10}$ is hydroxyl, $(C_1-C_8)$-alkoxy, $(C_6-C_{12})$-aryl-$(C_1-C_8)$-alkoxy optionally substituted in the aryl residue, optionally substituted $(C_6-C_{12})$-aryloxy, $(C_1-C_8)$-alkylcarbonyloxy-$(C_1-C_6)$-alkoxy, $(C_6-C_{12})$-aryl-$(C_1-C_6)$-alkylcarbonyloxy-$(C_1-C_6)$-alkoxy which is optionally substituted in the aryl residue, $(C_1-C_8)$-alkoxycarbonyloxy-$(C_1-C_6)$-alkoxy, $(C_6-C_{12})$-aryl-$(C_1-C_6)$-alkoxycarbonyloxy-$(C_1-C_6)$-alkoxy which is optionally substituted in the aryl residue, amino, mono- or di-$((C_1-C_{10})$-alkyl)amino, or $R^8R^8N-CO-(C_1-C_6)$-alkoxy in which the residues $R^8$ are independent of each other and can be identical or different;

$R^{11}$ is hydrogen, $R^{12a}$, $R^{12a}-CO$, $H-CO$, $R^{12a}-O-CO$, $R^{12b}-CO$, $R^{12b}-CS$, $R^{12a}-S(O)_2$ or $R^{12b}-S(O)_2$;

$R^{12a}$ is $(C_1-C_{10})$-alkyl, $(C_2-C_8)$-alkenyl, $(C_2-C_8)$-alkynyl, $(C_3-C_{12})$-cycloalkyl, $(C_3-C_{12})$-cycloalkyl-$(C_1-C_8)$-alkyl, optionally substituted $(C_6-C_{14})$-aryl, $(C_6-C_{14})$-aryl-$(C_1-C_8)$-alkyl which is optionally substituted in the aryl residue, optionally substituted heteroaryl or heteroaryl-$(C_1-C_8)$-alkyl which is optionally substituted in the heteroaryl residue;

$R^{12b}$ is amino, di-$((C_1-C_{10})$-alkyl)amino or $R^{12a}-NH$;

$R^{13}$ is hydrogen, $(C_1-C_6)$-alkyl which can be optionally monosubstituted or polysubstituted by fluorine, optionally substituted $(C_6-C_{14})$-aryl, $(C_6-C_{14})$-aryl-$(C_1-C_6)$-alkyl which is optionally substituted in the aryl residue, $(C_3-C_8)$-cycloalkyl or $(C_3-C_8)$-cyclo-$(C_1-C_6)$-alkyl;

$R^{21}$ is hydrogen, $(C_1-C_8)$-alkyl, $(C_3-C_{12})$-cycloalkyl, $(C_3-C_{12})$-cycloalkyl-$(C_1-C_8)$-alkyl, optionally substituted $(C_6-C_{14})$-aryl or $(C_6-C_{14})$-aryl-$(C_1-C_8)$-alkyl which is optionally substituted in the aryl residue, where alkyl residues can be monosubstituted or polysubstituted by fluorine;

$R^{30}$ is one of the residues $R^{32}(R)N-CO-N(R)-R^{31}$, $R^{32}(R)N-CS-N(R)-R^{31}$, $R^{32}-CO-N(R)-R^{31}$, $R^{32}-CS-N(R)-R^{31}$, $R^{32}(R)N-CO-R^{31}$ or $R^{32}(R)N-CS-R^{31}$;

$R^{31}$ is the divalent residue $-R^{33}-R^{34}-R^{35}-R^{36}-$, where $R^{36}$ is bonded to the nitrogen atom in the imidazolidine ring in the formula I;

$R^{32}$ is hydrogen, $(C_1-C_8)$-alkyl which can be optionally substituted by from 1 to 8 fluorine atoms, $(C_2-C_8)$-alkenyl, $(C_2-C_8)$-alkynyl, $(C_3-C_{12})$-cycloalkyl, $(C_3-C_{12})$-cycloalkyl-$(C_1-C_8)$-alkyl, $(C_6-C_{12})$-bicycloalkyl, $(C_6-C_{12})$-bicycloalkyl-$(C_1-C_8)$-alkyl, $(C_6-C_{12})$-tricycloalkyl, $(C_6-C_{12})$-tricycloalkyl-$(C_1-C_8)$-alkyl, optionally substituted $(C_6-C_{14})$-aryl, $(C_6-C_{14})$-aryl-$(C_1-C_8)$-alkyl which is optionally substituted in the aryl residue, optionally substituted heteroaryl or heteroaryl-$(C_1-C_8)$-alkyl which is optionally substituted in the heteroaryl residue;

$R^{33}$ is a direct linkage or a divalent $(C_1-C_6)$-alkylene residue;

$R^{34}$ is a divalent residue selected from the group consisting of $(C_1-C_8)$-alkylene, $(C_3-C_{12})$-cycloalkylene, $(C_6-C_{12})$-bicycloalkylene, $(C_6-C_{12})$-tricycloalkylene, optionally substituted $(C_6-C_{14})$-arylene and optionally substituted heteroarylene;

$R^{35}$ is a direct linkage or a divalent $(C_1-C_8)$-alkylene residue;

$R^{36}$ is a direct linkage;

e and h are, independently of each other, 0 or 1;

in all their stereoisomeric forms and mixtures thereof in all ratios, and their physiologically tolerated salts.

More preference is given to compounds of the formula I in which

W is the divalent residue $R^1$-A-C($R^{13}$);

Y is a carbonyl group;

A is a direct linkage or one of the divalent residues $(C_1-C_6)$-alkylene, $(C_3-C_7)$-cycloalkylene, phenylene, phenylene-$(C_1-C_6)$-alkyl or phenylene-$(C_2-C_6)$-alkenyl, where in the residues phenylenealkyl and phenylenealkenyl the residue $R^1$ is bonded to the phenylene group;

B is a divalent methylene residue, where the methylene residue is unsubstituted or is substituted by one or two identical or different residues selected from the group consisting of $(C_1-C_8)$-alkyl, $(C_2-C_8)$-alkenyl, $(C_2-C_8)$-alkynyl, $(C_3-C_{10})$-cycloalkyl, $(C_3-C_{10})$-cycloalkyl-$(C_1-C_6)$-alkyl, optionally substituted $(C_6-C_{14})$-aryl and $(C_6-C_{14})$-aryl-$(C_1-C_6)$-alkyl which is optionally substituted in the aryl residue;

E is $R^{10}CO$, $R^8O-CH_2$ or $R^8CO-O-CH_2$;

R is hydrogen or $(C_1-C_8)$-alkyl, where all the residues R are independent of each other and the residues R can be identical or different;

$R^1$ is hydrogen or $(C_1-C_{10})$-alkyl which can be optionally monosubstituted or polysubstituted by fluorine;

$R^2$ is hydrogen or $(C_1-C_8)$-alkyl;

$R^3$ is hydrogen, $(C_1-C_8)$-alkyl which can be optionally substituted by from 1 to 8 fluorine atoms, optionally substituted $(C_6-C_{14})$-aryl, $(C_6-C_{14})$-aryl-$(C_1-C_8)$-alkyl which is optionally substituted in the aryl residue, optionally substituted heteroaryl, heteroaryl-$(C_1-C_8)$-alkyl which is optionally substituted in the heteroaryl residue, $(C_3-C_8)$-cycloalkyl, $(C_3-C_8)$-cycloalkyl-$(C_1-C_8)$-alkyl, $(C_6-C_{12})$-bicycloalkyl, $(C_6-C_{12})$-bicycloalkyl-$(C_1-C_8)$-alkyl, $(C_2-C_8)$-alkenyl, $(C_2-C_8)$-alkynyl or $R^{11}NH$;

$R^8$ is hydrogen, $(C_1-C_6)$-alkyl, optionally substituted $(C_6-C_{10})$-aryl or $(C_6-C_{10})$-aryl-$(C_1-C_6)$-alkyl optionally substituted in the aryl residue;

$R^{10}$ is hydroxyl, $(C_1-C_8)$-alkoxy, $(C_6-C_{12})$-aryl-$(C_1-C_8)$-alkoxy optionally substituted in the aryl residue, optionally substituted $(C_6-C_{12})$-aryloxy, $(C_1-C_8)$-alkylcarbonyloxy-$(C_1-C_6)$-alkoxy, $(C_6-C_{12})$-aryl-$(C_1-C_6)$-alkylcarbonyloxy-$(C_1-C_6)$-alkoxy which is optionally substituted in the aryl residue, $(C_1-C_8)$-alkoxycarbonyloxy-$(C_1-C_6)$-alkoxy, $(C_6-C_{12})$-aryl-$(C_1-C_6)$-alkoxycarbonyloxy-$(C_1-C_6)$-alkoxy which is optionally substituted in the aryl residue, amino, mono- or di-$((C_1-C_8)$-alkyl)amino, aminocarbonyl-$(C_1-C_6)$-alkoxy, (mono- or di-$((C_1-C_8)$-alkyl)-amino)carbonyl-$(C_1-C_6)$-alkoxy, or (mono- or di-$((C_6-C_{12})$-aryl-$(C_1-C_6)$-alkyl))amino)-carbonyl-$(C_1-C_6)$-alkoxy or (N—$((C_1-C_8)$-alkyl)-N—$((C_6-C_{12})$-aryl-$(C_1-C_6)$-alkyl)amino)-carbonyl-$(C_1-C_6)$-alkoxy both of which are optionally substituted in the aryl residue;

$R^{11}$ is hydrogen, $R^{12a}$, $R^{12a}$ CO, $R^{12a}$—CO, $R^{12b}$—O—CO, $R^{12b}$—CS or $R^{12a}$—S(O)$_2$;

$R^{12a}$ is $(C_1-C_{10})$-alkyl, $(C_2-C_8)$-alkenyl, $(C_2-C_8)$-alkynyl, $(C_5-C_{10})$-cycloalkyl, $(C_5-C_{10})$-cycloalkyl-$(C_1-C_8)$-alkyl, optionally substituted $(C_6-C_{14})$-aryl, or $(C_6-C_{14})$-aryl-$(C_1-C_8)$-alkyl which is optionally substituted in the aryl residue;

$R^{12b}$ is amino, di-$((C_1-C_{10})$-alkyl)amino or $R^{12a}$—NH;

$R^{13}$ is hydrogen or $(C_1-C_6)$-alkyl which can be optionally monosubstituted or polysubstituted by fluorine;

$R^{30}$ is one of the residues $R^{32}(R)N-CO-N(R)-R^{31}$ or $R^{32}(R)N-CS-N(R)-R^{31}$;

$R^{31}$ is the divalent residue $-R^{33}-R^{34}-R^{35}-R^{36}-$, where $R^{36}$ is bonded to the nitrogen atom in the imidazolidine ring in the formula I;

$R^{32}$ is hydrogen, $(C_1-C_8)$-alkyl which can be optionally substituted by from 1 to 8 fluorine atoms, $(C_2-C_8)$-alkenyl, $(C_2-C_8)$-alkynyl, $(C_3-C_{12})$-cycloalkyl, $(C_3-C_{12})$-cycloalkyl-$(C_1-C_8)$-alkyl, $(C_6-C_{12})$-bicycloalkyl, $(C_6-C_{12})$-bicycloalkyl-$(C_1-C_8)$-alkyl, $(C_6-C_{12})$-tricycloalkyl, $(C_6-C_{12})$-tricycloalkyl-$(C_1-C_8)$-alkyl, optionally substituted $(C_6-C_{14})$-aryl, or $(C_6-C_{14})$-aryl-$(C_1-C_8)$-alkyl which is optionally substituted in the aryl residue;

$R^{33}$ is a direct linkage or a divalent $(C_1-C_6)$-alkylene residue;

$R^{34}$ is a divalent residue selected from the group consisting of $(C_1-C_8)$-alkylene, $(C_5-C_{10})$-cycloalkylene, $(C_6-C_{12})$-bicycloalkylene and optionally substituted $(C_6-C_{14})$-arylene;

$R^{35}$ is a direct linkage or a divalent $(C_1-C_8)$-alkylene residue;

$R^{36}$ is a direct linkage;

e and h are, independently of each other, 0 or 1;

in all their stereoisomeric forms and mixtures thereof in all ratios, and their physiologically tolerated salts.

Special preference is given to compounds of the formula I in which

W is the divalent residue $R^1$-A-C($R^{13}$);

Y is a carbonyl group;

A is a direct linkage or the divalent residue $(C_1-C_6)$-alkylene;

B is a divalent methylene residue, where the methylene residue is unsubstituted or is substituted by one or two identical or different residues selected from the group consisting of $(C_1-C_8)$-alkyl, $(C_3-C_6)$-cycloalkyl-$(C_1-C_6)$-alkyl and $(C_6-C_{10})$-aryl-$(C_1-C_6)$-alkyl which is optionally substituted in the aryl residue;

E is $R^{10}CO$, $HO-CH_2$ or $R^8CO-O-CH_2$;

R is hydrogen or $(C_1-C_8)$-alkyl, where all the residues R are independent of each other and the residues R can be identical or different;

$R^1$ is hydrogen or $(C_1-C_{10})$-alkyl which can be optionally monosubstituted or polysubstituted by fluorine;

$R^2$ is hydrogen;

$R^3$ is hydrogen, $(C_1-C_8)$-alkyl which can be optionally substituted by from 1 to 6 fluorine atoms, optionally substituted $(C_6-C_{10})$-aryl, $(C_6-C_{10})$-aryl-$(C_1-C_6)$-alkyl which is optionally substituted in the aryl residue, optionally substituted heteroaryl, heteroaryl-$(C_1-C_6)$-alkyl which is optionally substituted in the heteroaryl residue, $(C_3-C_8)$-cycloalkyl or $(C_3-C_8)$-cycloalkyl-$(C_1-C_6)$-alkyl;

$R^8$ is hydrogen, $(C_1-C_6)$-alkyl or phenyl-$(C_1-C_4)$-alkyl which is optionally substituted in the phenyl residue;

$R^{10}$ is hydroxyl, $(C_1-C_8)$-alkoxy, $(C_6-C_{10})$-aryl-$(C_1-C_6)$-alkoxy optionally substituted in the aryl residue, optionally substituted $(C_6-C_{10})$-aryloxy, $(C_1-C_6)$-alkylcarbonyloxy-$(C_1-C_6)$-alkoxy or $(C_1-C_6)$-alkoxycarbonyloxy-$(C_1-C_6)$-alkoxy;

$R^{13}$ is hydrogen or $(C_1-C_6)$-alkyl which can be optionally monosubstituted or polysubstituted by fluorine;

$R^{30}$ is one of the residues $R^{32}(R)N—CO—N(R)—R^{31}$ or $R^{32}(R)N—CS—N(R)—R^{31}$;

$R^{31}$ is the divalent residue —$R^{33}$—$R^{34}$—$R^{35}$—$R^{36}$—, where $R^{36}$ is bonded to the nitrogen atom in the imidazolidine ring in the formula I;

$R^{32}$ is hydrogen, $(C_1-C_6)$-alkyl which can be optionally substituted by from 1 to 6 fluorine atoms, optionally substituted $(C_6-C_{10})$-aryl or $(C_6-C_{10})$-aryl-$(C_1-C_6)$-alkyl which is optionally substituted in the aryl residue;

$R^{33}$ is a direct linkage or a divalent $(C_1-C_4)$-alkylene residue;

$R^{34}$ is a divalent residue selected from the group consisting of $(C_1-C_6)$-alkylene, $(C_5-C_6)$-cycloalkylene and optionally substituted $(C_6-C_{10})$-arylene;

$R^{35}$ is a direct linkage or a divalent $(C_1-C_4)$-alkylene residue;

$R^{36}$ is a direct linkage;

e and h are, independently of each other, 0 or 1;

in all their stereoisomeric forms and mixtures thereof in all ratios, and their physiologically tolerated salts.

Even more preference is given to compounds of the formula I in which

W is the divalent residue $R^1$-A-C($R^{13}$);

Y is a carbonyl group;

A is a direct linkage;

B is a divalent methylene residue which is substituted by isobutyl or cyclopropylmethyl;

E is $R^{10}$CO or HO—$CH_2$;

R is hydrogen;

$R^1$ is methyl or trifluoromethyl;

$R^2$ is hydrogen;

$R^3$ is hydrogen, $(C_1-C_8)$-alkyl which can be optionally substituted by from 1 to 6 fluorine atoms, optionally substituted $(C_6-C_{10})$-aryl, $(C_6-C_{10})$-aryl-$(C_1-C_4)$-alkyl which is optionally substituted in the aryl residue, optionally substituted heteroaryl, heteroaryl-$(C_1-C_4)$-alkyl which is optionally substituted in the heteroaryl residue, $(C_3-C_8)$-cycloalkyl or $(C_3-C_8)$-cycloalkyl-$(C_1-C_4)$-alkyl;

$R^{10}$ is hydroxyl, $(C_1-C_8)$-alkoxy, $(C_6-C_{10})$-aryl-$(C_1-C_6)$-alkoxy optionally substituted in the aryl residue, optionally substituted $(C_6-C_{10})$-aryloxy, $(C_1-C_6)$-alkylcarbonyloxy-$(C_1-C_6)$-alkoxy or $(C_1-C_6)$-alkoxycarbonyloxy-$(C_1-C_6)$-alkoxy;

$R^{13}$ is methyl or trifluoromethyl;

$R^{30}$ is one of the residues $R^{32}(R)N—CO—N(R)—R^{31}$ or $R^{32}(R)N—CS—N(R)—R^{31}$;

$R^{31}$ is the divalent residue phenylenemethyl which is optionally substituted in the phenyl residue, where the methyl group of the phenylenemethyl residue is bonded to the nitrogen atom in the imidazolidine ring in the formula I;

e is 0 and h is 1;

in all their stereoisomeric forms and mixtures thereof in all ratios, and their physiologically tolerated salts.

In general, preference is given to compounds of the formula I which are present in uniform configuration, or in essentially uniform configuration, at one or more chiral centers, for example, at the carbon atom carrying the residues $R^2$ and $R^3$ and/or at the center W in the imidazolidine ring in the formula I provided that they are appropriately substituted for being chiral. That is, preference is given to compounds which are present uniformly, or essentially uniformly, in the R configuration or the S configuration at one or more chiral centers, but are not present as an RS mixture. However, the individual chiral centers in these compounds of the formula I can exhibit the R configuration or the S configuration independently of each other and can have the same or different configurations.

The compounds of formula I can be prepared, for example, by reductive amination of a compound of the formula II

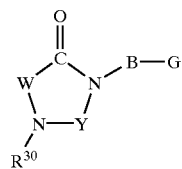

II with a compound of the formula III,

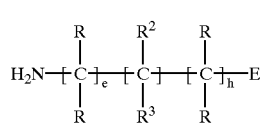

III where in the formulae II and III the groups B, E, W, Y, R, $R^2$, $R^3$ and $R^{30}$ and e and h are defined as specified above, or else functional groups can be present in these groups in protected form or in the form of precursors, and where G is the aldehyde group CHO. When compounds of the formula I are to be prepared in which a group, for example, the group $R^3$, is a carboxylic acid derivative group or contains such a group, the respective group, for example, $R^3$, in the compounds of formula III can initially be a hydroxycarbonyl group which is present in protected form or contain such a group, with the desired final group $R^3$ only subsequently being synthesized in one or more additional steps. Precursors of functional groups are groups which can be converted into the desired functional group using the customary synthesis methods which are known to the skilled person. For example, a nitro group can be converted into an amino group by reduction, for example, by catalytic hydrogenation, and can be regarded as being a precursor of an amino group or of a group which can be obtained from the amino group by means of further reactions. A cyano group, which can be converted by reduction into an aminomethyl group, or by hydrolysis into a carboxamide group or a carboxylic acid group, can be regarded as being a precursor of these groups. An alcohol group which can be oxidized to give an aldehyde group or a ketone group can be regarded as being a precursor of these groups. However, a precursor of a group also can be a group from which a relatively large part of the target molecule can be synthesized in several reaction steps which are carried out subsequently. Examples of protecting groups which are attached to the molecule before carrying out a reaction or a reaction sequence, and which are subsequently cleaved off again, are mentioned above.

The amino compounds of the formula III are commercially available or can be synthesized by well-known standard methods or in analogy to such methods, from starting compounds which are commercially available or which can be obtained as described in the literature or in analogy to procedures described in the literature. For example, optically active 3-substituted 3-aminopropionic acids of the formula III or their esters, in particular 3-aryl-3-aminopropionic esters, can be prepared from the corresponding 3-substituted acrylic acids, which can be obtained from the corresponding aldehydes. The 3-substituted acrylic acids can be converted, for example, into the acid chlorides with oxalyl chloride, and these acid chlorides can be converted with alcohols into the esters, for example, into the tert-butyl esters using tert-butanol. In order to introduce the amino group, then a reaction with the lithium salt of an optically active amine, for example, the lithium salt of (R)-(+)—N-benzyl-N-(1-phenylethyl)amine, can be performed, and subsequently the benzyl group and the phenylethyl group in the resulting 3-substituted tert-butyl 3-(N-benzyl-N-(1-phenylethyl) amino)propionate be cleaved off by means of catalytic hydrogenation (see S. G. Davies et al., *Tetrahedron: Asymmetry* 2,183 (1991) and *J. Chem. Soc. Perkin Trans* 1, 1129, (1994)). For preparing compounds of the formula III in which E represents the hydroxymethyl group $CH_2OH$ or an etherified hydroxymethyl group, it is possible to employ in the condensation reaction 3-substituted 3-aminopropanols or their ethers, which can be obtained from the 3-substituted 3-aminopropionic acids or their esters by reduction of the acid group or the ester group, for example, from the ethyl ester or tert-butyl ester using lithium aluminum hydride or lithium aluminum hydride/aluminum trichloride.

The reductive aminations of compounds of the formula II with compounds of the formula III can be carried out under standard conditions which are well known to the skilled person (see, for example, J. Martinez et al., *J. Med. Chem.*, 1985, 28:1874; L. Kosynkina et al., *Tetrahedron Lett.*, 1994, 35:5173; T. Kolter et al., *Liebigs Ann.*, 1995:625). Apart from using complex hydrides, such as using sodium cyanoborohydride, the reduction of the imine intermediate which is initially formed in the reductive amination reaction from the aldehyde and the amine, also can be effected using, for example, hydrogen in the presence of a metal catalyst such as palladium/charcoal. As has already been stated in a general manner, when performing the reductive amination reaction it can be advantageous or necessary for functional groups to be protected with protecting groups, which are then eliminated in a suitable manner after the reaction.

The compounds of the formula II, in which G represents the aldehyde group CHO, can be obtained from the corresponding carboxylic acids or from derivatives of the corresponding carboxylic acids, that is from the corresponding compounds of the formula IV,

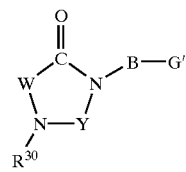

IV in which G' represents the carboxylic acid group COOH or a derivative of the carboxylic acid group, for example, an ester group, such as a $(C_1–C_6)$-alkyl ester group, or a suitable amide group, and the other groups have the meanings given above for formula II. A carboxylic acid of the formula IV, or an ester thereof, can first be reduced to the alcohol, that is to a compound of the formula IV which contains a hydroxymethyl group $CH_2OH$ in place of the group G', for example, using lithium aluminum hydride, and the resulting alcohol can subsequently be oxidized to the aldehyde, for example, using the method of Swern in the presence of dimethyl sulfoxide. In another procedure for preparing the aldehydes, compounds of the formula IV in which G' represents hydroxycarbonyl, for example, are reacted with N-methoxy-N-methylamine applying standard methods for preparing amides, to give the corresponding N-methoxy-N-methylamides (Weinreb amides) which are subsequently reduced to the aldehydes, for example, using lithium aluminum hydride (see, for example, J.-A. Fehrentz, B. Castro, *Synthesis*, 1983, 676). A has already been stated in a general manner, in these reactions, too, it can be advantageous or necessary for functional groups to be protected with protecting groups which are then eliminated in a suitable manner after the reaction, or for functional groups to be present in the form of precursors.

Compounds of the formula IV, in which W represents $R^1$-A-C($R^{13}$) and Y represents a carbonyl group, can be prepared, for example, by initially reacting compounds of the formula V

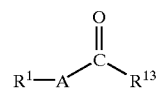

V in a Bucherer reaction, for example, using ammonium carbonate and potassium cyanide, to give compounds of the formula VI

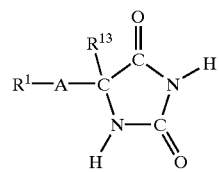

VI where, in the formulae V and VI, the groups $R^1$, $R^{13}$ and A are defined as specified above. Compounds of the formula VII,

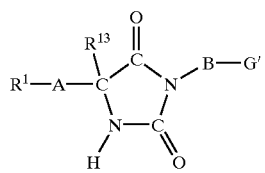

VII in which $R^1$, $R^{13}$, A and B are defined as specified above, and G' represents $(C_1-C_6)$-alkoxycarbonyl or hydroxycarbonyl, can then be obtained by, for example, initially reacting the compounds of the formula VI with an alkylating reagent which introduces the residue -B-G' into the molecule. The subsequent reaction of compounds of the formula VII with a reagent of the formula $R^{30}$-LG, in which $R^{30}$ has the abovementioned meanings and LG represents a nucleophilically substitutable leaving group, for example, halogen, such as chlorine or bromine, sulfonyloxy, such as tosyloxy, methylsulfonyloxy or trifluoromethylsulfonyloxy, $(C_1-C_4)$-alkoxy, optionally substituted phenoxy or a heterocyclic leaving group such as imidazolyl, then leads to the corresponding compounds of the formula IV in which G' represents $(C_1-C_6)$-alkoxycarbonyl or hydroxycarbonyl and W represents $R^1$-A-C($R^{13}$).

In a general manner, it may also be advantageous, depending on the meanings of the residue $R^{30}$ and of other residues, not to use the reagent $R^{30}$-LG to introduce the final residue $R^{30}$ directly into the molecule but, instead, to synthesize the residue $R^{30}$ on the imidazolidine ring after a precursor of the group $R^{30}$ has been connected to the imidazolidine ring. This can be done, for example, at the stage of a compound of the formula VII or at the stage of another intermediate in the synthesis. By way of example, this approach is described below using compounds in which $R^{30}$ represents the urea group $R^{32}(R)N-CO-N(R)-R^{31}$. Compounds of the formula IV in which $R^{30}$ represents $R^{32}(R)N-CO-N(R)-R^{31}$ can be prepared in accordance with this approach by, for example, initially reacting a compound of the formula VII with a reagent of the formula PG-N(R)—$R^{31}$-LG, in which LG represents a nucleophilically substitutable leaving group as explained above, to give a compound of the formula VIII

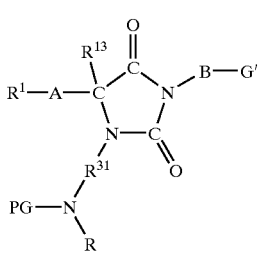

VIII in which PG represents an amino protecting group, for example, tert-butoxycarbonyl or benzyloxycarbonyl, and in which otherwise the meanings given above for the compounds of the formula VII and I apply. After the protecting group PG has been removed, compounds of the formula IV, in which $R^{30}$ represents $R^{32}NH-CO-N(R)-R^{31}$, are then obtained by reacting the resulting amino group —NHR with an isocyanate of the formula $R^{32}-N=C=O$. Compounds of the formula IV in which $R^{30}$ represents $R^{32}(R)N-CO-N(R)-R^{31}$ are obtained by employing in the reaction, for example, a carbamoyl chloride of the formula $R^{32}(R)N-CO-Cl$. In a corresponding manner the analogous thiourea derivatives can be obtained using isothiocyanates and thiocarbamoyl chlorides. (Thio)Acylamines, sulfonylamines, sulfinylamines and sulfamides can be obtained by reacting the amino group with reactive carboxylic acid derivatives, thiocarboxylic acid derivatives, sulfonic acid derivatives, sulfinic acid derivatives and sulfamoyl chlorides. Just like compounds of the formula VIII, it also is possible to prepare, and employ in subsequent reaction steps, compounds in which in the formula VIII the group PG-N(R)— has been replaced with a group which constitutes a precursor of an amino group and which is then converted into an amino group in a subsequent reaction step. For example, a compound of the formula VII can initially be reacted with a nitro compound of the formula $O_2N-R^{31}$-LG or a cyano compound of the formula $NC-R^{31}$-LG to give a compound corresponding to the compound of the formula VIII, in which the nitro group or the cyano group can be converted, for example, by catalytic hydrogenation, into an amino group which amino group can then be converted into the desired target group, for example, using an isocyanate of the formula $R^{32}-N=C=O$ to give a urea derivative in which $R^{30}$ represents $R^{32}NH-CO-NH-R^{31}$, or else using other compounds. This approach can be used to synthesize a large number of other compounds of the formula I, with the reactions to be performed always being standard methods which are familiar to the skilled person.

In general, the individual steps performed in preparing the compounds of the formula I can be carried out using methods known per se which are familiar to the skilled person, or in analogy to such methods. As has already been explained, depending on the particular case, in can be appropriate in all steps involved in the synthesis of the compounds of the formula I to temporarily block functional groups which might be able to lead to side reactions or undesirable reactions, using a protecting group strategy which is adapted to the synthetic route, as is known to the skilled person. The above-explained approach of not introducing functional groups directly into the molecule in their final form but, instead, initially introducing precursors into the molecule and then synthesizing the final functional group at the stage of an intermediate can, as has already been mentioned, also be applied correspondingly for other parts of the molecule of the formula I, for example, for the group $R^1$ or the group $R^3$.

Compounds of the formula IV, in which W is

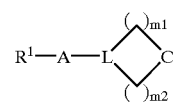

and Y is a carbonyl group, can be prepared, for example, by reacting compounds of the formula IX,

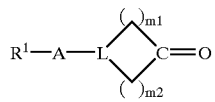

in which $R^1$, A, L, m1 and m2 are defined as specified above, in a Bucherer reaction, as described above for the preparation of the compounds of the formula VI, to give compounds of the formula X

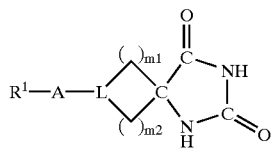

and converting these compounds, using a reagent which introduces the residue -B-G' into the molecule, as described above for the preparation of the compounds of the formula VII, into compounds of the formula XI

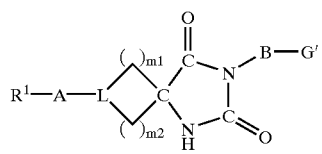

where, in the compounds of the formulae X and XI, the groups $R^1$, A, B, and L and m1 and m2 have the above-mentioned meanings, and G' is defined as in formula IV. The compounds of the formula XI can then be reacted, in accordance with the above-described reactions of the compounds of the formula VII, for example, with a reagent of the formula $R^{30}$-LG or a reagent of the formula PG-N(R)—$R^{31}$-LG.

If W is the residue $R^1$-A-C($R^{13}$)=C or the residue

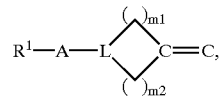

this structural element can be introduced, for example, by condensing the corresponding aldehyde or the corresponding ketone, in analogy with known methods, with a dioxo- or thioxo-oxo-imidazolidine which contains an unsubstitued methylene group in the position which corresponds to the group W in the formula I or to the group $R^1$-A-C($R^{13}$) in the formula VI.

Compounds of the formula I in which W is $R^1$-A-C($R^{13}$) also can be obtained by reacting a compound of the formula XII,

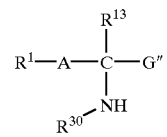

in which A, $R^1$, $R^{13}$ and $R^{30}$ are defined as specified above, and G" is, for example, an ester group such as $(C_1-C_6)$-alkoxycarbonyl, with an isocyanate or isothiocyanate of the formula XIII

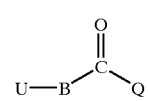

in which B is defined as specified above for the formula I and U is isocyanato or isothiocyanato, and Q is an alkoxy group, for example, a $(C_1-C_4)$-alkoxy group such as methoxy, ethoxy or tert-butoxy, a $(C_6-C_{14})$-aryloxy group such as phenoxy, or a $(C_6-C_{14})$-aryl-$(C_1-C_4)$-alkoxy group such as benzyloxy. This reaction results in a compound of the formula XIV

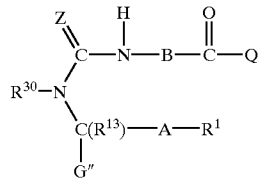

in which Z is oxygen or sulfur and A, B, G", Q, $R^1$, $R^{13}$ and $R^{30}$ are defined as specified for the formulae XII and XIII, which compound is then cyclized, under the influence of an acid or a base, to give a compound of the formula XV,

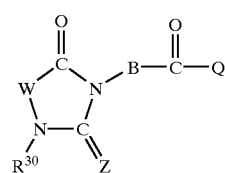

in which W is $R^1$-A-C($R^{13}$) and Z, B, Q and $R^{30}$ are defined as specified above. With catalysis by a base, the cyclization can be achieved, for example, by treatment with sodium hydride in an inert aprotic solvent such as dimethylformamide. A compound of the formula I in which W is $R^1$-A-C($R^{13}$) can then be obtained from the compound of the formula XV by, for example, hydrolyzing the group CO-Q to give the carboxylic acid COOH, converting this into the Weinreb amide, reducing the Weinreb amide to the corresponding aldehyde and subsequently performing a reductive amination using a compound of the formula III, as described above for the reductive amination of the compounds of the formula II. In this synthesis method, as well, it can be expedient for functional groups to be present in protected form or in the form of precursors.

Compounds of the formula I in which Y is a carbonyl group also can be prepared by first coupling a compound of the formula XVI,

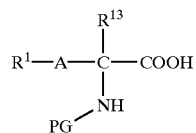

XVI in which A, $R^1$ and $R^{13}$ have the abovementioned meanings, and PG is an amino protecting group, such as a benzyloxycarbonyl group, using a standard method for forming an amide bond, to a compound of the formula XVII,

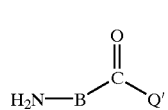

XVII in which B has the abovementioned meanings and the group COQ' is a protected carboxylic acid group, for example, an alkoxycarbonyl group such as tert-butoxycarbonyl, to give a compound of the formula XVIII

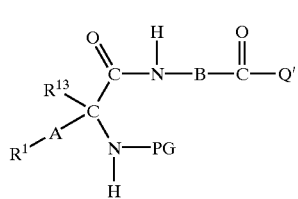

XVIII in which $R^1$, $R^{13}$, A, B, PG and COQ' have the abovementioned meanings. The protecting group PG in the compound of the formula XVIII can then be selectively eliminated from the amino group, for example, by means of hydrogenating in the case of a benzyloxycarbonyl group, and a ring closure can be performed, by introducing a carbonyl group, to give a compound of the formula XIX,

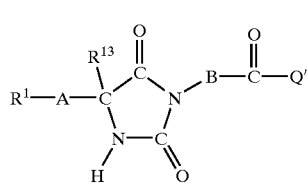

XIX in which $R^1$, $R^{13}$, A, B and COQ' have the abovementioned meanings. Phosgene or a phosgene equivalent, such as diphosgene or triphosgene, can be used, for example, for introducing the carbonyl group. As an intermediate step in the conversion of the compound of the formula XVIII into the compound of the formula XIX, for example, an isocyanate can appear or can be prepared deliberately. The conversion of the compound of the formula XVIII into the compound of the formula XIX can take place in one or more steps. For example, the cyclization which is effected after the carbonyl group has been introduced can be carried out, like the above-described cyclizations, separately in the presence of a base such as sodium hydride. Compounds of the formula XVIII in which PG is an alkoxycarbonyl group, an arylalkoxycarbonyl group or an aryloxycarbonyl group also can be converted directly into compounds of the formula XIX without a synthetic building block, such as phosgene, being used for introducing the carbonyl group. If, for example, compounds of the formula XVIII in which PG is benzyloxycarbonyl are treated with a base, such as sodium hydride or sodium carbonate, it is possible to obtain the compounds of the formula VII directly.

Compounds of formula IV in which G' is a hydroxycarbonyl group COOH can advantageously be prepared from compounds of the formula XX,

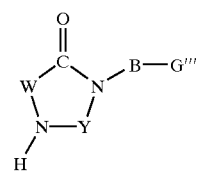

XX in which G''' is a hydroxycarbonyl group and W and Y are defined as specified above, by reacting the compounds of the formula XX in the presence of excess base, for example, in the presence of an excess of n-butyllithium, with an alkylating reagent, for example, with an alkylating agent of the formula $R^{30}$-LG in which $R^{30}$ and LG are defined as specified above, and subsequently acidifying. When carrying out this alkylating reaction, it can be expedient for functional groups to be present in protected form or in the form of a precursor. Depending on the meaning of the residue $R^{30}$ and of other residues, it also can be advantageous in the case of this reaction to synthesize the residue $R^{30}$ on the imidazolidine ring as explained above.

Compounds of the formula I can furthermore be prepared by reducing the amide group C(=O)—NR in compounds of the formula XXI,

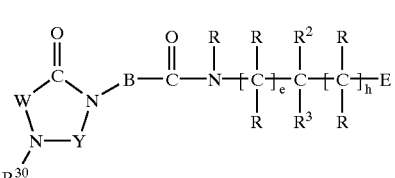

XXI in which B, E, W, Y, R, $R^2$, $R^3$, $R^{30}$, e and h have the meanings given for the compounds of the formulae II and III, to the amino group $CH_2$—NR under conditions known to the skilled person, for example, using the borane-dimethyl sulfide complex. The compounds of formula XXI can be prepared, using standard methods for forming amide bonds, from compounds of the formula III, or the analogous compounds which contain an RNH group in place of the terminal $H_2N$ group in the formula III, and compounds of the formula IV.

The following reagents, for example, can be used to obtain a guanidino group contained in the residue $R^1$ from an amino group, which amino group can in turn be obtained, for example, from a nitro group or a cyano group by reduction:

a) O-methylisourea (S. Weiss and H. Krommer, *Chemiker-Zeitung,* 98 (1974), 617–618)

b) S-methylisothiourea (R. F. Borne, M. L. Forrester and I. W. Waters, *J. Med. Chem.,* 20 (1977), 771–776)

c) nitro-S-methylisothiourea (L. S. Hafner and R. E. Evans, *J. Org. Chem.,* 24 (1959) 57)

d) formamidinosulfonic acid (K. Kim, Y.-T. Lin and H. S. Mosher, *Tetrah. Lett.,* 29 (1988), 3183–3186)

e) 3,5-dimethyl-1-pyrazolylformamidinium nitrate (F. L. Scott, D. G. O'Donovan and J. Reilly, *J. Amer. Chem. Soc.,* 75 (1953), 4053–4054)

f) N,N'-di-tert-butyloxycarbonyl-S-methylisothiourea (R. J. Bergeron and J. S. McManis, *J. Org. Chem.,* 52 (1987), 1700–1703)

g) N-alkoxycarbonyl-, N,N'-dialkoxycarbonyl-, N-alkylcarbonyl- and N,N'-dialkylcarbonyl-S-methylisothiourea (H. Wollweber, H. Kölling, E. Niemers, A. Widdig, P. Andrews, H.-P. Schulz and H. Thomas, *Arzneim. Forsch./Drug Res.,* 34 (1984), 531–542).

Amidines can be prepared from the corresponding cyano compounds by the addition of alcohols, for example, methanol or ethanol, in acidic anhydrous medium, for example, dioxane, methanol or ethanol, and subsequent aminolysis, for example treatment with ammonia in alcohols such as isopropanol, methanol or ethanol (G. Wagner, P. Richter and Ch. Garbe, *Pharmazie,* 29 (1974), 12–55). Another method of preparing amidines is the addition of hydrogen sulfide to the cyano group, followed by a methylation of the resulting thioamide and subsequent reaction with ammonia (DDR patent No. 235 866). Furthermore, hydroxylamine can be added to the cyano group, to give N-hydroxyamidines which, if desired, can likewise be converted into the amidines, for example, by means of hydrogenation.

Compounds of the formula I in which W is $(CF_3)_2C$ can be prepared, for example, by converting a compound of the formula VII, in which $R^1$ is trifluoromethyl, A is a direct linkage and $R^{13}$ is trifluoromethyl, as explained above for the compounds of the formula VII, into a compound of the formula IV in which G' is $(C_1-C_6)$-alkoxycarbonyl or hydroxycarbonyl, from which the corresponding compound of the formula II, in which G is CHO, can be obtained as described above. Compounds of the formula VII, in which the residues $R^1$-A- and $R^{13}$ are trifluoromethyl and G' is an ester group such as $(C_1-C_6)$-alkoxycarbonyl, that is has the meaning of G", can advantageously be prepared by reacting an isonitrile of the formula XXII with the 2-tert-butoxy-4,4-bis(trifluoromethyl)-1,3-oxazabuta-1,3-diene of the formula XXIII to give a compound of the formula XXIV

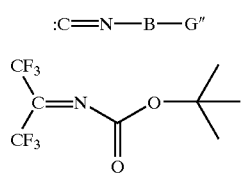

XXII

XXIII

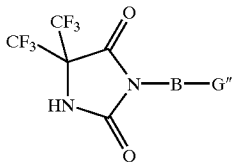

XXIV where B and G" have the abovementioned meanings (i.e., the group G" is $(C_1-C_6)$-alkoxycarbonyl, for example, $(C_1-C_4)$-alkoxycarbonyl such as methoxy, ethoxy or tert-butoxy). The reaction of the compounds of the formulae XXII and XXIII to give the compounds of the formula XXIV is advantageously carried out with heating in a hydrocarbon or ether as solvent, for example, in benzene or toluene. The isocyanides (isonitriles) of the formula XXII can be obtained, using standard methods known to the skilled person, from the corresponding amino acid esters of the formula $H_2N$-B-G", in which B and G" have the abovementioned meanings. Advantageously, the amino acid ester of the formula $H_2N$-B-G" is initially converted, by reaction with a reactive formic acid ester, for example, cyanomethyl formate, into the N-formylamino acid ester of the formula HC(=O)—NH-B-G", which is then converted, for example, by reaction with phosgene or a phosgene equivalent such as diphosgene or triphosgene, in the presence of a tertiary amine such as triethylamine, into the isocyanide of the formula XXII. The 2-tert-butoxy-4,4-bis(trifluoromethyl)-1,3-oxazabuta-1,3-diene of the formula XXIII can be obtained, using the method described by Steglich et al., *Chemische Berichte,* 107 (1974), 1488, from tert-butyl carbamate (tert-butoxycarbonylamide) and anhydrous hexafluoroacetone and subsequently treating the 2-tert-butoxycarbonylamino-2-hydroxy-1,1,1,3,3,3-hexafluoropropane, which is initially obtained, with trifluoroacetic anhydride in the presence of a base, such as quinoline.

Standard methods can be used to convert compounds of the formula I, in which E is, for example, hydroxycarbonyl or hydroxymethyl, into compounds of the formula I in which E has other meanings, or into other prodrugs or derivatives of the compounds of the formula I. Thus, in order to prepare esters, for example, the compounds of the formula I in which E is hydroxycarbonyl can be esterified with alcohols, for example, in the presence of a condensing reagent such as carbonyldiimidazole or a carbodiimide such as DCC (dicyclohexylcarbodiimide), or the compounds of the formula I in which E is hydroxycarbonyl can be alkylated with alkyl halides such as alkyl chlorides or alkyl bromides, for example, using chloroalkanoic acid amides to give compounds of the formula I in which E is $R^8R^8N$—CO-alkoxy-CO—, or using acyloxyalkyl halides to give compounds of the formula, in which E is acyloxyalkoxy-CO—. Compounds of the formula I in which E is hydroxycarbonyl can be converted into amides using ammonia or organic amines in the presence of a condensing reagent. Compounds of the formula I in which E is CO—$NH_2$ can advantageously also be obtained on solid phase by coupling the compound in which E is COOH in the presence of a condensing reagent such as TOTU (O-((cyano(ethoxycarbonyl)methylene)amino)-N,N, N',N'-tetramethyluronium tetrafluoroborate) to Rink amide resin and then cleaving it off the resin again using trifluoroacetic acid. Compounds of the formula I, in which E is the hydroxymethyl group $CH_2OH$, can be etherified or esterified at the hydroxymethyl group using standard methods. Standard methods for selectively oxidizing alcohols to aldehydes, for example, using sodium hypochlorite in the presence of 4-acetamido-2,2,6,6-tetramethyl-1-piperidinyloxy (4-acetamido-TEMPO), can be used to convert compounds of the formula I in which E is $CH_2OH$ into compounds of the formula I in which E is the aldehyde group —CHO.

Furthermore, with regard to the preparation of the compounds of the formula I, the entire contents of WO-A-95/14008, of EP-A-796855 and of the applications corresponding to it, of EP-A-918059 and of the applications corresponding to it, and of WO-A-96/33976 are hereby incorporated by reference. In particular, reference is made to the disclosure in WO-A-96/33976 with regard to the preparation of the compounds of the formulae VI and VII, which is an integral part of the present disclosure.

The compounds of formula I are valuable pharmaceutically active compounds which are suitable, for example, for treating inflammatory diseases, allergic diseases or asthma. According to the invention, the compounds of formula I and their physiologically tolerated salts and derivatives can be administered as pharmaceuticals to animals, preferably to mammals, and in particular to humans, for the treatment of disease states. Treatment is understood as meaning, in a general manner, both therapy including alleviation and cure of disease symptoms, and prophylaxis or prevention of disease symptoms, such as, for example, the prevention of the appearance of allergic or asthmatic disease symptoms or the prevention of myocardial infarction or of myocardial reinfarction in relevant patients. The disease symptoms can be acute or chronic. The compounds of formula I, and their salts and derivatives, can be administered on their own, in mixtures with each other or in the form of pharmaceutical preparations which permit enteral or parenteral use and which comprise, as the active constituent, an effective dose of at least one compound of the formula I and/or its physiologically tolerated salts and/or derivatives and a pharmaceutically acceptable carrier.

The present invention therefore also relates to the compounds of formula I and/or their physiologically tolerated salts and derivatives for use as pharmaceuticals, to the use of the compounds of the formula I and/or their physiologically tolerated salts and derivatives for preparing pharmaceuticals for treating the above diseases and those mentioned below, for example, for treating inflammatory diseases, and also to the use of the compounds of the formula I and/or their physiologically tolerated salts and derivatives in the treatment of these diseases. The present invention furthermore relates to pharmaceutical preparations (or pharmaceutical compositions) which comprise an effective dose of at least one compound of the formula I and/or its physiologically tolerated salts and/or derivatives and a pharmaceutically acceptable carrier, that is one or more pharmaceutically acceptable vehicles and/or additives or auxiliaries.

The pharmaceuticals may be administered systemically or locally. They can be administered orally, for example, in the form of pills, tablets, film tablets, sugar-coated tablets, granules, hard and soft gelatin capsules, powders, solutions, syrups, emulsions or suspensions or in other galenical forms. However, the administration also can be effected vaginally or rectally, for example, in the form of suppositories, or parenterally or by means of an implant, for example, in the form of injection solutions or infusion solutions, microcapsules or rods, or topically or percutaneously, for example, in the form of creams, ointments, powders, solutions, emulsions or tinctures, or in another way, for example, in the form of nasal sprays or aerosol mixtures. Parenteral administration of solutions can occur, for example, intravenously, intramuscularly, subcutaneously, intraarticularly or intrasynovially, or in another manner.

The pharmaceutical preparations according to the invention are produced in a manner known per se, with the compound or the compounds of the formula I and/or their physiologically tolerated salts and/or derivatives being mixed with pharmaceutically inert inorganic and/or organic vehicles and/or additives and brought into a suitable dosage form and administration form. For example, lactose, corn starch or derivatives thereof, talc, stearic acid or its salts, polyethylene glycols, etc. can be used for producing pills, tablets, sugar-coated tablets and hard gelatin capsules, while fats, waxes, semisolid and liquid polyols, polyethylene glycols, natural or hardened oils, etc. can be used, for example, for producing soft gelatin capsules and suppositories. Examples of suitable vehicles for producing solutions, for example, injection solutions, or emulsions or syrups are water, alcohols, glycerol, diols, polyols, sucrose, invert sugar, glucose, vegetable oils, etc. Examples of suitable carrier substances for microcapsules, implants or rods are copolymers of glycolic acid and lactic acid. The pharmaceutical preparations normally comprise from about 0.5 to about 90% by weight of the compounds of the formula I and/or their physiologically tolerated salts and derivatives. The quantity of active compound of the formula I and/or its physiologically tolerated salts and derivatives in the pharmaceutical preparations is normally from about 0.2 to about 1 000 mg, preferably from about 1 to about 500 mg. However, depending on the nature of the pharmaceutical preparation, the quantity of the active compound also can be greater.

Aside from the active compounds and vehicles, the pharmaceutical preparations also can contain auxiliary substances or additives, for example, fillers, disintegrants, binders, glidants, wetting agents, stabilizers, emulsifiers, preservatives, sweeteners, dyes, flavorings, aromatizing agents, thickeners, diluents, buffering substances, solvents, solubilizers, agents for achieving a depot effect, salts for altering the osmotic pressure, coating agents or antioxidants. They also can comprise two or more compounds of the formula I and/or their physiologically tolerated salts and/or derivatives. Furthermore, apart from at least one compound of the formula I and/or its physiologically tolerated salts and derivatives, the pharmaceutical preparations also can comprise one or more additional pharmaceutically active compounds, for example, compounds which possess an antiinflammatory effect.

When the compounds of the formula I or pharmaceutical preparations comprising them are administered as aerosols (e.g., as nasal aerosols or by inhalation), this can be carried out, for example, using a spray, an atomizer, a pump atomizer, an inhalation appliance, a metered inhaler or a dry powder inhaler. Pharmaceutical forms for administering the compounds of formula I as aerosols can be produced using methods which are well known to the skilled person. For their production, for example, solutions or dispersions of the compounds of the formula I in water, water-alcohol mixtures or suitable sodium chloride solutions can be employed, using customary additives, for example, benzyl alcohol or other suitable preservatives, absorption improvers for increasing bioavailability, solubilizers, dispersing agents, and others, and, where appropriate, customary propellants, for example, fluorochlorohydrocarbons and/or fluorohydrocarbons.

Other pharmaceutically active compounds, which can be present together with compounds of the formula I in the pharmaceutical preparations according to the invention, but with which the compounds of the formula I also can be combined in other ways within the context of a combination treatment, are in particular those active compounds which are suitable for the treatment (i.e., the therapy or prophylaxis) of the diseases mentioned above or below and for whose treatment the compounds of the formula I are suitable. Examples of active compound classes of this type which may be mentioned are steroids, nonsteroidal antiinflammatory substances, nonsteroidal antiinflammatory acetic acid derivatives, nonsteroidal antiinflammatory propionic acid derivatives, nonsteroidal antiasthmatics, salicylic acid derivatives, pyrazolones, oxicams, leukotriene antagonists, inhibitors of leukotriene biosynthesis, cyclooxygenase inhibitors, cyclooxygenase-2 inhibitors (COX-2 inhibitors), antihistamines, H1-histamine antagonists, nonsedating antihistamines, gold compounds, β2-agonists, anticholinergics, muscarine antagonists, lipid-lowering agents, cholesterol-lowering agents, HMG-CoA reductase inhibitors, statins, nicotinic acid derivatives, immunosuppressants, cyclosporins, β-interferons, tumor therapeutic agents, cytostatic agents, metastasis inhibitors, antimetabolites, 5-aminosalicylic acid derivatives, antidiabetic agents, insulins, sulfonylureas, biguamides, glitazones, α-glucosidase inhibitors, and others. Examples of suitable active compounds which may be mentioned are acetylsalicylic acid, benorilate, sulfasalazine, phenylbutazone, oxyphenbutazone, metamizole, mofebutazone, feprazone, celecoxib, rofecoxib, diclofenac, fentiazac, sulindac, zomepirac, tolmetin, indometacin, acemetacin, ibuprofen, naproxen, carprofen, fenbufen, indoprofen, ketoprofen, pirprofen, tiaprofenic acid, diflunisal, flufenamic acid, meclofenamic acid, mefenamic acid, niflumic acid, tolfenamic acid, piroxicam, isoxicam, tenoxicam, nicotinic acid, prednisone, dexamethasone, hydrocortisone, methylprednisolone, betamethasone, beclomethasone, budesonide, montelukast, praniukast, zafirlukast, zileuton, cyclosporin, cyclosporin A, rapamycin, tacrolimus, methotrexate, 6-mercaptopurine, azathioprine, interferon-beta 1a, interferon-beta 1b, 5-aminosalicylic acid, leflunomide, D-penicillamine, chloroquine, glibenclamide, glimepiride, troglitazone, metformin, acarbose, atorvastatin, fluvastatin, lovastatin, simvastatin, pravastatin, colestipol, colestyramine, probucol, clofibrate, fenofibrate, bezafibrate, gemfibrozil, ipatropium bromide, clenbuterol, fenoterol, metaproterenol, pirbuterol, tulobuterol, salbutamol, salmeterol, terbutaline, isoetarine, ketotifen, ephedrine, oxitropium bromide, atropine, cromoglicic acid, theophylline, fexofenadine, terfenadine, cetirizine, dimetindene, diphenhydramine, diphenylpyraline, pheniramine, brompheniramine, chlorpheniramine, dexchlorpheniramine, alimemezaine, antazoline, astemizole, azatadine, clemastine, cyproheptadine, hydroxyzine, loratidine, mepyramine, promethazine, tripelennamine, triprolidine and others.

When compounds of the formula I and/or their physiologically tolerated salts and/or derivatives are used together with one or more other active compounds in a combination treatment, this can be carried out by all the active compounds being administered together in a single pharmaceutical preparation, for example, a tablet or capsule. The present invention likewise relates expressly to such pharmaceutical preparations to which all the above explanations apply correspondingly. In general, the amount of the active compounds in these pharmaceutical preparations is chosen such that an effective amount of each of the active compounds is present. However, a combination treatment also can be carried out by the active compounds being contained in two or more separate pharmaceutical preparations, which can be present in a single pack or in two or more separate packs. The compounds of the formula I and/or their physiologically tolerated salts or derivatives and the other active compounds can be administered either jointly or separately and be administered simultaneously or sequentially. The administration also can be effected in different ways; for example, one active compound can be administered orally and the other administered by injection, inhalation or topical application.

The compounds of the formula I have, for example, the ability to inhibit cell-cell interaction processes and cell-matrix interaction processes in which interactions between VLA-4 and its ligands play a role. The activity of the compounds of the formula I can be demonstrated, for example, in an assay which measures the binding of cells which possess the VLA-4 receptor, for example, leukocytes, to ligands of this receptor, for example, to VCAM-1 which can advantageously also be prepared recombinantly for this purpose. Details of such an assay are described below. In particular, the compounds of the formula I are able to inhibit the adhesion and migration of leukocytes, for example, the adhesion of leukocytes to endothelial cells, which adhesion, as explained above, is controlled by way of the VCAM-1/VLA-4 adhesion mechanism. Aside from their use as antiinflammatory agents, the compounds of the formula I and their physiologically tolerated salts and derivatives are therefore suitable, in a general manner, for the treatment (i.e., for the therapy and prophylaxis) of diseases which are based on the interaction between the VLA-4 receptor and its ligands or which can be influenced by an inhibition of this interaction, and are in particular suitable for treating diseases which, at least in part, are caused by or associated with, an undesirable extent of leukocyte adhesion and/or leukocyte migration and for whose prevention, alleviation or cure the adhesion and/or migration of leukocytes is to be reduced.

The present invention therefore also relates to the compounds of the formula I and their physiologically tolerated salts and derivatives for inhibiting the adhesion and/or migration of leukocytes or for inhibiting the VLA-4 receptor, and to the use of the compounds of the formula I and/or their physiologically tolerated salts and derivatives for producing pharmaceuticals for this purpose, that is pharmaceuticals for treating diseases in which the extent of leukocyte adhesion and/or leukocyte migration is undesirable, or for treating diseases in which VLA-4-dependent adhesion processes play a role, and to the use of the compounds of the formula I and/or their physiologically tolerated salts and derivatives in treating such diseases.

The compounds of the formula I can be used as antiinflammatory agents in the case of inflammatory symptoms arising from a very wide variety of causes in order to prevent, reduce or suppress the undesirable or damaging sequelae of the inflammation. The compounds of the formula I are used, for example, for the treatment (i.e., the therapy or prophylaxis) of arthritis, of rheumatoid arthritis, of polyarthritis, of inflammatory bowel disease (ulcerative colitis, Crohn's disease), of systemic lupus erythematosus, of inflammatory diseases of the central nervous system, such as multiple sclerosis, or of asthma or of allergies, such as delayed-type allergies (type IV allergy). The compounds are furthermore suitable for cardioprotection, for protection against stroke and for the secondary prophylaxis of stroke and for the treatment, that is the therapy and prophylaxis, of cardiovascular diseases, of atherosclerosis, of myocardial infarction, of myocardial reinfarction, of acute coronary syndrome, of stroke, of restenoses, of sepsis, of septic shock, of diabetes, of damage to organ transplants, of immune diseases, of autoimmune diseases, of tumor growth or tumor metastasis in the case of various malignancies, of malaria and of other diseases in which blocking the integrin VLA-4 and/or influencing leukocyte activity appears appropriate for achieving prevention, alleviation or cure. Preference is given to the use for the prevention of myocardial infarction or myocardial reinfarction or for the treatment (i.e., for the therapy and prevention) of atherosclerosis, asthma or multiple sclerosis.

The dose when using the compounds of the formula I can vary within wide limits and in each individual case is to be adjusted to the individual circumstances, as is customary and known to the physician. The dose depends, for example, on the nature and severity of the disease to be treated, on the condition of the patient and on the compound employed, on whether an acute or chronic disease state is being treated or whether prophylaxis is being pursued, or on whether other active compounds are being administered in addition to the compounds of the formula I. In general, when the dose is being administered orally, a daily dose of from about 0.01 to about 100 mg/kg, preferably of about 0.1 to about 10 mg/kg (in each case mg per kg of body weight) is appropriate for achieving effective results when the dose is being administered to an adult of about 75 kg in weight. When administered intravenously, the daily dose is in general from about 0.01 to 50 mg/kg, preferably from 0.01 to 10 mg/kg of body weight. Particularly when relatively large quantities are being administered, the daily dose can be divided up into several, for example, 2, 3, or 4, partial administrations. Where appropriate, depending on the individual response, it may be necessary to deviate in an upward or downward direction from the specified daily dose.

Aside from being used as pharmaceutically active compounds in human medicine and veterinary medicine, the compounds of the formula I and their salts and derivatives which are suitable for the desired us can additionally be used for diagnostic purposes, for example, in in vitro diagnoses of cell samples or tissue samples and as auxiliaries or scientific tools in biochemical investigations in which the blocking of VLA-4 or influencing of cell-cell interactions or cell-matrix interactions is desired. The compounds of the formula I and their salts also can be used as intermediates for preparing other compounds, in particular other pharmaceutically active compounds, which can be obtained from compounds of the formula I for example, by modifying or introducing residues or functional groups, for example, by esterification, reduction, oxidation or other transformations of functional groups.

EXAMPLES

Example 1

(R)-3-((S)-2-(4,4-Dimethyl-3-(4-(3-(2-methylphenyl)ureido)-3-methoxybenzyl)-2,5-dioxoimidazolidin-1-yl)-3-cyclopropylpropylamino) butyric acid hydrochloride

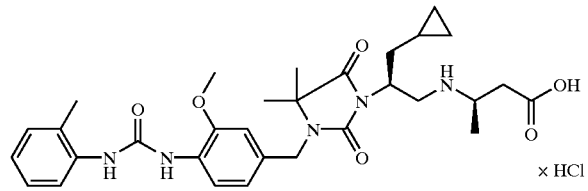

1a) 4-(3-(2-Methylphenyl)ureido)-3-methoxybenzyl alcohol 15 g (81.8 mmol) of 3-methoxy-4-nitrobenzyl alcohol were hydrogenated in 500 mL of methyl tert-butyl ether over 1.3 g of palladium/charcoal (10%; 50% water) while cooling with ice. After the uptake of hydrogen had ceased, the catalyst was filtered off and 10.14 mL (81.8 mmol) of 2-methylphenyl isocyanate were added to the filtrate within 30 minutes while stirring. The reaction mixture was left to stand overnight and the precipitated solid was filtered off with suction and washed with methyl tert-butyl ether. Yield: 20.5 g (88%).

1b) 4-(3-(2-Methylphenyl)ureido)-3-methoxybenzyl chloride 7.65 mL (104.8 mmol) of thionyl chloride were added dropwise, while cooling with ice, to a suspension of 15 g (52.4 mmol) of the compound of example 1a) in 300 mL of dichloromethane. The reaction mixture was stirred at room temperature for 3 h, left to stand overnight and then poured onto 1 000 mL of heptane. The heptane was decanted off from the oil which had separated; the residue was then slurried once again with heptane and the heptane was decanted off. This procedure was repeated a further two times. The residue was then dissolved in dichloromethane and this solution was poured into 800 mL of ice-cold diisopropyl ether. This mixture was stirred for 2 h while cooling with ice, the product was filtered off with suction and washed with diisopropyl ether. 12 g (75%) of the title compound were obtained after drying over phosphorus pentoxide.

1c) Benzyl (S)-2-amino-3-cyclopropylpropionate

1N Sodium hydroxide solution was added, at 0° C., to a suspension of 10 g (77.5 mmol) of (S)-2-amino-3-cyclopropylpropionic acid in 160 mL of dioxane until a pH of 8 to 9 was reached. 16.9 g (77.5 mmol) of di-tert-butyl dicarbonate were then added, the ice bath was removed, and the pH was kept at 8 to 9 by the further addition of 1N sodium hydroxide solution. After the mixture had been left to stand overnight, the dioxane was removed in vacuo, ethyl acetate was added to the aqueous phase, and the phases were separated. The aqueous phase was adjusted to pH 4.5 with 1N hydrochloric acid and extracted with ethyl acetate. The resulting ethyl acetate phase was dried over sodium sulfate, the drying agent was filtered off and the filtrate was concentrated in vacuo. The residue was dissolved in 1 000 mL of dichloromethane, and 53.4 mL of benzyl alcohol, 8.37 g of 4-dimethylaminopyridine and 18.8 g of DCC were added. After the mixture had been stirred for 6 h and left to stand overnight, it was filtered and the filtrate was concentrated and 300 mL of 90% trifluoroacetic acid were added to the residue. After the resulting mixture had been stirred at room temperature for 10 minutes, the trifluoroacetic acid was removed in vacuo and the residue was chromatographed twice over silica gel using dichloromethane/methanol (95/5). Yield: 11.48 g (68%).

1d) (S)-2-(4,4-Dimethyl-2,5-dioxoimidazolidin-1-yl)-3-cyclopropylpropionic acid 321 mg of HOBT (N-hydroxybenzotriazole) and 4.75 g (23.7 mmol) of DCC were added to a solution of 3.82 g (23.7 mmol) of 2-methoxycarbonylamino-2-methyl-propionic acid (prepared from 2-amino-2-methylpropionic acid and methyl chloroformate) and 5.2 g (23.7 mmol) of the compound of example 1c) in 100 mL of THF (tetrahydrofuran), and the mixture was stirred at room temperature for 4 h. After the mixture had been left to stand overnight, it was filtered, the THF was removed in vacuo, the residue was taken up in methyl tert-butyl ether and the solution was washed twice each with saturated $NaHCO_3$ solution and aqueous $KHSO_4/K_2SO_4$ solution. The organic phase was dried over sodium sulfate and, after filtration, the solvent was removed in vacuo. The residue was dissolved in ethyl acetate and hydrogenated in the presence of palladium/charcoal (10%; 50% water). The catalyst was filtered off and 500 mL of water and 10.1 g of sodium carbonate were added to the organic phase. Following extraction and phase separation, the aqueous phase was stirred at 100° C. for 24 hours and then allowed to stand overnight. 500 mL of 6N hydrochloric acid were added, and the aqueous phase was extracted three times with methyl tert-butyl ether. The combined organic phases were dried over sodium sulfate and, after filtration, concentrated in vacuo. The residue was crystallized using diisopropyl ether and the product filtered off. Yield: 2.88 g (51%).

1e) (S)-2-(4,4-Dimethyl-3-(4-(3-(2-methylphenyl) ureido)-3-methoxybenzyl)-2,5-dioxoimidazolidin-1-yl)-3-cyclopropylpropionic acid 9.44 mL of an n-butyllithium solution (2.5M in hexane) were added, under argon and at −40° C., to a solution of 2.85 g (11.8 mmol) of the compound of example 1d) in 60 mL of absolute THF. After the reaction mixture had been stirred at −40° C. for 30 minutes, it was allowed to warm to 0° C. and a solution of 3.6 g (11.8 mmol) of the compound of example 1b) in 20 mL of N-methyl-2-pyrrolidone was added. The reaction mixture was allowed to warm to 0° C. and left to stir at 0° C. for 2 h. 15 mL of 1N hydrochloric acid were added and the THF was removed in vacuo. The residue was poured onto 300 mL of methyl tert-butyl ether. The phases were separated and the organic phase was washed with water. The combined organic phases were dried over sodium sulfate and, after filtration, concentrated in vacuo. The residue was purified by preparative HPLC. After concentration of the product fractions and subsequent freeze-drying, 1.33 g (22%) of the title compound were obtained.

1f) (S)-2-(4,4-Dimethyl-3-(4-(3-(2-methylphenyl) ureido)-3-methoxybenzyl)-2,5-dioxoimidazolidin-1-yl)-3-cyclopropyl-N-methoxy-N-methylpropionamide While cooling with ice, 1.29 g (3.93 mmol) of TOTU and 1.26 mL (7.74 mmol) of diisopropylethylamine were added to a solution of 2 g (3.93 mmol) of the compound of example 1e) and 384 mg (3.93 mmol) of N,O-dimethylhydroxylamine hydrochloride in 30 mL of absolute DMF (dimethylformamide) and the reaction mixture was stirred at room temperature for 2 h. The solvent was removed in vacuo, the residue was taken up in ethyl acetate and the solution washed twice with saturated sodium hydrogencarbonate solution. The phases were separated and the organic phase was dried over magnesium sulfate. After filtration and removal of the solvent in vacuo, the residue was chromatographed over silica gel using ethyl acetate/heptane (7/3). Concentration of the product fractions yielded 1.84 g (85%) of the title compound.

1g) (S)-2-(4,4-Dimethyl-3-(4-(3-(2-methylphenyl) ureido)-3-methoxybenzyl)-2,5-dioxoimidazolidin-1-yl)-3-cyclopropylpropanal 160 mg (3.77 mmol) of lithium aluminum hydride were added, at −72° C., to a solution of 1.8 g (3.26 mmol) of the compound of example 1f) in 90 mL of absolute THF and the reaction mixture was stirred at 0° C. for 30 minutes. A pH value of 4 was then set by adding 0.5M $KHSO_4$ solution, dichloromethane was added and the phases were separated. The aqueous phase was extracted with dichloromethane. The combined organic phases were washed twice with 5% citric acid solution and dried over magnesium sulfate. After filtration and removal of the solvent in vacuo, the resulting crude title compound was used directly in the subsequent reaction.

1h) tert-Butyl (R)-3-((S)-2-(4,4-dimethyl-3-(4-(3-(2-methylphenyl)ureido)-3-methoxybenzyl)-2,5-dioxoimidazolidin-1-yl)-3-cyclopropylpropylamino) butyrate 222 mg (3.54 mmol) of sodium cyanoborohydride were added to a solution of 586 mg (1.18 mmol) of the compound of example 1g) and 378 mg (2.37 mmol) of tert-butyl (R)-3-aminobutyrate in 20 mL of THF/methanol (9/1) and 0.2 mL of acetic acid. The reaction mixture was stirred at room temperature for 1 h and then poured onto an ammonium chloride solution; the mixture was then extracted twice with dichloromethane. The combined organic phases were washed with saturated sodium hydrogencarbonate solution and dried over magnesium sulfate. After filtration and removal of the solvent in vacuo, the residue was chromatographed over silica gel using ethyl acetate/heptane (2/1). Concentration of the product fractions yielded 263 mg (35%) of the title compound.

1i) (R)-3-((S)-2-(4,4-Dimethyl-3-(4-(3-(2-methylphenyl) ureido)-3-methoxybenzyl)-2,5-dioxoimidazolidin-1-yl)-3-cyclopropylpropylamino)butyric acid hydrochloride 259 mg (0.408 mmol) of the compound of example 1h) were dissolved in 20 mL of trifluoroacetic acid and the solution was left to stand at room temperature for 3 h. After the reaction mixture had been concentrated in vacuo, the residue was treated twice with dichloromethane and in each case concentrated in vacuo. The residue was chromatographed over silica gel using dichloromethane/methanol/ acetic acid/water (9515/0.510.5). The product fractions were combined, the solvent was removed in vacuo, the residue was freeze-dried, treated with 1.5 equivalents of 1 M hydrochloric acid and freeze-dried once again. 200 mg (85%) of the title compound were obtained.

ES(+)-MS: 580.6 (3-(2-(4,4-Dimethyl-3-(4-(3-(2-methylphenyl)ureido)-3-methoxybenzyl)-2,5-dioxoimidazolidin-1-yl)-3-cyclopropylpropylamino)butyric acid+H)$^+$

Example 2

Ethyl (R)-3-((S)-2-(4,4-dimethyl-3-(4-(3-(2-methylphenyl)ureido)-3-methoxybenzyl)-2,5-dioxoimidazolidin-1-yl)-3-cyclopropylpropylamino) butyrate hydrochloride

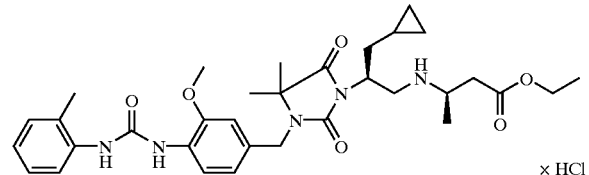

The title compound was prepared, in analogy with example 1h), from 520 mg (1.06 mmol) of the compound of example 1g) and 304 mg (2.32 mmol) of ethyl (R)-3-aminobutyrate. Yield after conversion into the hydrochloride: 164 mg (25%).

ES(+)-MS: 608.6 (Ethyl 3-(2-(4,4-dimethyl-3-(4-(3-(2-methylphenyl)ureido)-3-methoxybenzyl)-2,5-dioxoimidazolidin-1-yl)-3-cyclopropylpropylamino)-3-methyl-propionate+H)$^+$

Example 3

Isopropyl (R)-3-((S)-2-(4,4-dimethyl-3-(4-(3-(2-methylphenyl)ureido)-3-methoxybenzyl)-2,5-dioxoimidazolidin-1-yl)-3-cyclopropylpropylamino) butyrate hydrochloride

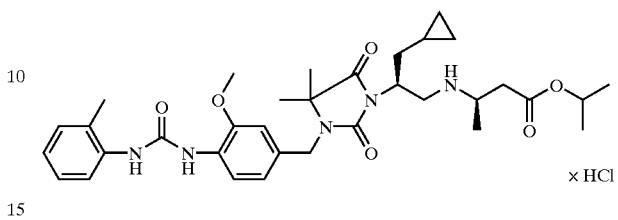

The title compound was prepared, in analogy with example 1h), from 2.62 g of the compound of example 1g) and 1.44 g (9.91 mmol) of isopropyl (R)-3-aminobutyrate. Following chromatography of the crude product using ethyl acetate/heptane (2/1), chromatographic purification by means of preparative HPLC, and conversion into the hydrochloride, 855 mg (26%) of the title compound were obtained.

ES(+)-MS: 622.7 (Isopropyl 3-(2-(4,4-dimethyl-3-(4-(3-(2-methylphenyl)ureido)-3-methoxybenzyl)-2,5-dioxoimidazolidin-1-yl)-3-cyclopropylpropylamino) butyrate+H)$^+$

Example 4

Isopropyl (S)-3-((S)-2-(4,4-dimethyl-3-(4-(3-(2-methylphenyl)ureido)-3-methoxybenzyl)-2,5-dioxoimidazolidin-1-yl)-3-cyclopropylpropylamino)-3-phenylpropionate hydrochloride

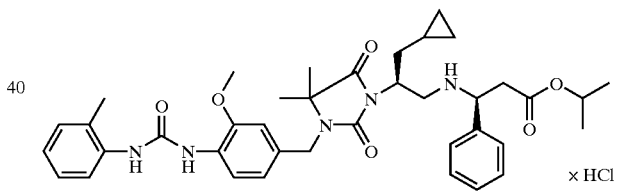

A solution of 780 mg (3.77 mmol) of isopropyl (S)-3-amino-3-phenylpropionate and 226 mg of acetic acid in 20 mL of methanol/acetic acid (99/1) was added to a solution of 1.86 g (3.77 mmol) of the compound of example 1g) in 50 mL of methanol/acetic acid (99/1). 710 mg (11.31 mmol) of sodium cyanoborohydride were added. After the mixture had been stirred at room temperature for 1 h, a further 237 mg (3.77 mmol) of sodium cyanoborohydride were added and, after a further 1 hour, 390 mg (1.885 mmol) of isopropyl (S)-3-amino-3-phenylpropionate, 113 mg of acetic acid and 237 mg (3.77 mmol) of sodium cyanoborohydride were added. After the mixture had been stirred at room temperature for 1 h, a further 237 mg (3.77 mmol) of sodium cyanoborohydride were added and the reaction mixture was stirred at room temperature for a further hour. The reaction mixture was adjusted to a pH of 4 with 1N hydrochloric acid, the methanol was removed in vacuo and the residue was extracted twice with dichloromethane. The combined organic phases were dried over magnesium sulfate. After filtration, concentration, chromatographic purification of the residue over silica gel using ethyl acetate/heptane (1/1), subsequent purification by means of preparative HPLC, and conversion into the hydrochloride, 980 mg (36%) of the title compound were obtained.

ES(+)-MS: 684.4 (Isopropyl 3-(2-(4,4-dimethyl-3-(4-(3-(2-methylphenyl)ureido)-3-methoxybenzyl)-2,5-dioxoimidazolidin-1-yl)-3-cyclopropylpropylamino)-3-phenylpropionate+H)⁺

Example 5

Ethyl (S)-3-((S)-2-(4,4-dimethyl-3-(4-(3-(2-methylphenyl)ureido)-3-methoxybenzyl)-2,5-dioxoimidazolidin-1-yl)-3-cyclopropylpropylamino)-3-phenylpropionate hydrochloride

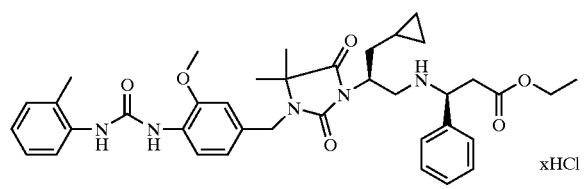

5a) (S)-2-(4,4-Dimethyl-3-(4-(3-(2-methylphenyl)ureido)-3-methoxybenzyl)-2,5-dioxoimidazolidin-1-yl)-3-cyclopropyl-N-methoxy-N-methylpropionamide 250 mg (0.49 mmol) of the compound of example 1d) were dissolved, together with 167 μL (1.08 mmol) of diisopropylcarbodiimide and 146 mg (1.08 mmol) of HOBT, in 4 mL of dichloromethane and 2 mL of acetonitrile. After the solution had been cooled to 0° C., a solution of 120 mg (1.23 mmol) of N,O-dimethylhydroxylamine hydrochloride in 1 mL of acetonitrile and 710 μL (1.23 mmol) of diisopropylethylamine was added. After 12 h, the reaction mixture was treated with aqueous ammonium chloride solution and extracted with dichloromethane. The organic phase was washed with aqueous sodium hydrogencarbonate solution, dried over magnesium sulfate, filtered and concentrated in vacuo. After chromatographic separation over silica gel using ethyl acetate/heptane (1/1), 250 mg (92%) of the title compound were obtained.

5b) Ethyl (S)-3-((S)-2-(4,4-dimethyl-3-(4-(3-(2-methylphenyl)ureido)-3-methoxybenzyl)-2,5-dioxoimidazolidin-1-yl)-3-cyclopropylpropylamino)-3-phenylpropionate hydrochloride 335 mg (0.6 mmol) of the compound of example 5a) in 2 mL of absolute THF were added dropwise, at −78° C., to a suspension of 23 mg (0.6 mmol) of lithium aluminum hydride in 2 mL of absolute THF. After 1 h at 0° C., the reaction mixture was treated with aqueous KHSO₄ solution and extracted with ethyl acetate. The organic phase was washed with aqueous hydrochloric acid and NaHCO₃ solution, dried over sodium sulfate, filtered and concentrated in vacuo. The residue and 234 mg (1.22 mmol) of ethyl (S)-3-amino-3-phenylpropionate were shaken for 8 h in a hydrogen atmosphere in 20 mL of ethanol in the presence of 20 mg of palladium/charcoal (10%). The reaction mixture was filtered and concentrated in vacuo. Following chromatographic purification by means of preparative HPLC, reaction with aqueous hydrochloric acid and freeze-drying, 50 mg (12%) of the title compound were obtained.

ES(+)-MS: 670.4 (Ethyl 3-(2-(4,4-dimethyl-3-(4-(3-(2-methylphenyl)ureido)-3-methoxybenzyl)-2,5-dioxoimidazolidin-1-yl)-3-cyclopropylpropylamino)-3-phenylpropionate+H)⁺

Example 6

(S)-3-((S)-2-(4,4-Dimethyl-3-(4-(3-(2-methylphenyl)ureido)-3-methoxybenzyl)-2,5-dioxoimidazolidin-1-yl)-3-cyclopropylpropylamino)-3-phenylpropionic acid hydrochloride

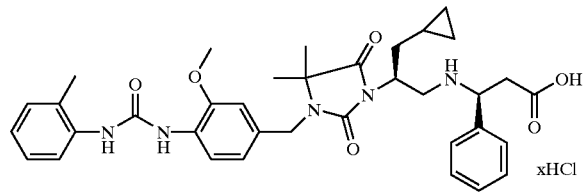

360 μL (0.36 mmol) of a 1 M aqueous solution of lithium hydroxide were added to 60 mg (0.09 mmol) of the compound of example 5 in 3 mL of methanol. After 12 h, the reaction solution was neutralized with aqueous hydrochloric acid and extracted with dichloromethane. The organic phase was dried over sodium sulfate, filtered and concentrated in vacuo. Following chromatographic purification by means of preparative HPLC, and subsequent reaction with aqueous hydrochloric acid and freeze-drying, 21 mg (34%) of the title compound were obtained.

ES(+)-MS: 642.2 (3-(2-(4,4-Dimethyl-3-(4-(3-(2-methylphenyl)ureido)-3-methoxybenzyl)-2,5-dioxoimidazolidin-1-yl)-3-cyclopropylpropylamino)-3-phenylpropionic acid+H)⁺

Example 7

(R)-3-((S)-2-(4,4-Dimethyl-3-(4-(3-(2-methylphenyl)ureido)-3-methoxybenzyl)-2,5-dioxoimidazolidin-1-yl)-3-cyclopropylpropylamino)butanol hydrochloride

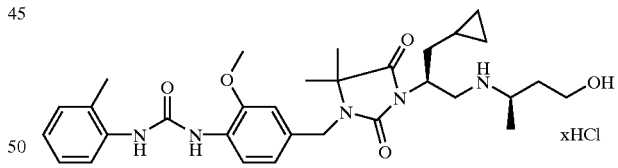

7a) tert-Butyl (R)-3-((S)-2-(4,4-dimethyl-3-(4-(3-(2-methylphenyl)ureido)-3-methoxybenzyl)-2,5-dioxoimidazolidin-1-yl)-3-cyclopropylpropionylamino)butyrate 626 mg (1.91 mmol) of TOTU and 308 μL (1.81 mmol) of diisopropylethylamine were added consecutively, while cooling with ice, to a solution of 974 mg (1.91 mmol) of the compound of example 1e) and 305 mg (1.91 mmol) of tert-butyl (R)-3-aminobutyrate in 10 mL of absolute DMF. After the mixture had been stirred at room temperature for 2 h, the solvent was removed in vacuo, the residue was dissolved in ethyl acetate and the ethyl acetate solution was washed consecutively, twice each, with an aqueous KHSO₄/

$K_2SO_4$ solution, a saturated $NaHCO_3$ solution and water. After the organic phase had been dried over sodium sulfate and filtered, the solvent was removed in vacuo and the residue was chromatographed over silica gel using ethyl acetate/heptane (1/1). Yield: 880 mg (71%).

7b) (R)-3-((S)-2-(4,4-Dimethyl-3-(4-(3-(2-methylphenyl) ureido)-3-methoxybenzyl)-2,5-dioxoimidazolidin-1-yl)-3-cyclopropylpropylamino)butanol hydrochloride 48 μL (0.38 mmol) of boron trifluoride etherate were added to 250 mg (0.38 mmol) of the compound of example 7a) in 4 mL of absolute THF. The reaction solution was heated to 80° C. and 760 μL (0.76 mmol) of a 1 M solution of borane-dimethyl sulfide in dichloromethane were added. After 4 h, the reaction mixture was treated with water and extracted with dichloromethane. The combined organic phases were dried over sodium sulfate. After filtration, removal of the solvent in vacuo, chromatographic purification by means of preparative HPLC, subsequent reaction with aqueous hydrochloric acid and freeze-drying, 120 mg (56%) of the title compound were obtained.

ES(+)-MS: 566.3 (3-(2-(4,4-Dimethyl-3-(4-(3-(2-methylphenyl)ureido)-3-methoxybenzyl)-2,5-dioxoimidazolidin-1-yl)-3-cyclopropylpropylamino) butanol+H)$^+$

Example 8

(S)-3-((S)-2-(4,4-Dimethyl-3-(4-(3-(2-methylphenyl) ureido)-3-methoxybenzyl)-2,5-dioxoimidazolidin-1-yl)-3-cyclopropylpropylamino)-3-phenylpropanol hydrochloride

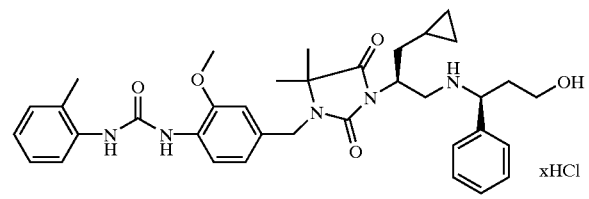

The compound was prepared in analogy with example 7. 35 mg (40%) of the title compound were obtained, in 2 mL of absolute THF, from 100 mg (0.14 mmol) of the initially prepared tert-butyl (S)-3-((S)-2-(4,4-Dimethyl-3-(4-(3-(2-methylphenyl)ureido)-3-methoxybenzyl)-2,5-dioxoimidazolidin-1-yl)-3-cyclopropylpropionylamino)-3-phenylpropionate, 18 μL (0.14 mmol) of boron trifluoride etherate and 280 μL (0.28 mmol) of a 1M solution of borane-dimethyl sulfide in dichloromethane.

ES(+)-MS: 628.3 (3-(2-(4,4-Dimethyl-3-(4-(3-(2-methylphenyl)ureido)-3-methoxybenzyl)-2,5-dioxoimidazolidin-1-yl)-3-cyclopropylpropylamino)-3-phenylpropanol+H)$^+$

Example 9

Ethyl (S)-3-((S)-2-(4,4-dimethyl-3-(4-(3-(2-methylphenyl)ureido)-3-methoxybenzyl)-2,5-dioxoimidazolidin-1-yl)-4-methylpentylamino)-3-phenylpropionate hydrochloride

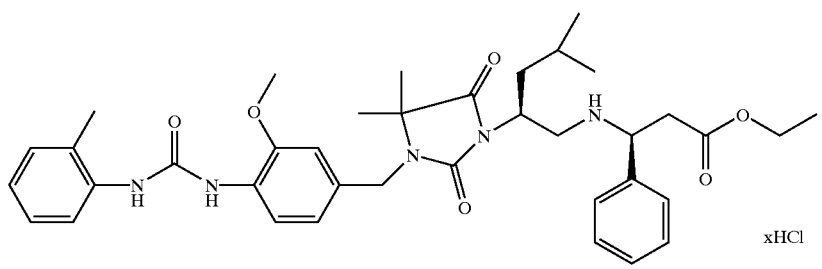

9a) (S)-2-(4,4-Dimethyl-3-(4-(3-(2-methylphenyl) ureido)-3-methoxybenzyl)-2,5-dioxoimidazolidin-1-yl)-4-methylpentanoic acid 16.5 mL of an n-butyllithium solution (2.5M in hexane) were added, under argon and at −40° C., to a solution of 5 g (20.66 mmol) of (S)-2-(4,4-dimethyl-2,5-dioxoimidazolidin-1-yl)-4-methylpentanoic acid (prepared in analogy with examples 1c) and 1d) using L-leucine in place of (S)-2-amino-3-cyclopropylpropionic acid) in 125 mL of absolute THF. The reaction mixture was allowed to warm to 0° C. and a solution of 6.28 g (20.66 mmol) of the compound of example 1b) in 40 mL of N-methyl-2-pyrrolidone and 20 mL of 1,3-dimethyl-2-imidazolidone was added. The reaction mixture was stirred at 0° C. for 1 h. 30 mL of 1N hydrochloric acid were then added and the THF was removed in vacuo. The residue was poured onto 300 mL of water. The precipitate was filtered off with suction, washed with water and taken up in dichloromethane. The solution was then added dropwise to 600 mL of methyl tert-butyl ether. The precipitate was filtered off and the organic phase was dried over magnesium sulfate. The desiccant was filtered off and the solvent was removed in vacuo. The residue was purified by means of preparative HPLC. 2.84 g (27%) of the title compound were obtained after concentrating the product fractions and subsequent freeze-drying.

9b) (S)-2-(4,4-Dimethyl-3-(4-(3-(2-methylphenyl) ureido)-3-methoxybenzyl)-2,5-dioxoimidazolidin-1-yl)-4,N-dimethyl-N-methoxypentanamide 1.89 mL (12.25 mmol) of diisopropylcarbodiimide and 1.65 g (12.25 mmol) of HOBT were added to a solution of 2.84 g (5.56 mmol) of the compound of example 9a) in 32 mL of absolute dichloromethane and 12 mL of acetonitrile. A solution of 1.35 g (13.9 mmol) of N,O-dimethylhydroxylamine hydrochloride and 2.36 mL (13.9 mmol) of diisopropylethylamine was then added dropwise at 0° C., and the reaction mixture was stirred at room temperature for 2 h. After it had been left to stand overnight, the mixture was poured onto 300 mL of saturated ammonium chloride solution. The phases were separated and the aqueous phase was extracted twice with dichloromethane. The combined organic phases were washed twice with saturated sodium hydrogencarbonate solution and dried over magnesium sulfate. After filtration, the solvent was removed in vacuo and the residue was chromatographed over silica gel using ethyl acetate/heptane (7/3). 2.62 g (88%) of the title compound were obtained after concentrating the product fractions in vacuo.

9c) (S)-2-(4,4-Dimethyl-3-(4-(3-(2-methylphenyl)ureido)-3-methoxybenzyl)-2,5-dioxoimidazolidin-1-yl)-4-methylpentanal The preparation was carried out as described in example 5b). The crude title compound was used directly in the subsequent reaction.

9d) Ethyl (S)-3-((S)-2-(4,4-dimethyl-3-(4-(3-(2-methylphenyl)ureido)-3-methoxybenzyl)-2,5-dioxoimidazolidin-1-yl)-4-methylpentylamino)-3-phenylpropionate hydrochloride A mixture of 2.48 g (5.01 mmol) of the compound of example 9c) and 1.93 g (10.03 mmol) of ethyl (S)-3-amino-3-phenylpropionate was hydrogenated over 200 mg of palladium/charcoal (10%) in absolute ethanol. After the reaction had come to an end, the catalyst was filtered off, the solvent was removed and the residue was chromatographed over silica gel using heptane/ethyl acetate (1/2). The product fractions were combined, freeze-dried and purified by means of preparative HPLC. The product fractions were combined, freeze-dried and taken up in dichloromethane. The dichloromethane solution was washed with saturated sodium hydrogencarbonate solution and dried over magnesium sulfate. After filtering and removing the solvent in vacuo, the residue was dissolved in acetonitrile/water; 2 equivalents of 1N hydrochloric acid were added and the mixture was freeze-dried. Yield: 850 mg (25%).

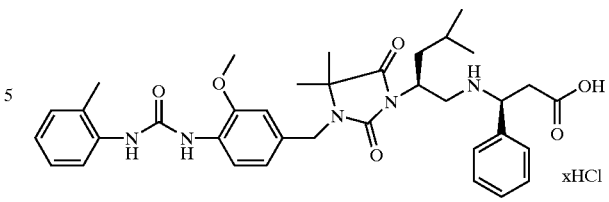

xHCl

ES(+)-MS: 672.5 (Ethyl 3-(2-(4,4-dimethyl-3-(4-(3-(2-methylphenyl)ureido)-3-methoxybenzyl)-2,5-dioxoimidazolidin-1-yl)-4-methylpentylamino)-3-phenylpropionate+H)$^+$ Example 10

(S)-3-((S)-2-(4,4-Dimethyl-3-(4-(3-(2-methylphenyl)ureido)-3-methoxybenzyl)-2,5-dioxoimidazolidin-1-yl)-4-methylpentylamino)-3-phenylpropionic acid hydrochloride A solution of 100 mg (0.149 mmol) of the compound of example 9 in 6N hydrochloric acid and THF was heated at 60° C. for 4 h. The THF was removed in vacuo and the residue was freeze-dried. Following purification by means of preparative HPLC, chromatography over silica gel using dichloromethane/methanol/acetic acid/water (9.5/0.5/0.05/0.05), concentrating the product fractions and freeze-drying in the presence of 2N hydrochloric acid, 20 mg (21%) of the title compound were obtained.

ES(+)-MS: 644.5 (3-(2-(4,4-Dimethyl-3-(4-(3-(2-methylphenyl)ureido)-3-methoxybenzyl)-2,5-dioxoimidazolidin-1-yl)-4-methylpentylamino)-3-phenylpropionic acid+H)$^+$ Example 11

Ethyl (R)-3-((S)-2-(4,4-dimethyl-3-(4-(3-(2-methylphenyl)ureido)-3-methoxybenzyl)-2,5-dioxoimidazolidin-1-yl)-4-methylpentylamino)butyrate hydrochloride

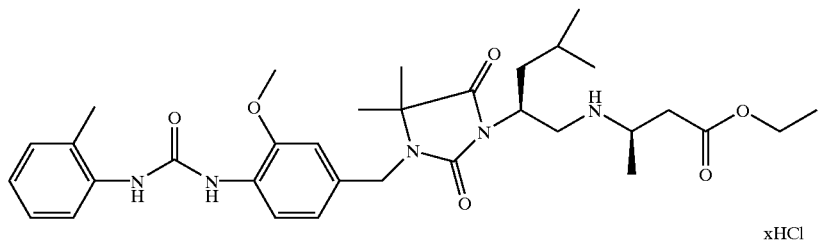

xHCl

The compound was prepared in analogy with example 9. From 2.2 g (4.44 mmol) of the compound of example 9c) and 1.16 g (8.89 mmol) of ethyl (R)-3-aminobutyrate, 140 mg (5%) of the title compound were obtained after purifying the crude product by chromatography over silica gel using ethyl acetate/heptane (2/1), concentrating the product fractions, freeze-drying, converting into the hydrochloride and purifying once again by chromatography over silica gel.

ES(+)-MS: 610.4 (Ethyl 3-(2-(4,4-dimethyl-3-(4-(3-(2-methylphenyl)ureido)-3-methoxybenzyl)-2,5-dioxoimidazolidin-1-yl)-4-methylpentylamino)butyrate+H)$^+$

Example 12

(R)-3-((S)-2-(4,4-Dimethyl-3-(4-(3-(2-methylphenyl)ureido)-3-methoxybenzyl)-2,5-dioxoimidazolidin-1-yl)-4-methylpentylamino)butyric acid hydrochloride

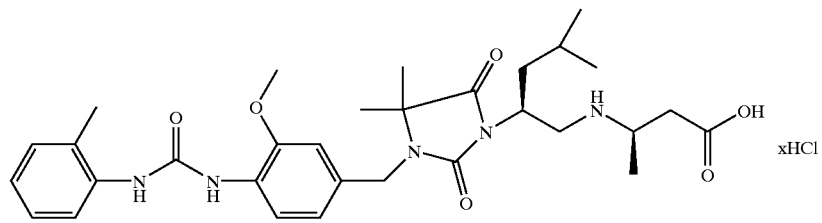

The compound was prepared in analogy with example 10. 17.5 mg (18%) of the title compound were obtained from 100 mg (0.164 mmol) of the compound of example 11.

ES(+)-MS: 582.5 (3-(2-(4,4-Dimethyl-3-(4-(3-(2-methylphenyl)ureido)-3-methoxybenzyl)-2,5-dioxoimidazolidin-1-yl)-4-methylpentylamino)butyric acid+H)$^+$

Example 13 tert-Butyl (S)-3-((S)-2-(4,4-dimethyl-3-(4-(3-(2-methylphenyl)ureido)-3-methoxybenzyl)-2,5-dioxoimidazolidin-1-yl)-3-cyclopropylpropylamino)-3-(3,4-dimethoxyphenyl)propionate

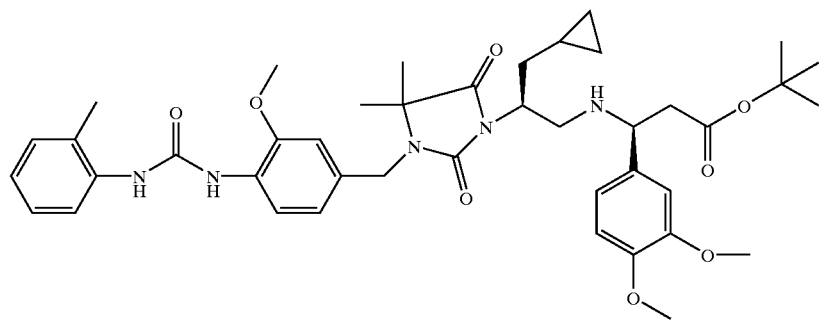

A solution of 285 mg (1.013 mmol) of tert-butyl (S)-3-amino-3-(3,4-dimethoxyphenyl)propionate (prepared in analogy with S. G. Davies et al., *Tetrahedron: Asymmetry* 2, 183 (1991) and *J. Chem. Soc. Perkin Trans* 1, 1129 (1994)) and 61 mg of acetic acid in 5 mL of methanol/acetic acid (99/1) was added to a solution of 499 mg (1.013 mmol) of the compound of example 1g) in 20 mL of methanol/acetic acid (99/1). 191 mg (3.039 mmol) of sodium cyanoborohydride were then added and the mixture was stirred at room temperature for 1 h. A further 64 mg (1.013 mmol) of sodium cyanoborohydride were added and the reaction mixture was stirred at room temperature for 1 h. Then 142 mg (0.507 mmol) of tert-butyl (S)-3-amino-3-(3,4-dimethoxyphenyl)propionate, 30 mg (0.507 mmol) of acetic acid and 64 mg (1.013 mmol) of sodium cyanoborohydride were added and the mixture was stirred at room temperature for 1 h. After a further 64 mg (1.013 mmol) of sodium cyanoborohydride had been added, the reaction mixture was stirred at room temperature for a further 1 h, after which it was adjusted to a pH of 4 by adding 1N hydrochloric acid. The methanol was removed in vacuo and the residue was extracted twice with dichloromethane. The combined organic phases were concentrated in vacuo. The residue was chromatographed over silica gel using ethyl acetate/heptane and then purified by means of preparative HPLC. 214 mg (28%) of the title compound were obtained after concentrating the product fractions and freeze-drying.

TOF ES(+)-MS: 758.44 (M+H)$^+$

Example 14

(S)-3-((S)-2-(4,4-Dimethyl-3-(4-(3-(2-methylphenyl)ureido)-3-methoxybenzyl)-2,5-dioxoimidazolidin-1-yl)-3-cyclopropylpropylamino)-3-(3,4-dimethoxyphenyl)propionic acid hydrochloride

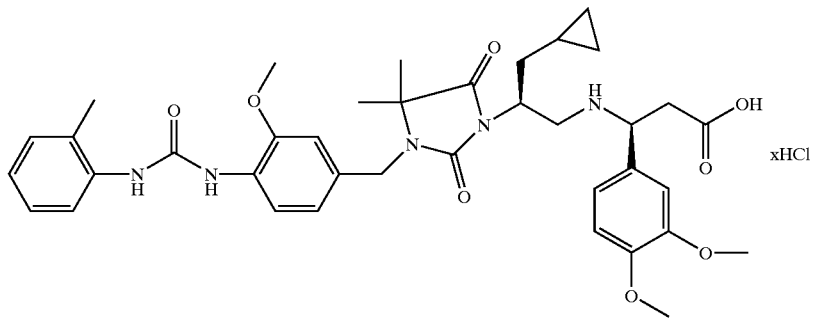

A solution of 214 mg (0.282 mmol) of the compound of example 13 in 10 mL of 90% trifluoroacetic acid was stirred at room temperature for 1.5 h. The trifluoroacetic acid was removed in vacuo and the residue was taken up in water/acetonitrile and freeze-dried. 210 mg (99%) of the title compound were obtained following conversion into the hydrochloride.

TOF ES(+)-MS: 702.41 (3-(2-(4,4-Dimethyl-3-(4-(3-(2-methylphenyl)ureido)-3-methoxybenzyl)-2,5-dioxoimidazolidin-1-yl)-3-cyclopropylpropylamino)-3-(3,4-dimethoxyphenyl)propionic acid+H)$^+$

Example 15

Isopropyl (S)-3-((S)-2-(4,4-dimethyl-3-(4-(3-(2-methylphenyl)ureido)-3-methoxybenzyl)-2,5-dioxoimidazolidin-1-yl)-3-cyclopropylpropylamino)-3-(3,4-dimethoxyphenyl)propionate hydrochloride The compound was prepared in analogy with example 13. From 499 mg (1.013 mmol) of the compound of example 1g) and 270 mg (1.013 mmol) of isopropyl (S)-3-amino-3-(3,4-dimethoxyphenyl)propionate (prepared from (S)-3-amino-3-(3,4-dimethoxyphenyl)propionic acid which was obtained by cleaving the corresponding tert-butyl ester), 227 mg (29%) of the title compound were obtained after purifying the crude product by chromatography using ethyl acetate/heptane (2/1), purifying by means of preparative HPLC and converting into the hydrochloride.

TOF ES(+)-MS: 744.48 (Isopropyl 3-(2-(4,4-dimethyl-3-(4-(3-(2-methylphenyl)ureido)-3-methoxybenzyl)-2,5-dioxoimidazolidin-1-yl)-3-cyclopropylpropylamino)-3-(3,4-dimethoxyphenyl)propionate+H)$^+$

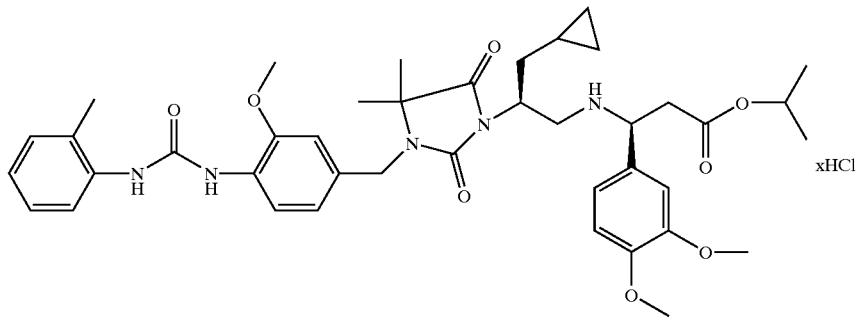

Example 16 tert-Butyl (S)-3-((S)-2-(4,4-dimethyl-3-(4-(3-(2-methylphenyl)ureido)-3-methoxybenzyl)-2,5-dioxoimidazolidin-1-yl)-3-cyclopropylpropylamino)-3-(3,4-methylenedioxyphenyl)propionate

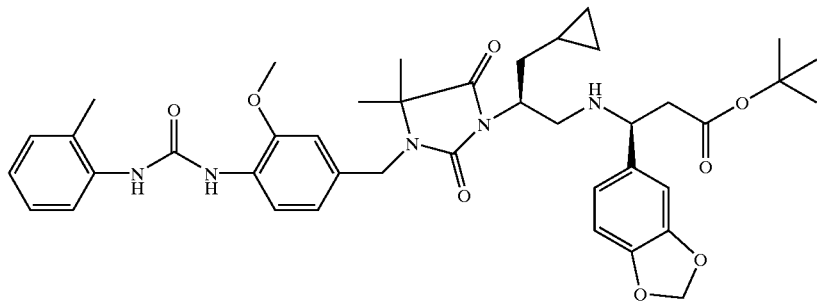

The compound was prepared in analogy with example 13. From 499 mg of the compound of example 1g) and 269 mg (1.013 mmol) of tert-butyl (S)-3-amino-3-(3,4-methylenedioxyphenyl)propionate (prepared in analogy with S. G. Davies et al., *Tetrahedron: Asymmetry* 2, 183 (1991) and *J. Chem. Soc. Perkin Trans* 1, 1129 (1994)), 233 mg (31%) of the title compound were obtained after chromatographic purification over silica gel using ethyl acetate/heptane (1/1), purification by means of preparative HPLC, concentrating the product fractions and freeze-drying.

TOF ES(+)-MS: 742.59 (M+H)$^+$

Example 17

(S)-3-((S)-2-(4,4-Dimethyl-3-(4-(3-(2-methylphenyl)ureido)-3-methoxybenzyl)-2,5-dioxoimidazolidin-1-yl)-3-cyclopropylpropylamino)-3-(3,4-methylenedioxyphenyl)propionic acid hydrochloride

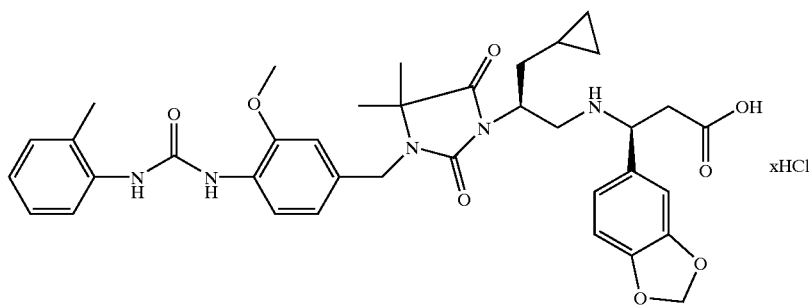

xHCl

A solution of 229 mg (0.309 mmol) of the compound of example 16 in 10 mL of 90% trifluoroacetic acid was left to stand at room temperature for 3 h. The trifluoroacetic acid was removed in vacuo and the residue was taken up in water/acetonitrile and freeze-dried. 181 mg (81%) of the title compound were obtained after converting into the hydrochloride.

TOF ES(+)-MS: 686.51 (3-(2-(4,4-Dimethyl-3-(4-(3-(2-methylphenyl)ureido)-3-methoxybenzyl)-2,5-dioxoimidazolidin-1-yl)-3-cyclopropylpropylamino)-3-(3,4-methylenedioxyphenyl)propionic acid+H)$^+$

Example 18

Isopropyl (S)-3-((S)-2-(4,4-dimethyl-3-(4-(3-(2-methylphenyl)ureido)-3-methoxybenzyl)-2,5-dioxoimidazolidin-1-yl)-3-cyclopropylpropylamino)-3-(3,4-methylenedioxyphenyl)propionate hydrochloride

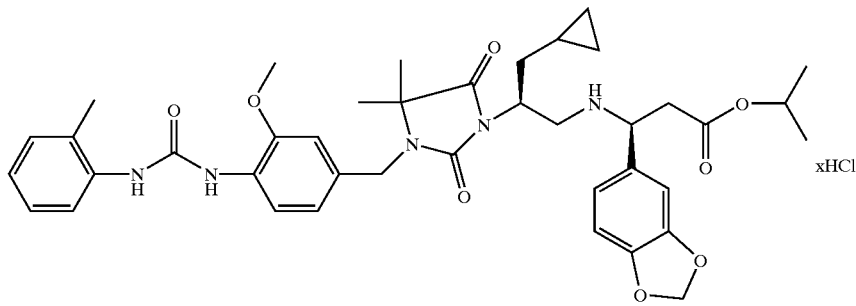

The compound was prepared in analogy with example 13. From 499 mg of the compound of example 1g) and 257 mg (1.013 mmol) of isopropyl (S)-3-amino-3-(3,4-methylenedioxyphenyl)propionate (prepared from (S)-3-amino-3-(3,4-methylenedioxyphenyl)propionic acid which was obtained by cleaving the corresponding tert-butyl ester), 185 mg (24%) of the title compound were obtained after purifying the crude product by chromatography using ethyl acetate/heptane (1/1), subsequently purifying by means of preparative HPLC and then converting into the hydrochloride.

TOF ES(+)-MS: 728.58 (Isopropyl 3-(2-(4,4-dimethyl-3-(4-(3-(2-methylphenyl)ureido)-3-methoxybenzyl)-2,5-dioxoimidazolidin-1-yl)-3-cyclopropylpropylamino)-3-(3,4-methylenedioxyphenyl)propionate+H)$^+$

Example 19

Ethyl (S)-3-((S)-2-(4,4-dimethyl-3-(4-(3-(2-methylphenyl)ureido)-3-methoxybenzyl)-2,5-dioxoimidazolidin-1-yl)-3-cyclopropylpropylamino)-3-(3,4-dimethoxyphenyl)propionate hydrochloride A solution of 500 mg (0.64 mmol) of the compound of example 15 in 40 mL of ethanol and 0.5 mL of concentrated hydrochloric acid was heated under reflux for 50 h. The reaction mixture was concentrated in vacuo, the residue was taken up in dichloromethane and the solution was washed with saturated sodium hydrogencarbonate solution, dried over sodium sulfate, filtered and concentrated. 200 mg (41%) of the title compound were obtained after purifying the crude product by chromatography over silica gel using ethyl acetate/heptane (1/1), purifying twice by means of preparative HPLC and converting into the hydrochloride.

TOF ES(+)-MS: 730.58 (Ethyl 3-(2-(4,4-dimethyl-3-(4-(3-(2-methylphenyl)ureido)-3-methoxybenzyl)-2,5-dioxoimidazolidin-1-yl)-3-cyclopropylpropylamino)-3-(3,4-dimethoxyphenyl)propionate+H)$^+$ Investigation of the Biological Activity A) U937/VCAM-1 Cell Adhesion Test (Assay for Measuring the Adhesion of U937 Cells (ATCC CRL 1593) to hVCAM-1 (1-3)-IqG)

The assay described below which is specific for the interaction between VCAM-1 and VLA-4, is used as the method for testing the activity of the compounds of the formula I on this interaction. The cellular binding partners, that is the VLA-4 integrins, are supplied in their natural form as surface molecules on human U937 cells (ATCC CRL 1593) which belong to the leukocyte group. The specific binding partners employed are recombinantly prepared soluble fusion proteins which consist of the extracytoplasmic domain of human VCAM-1 and the constant region of a human immunoglobulin of the IgG1 subclass.

1. Preparation of Human VCAM-1 (1-3)-IqG and Human CD4-IgG

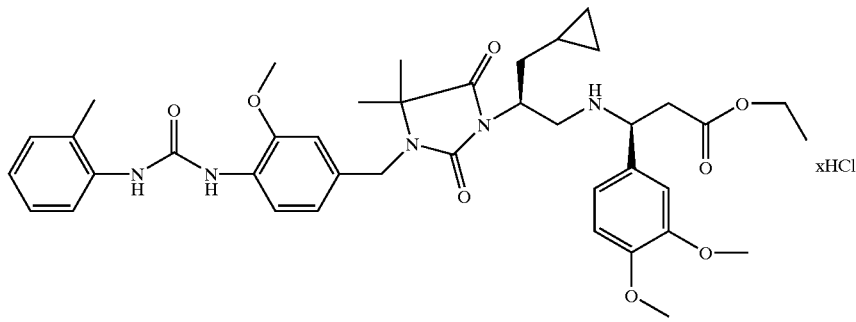

A gene construct for expressing the extracellular domain of human VCAM-1 linked to the gene sequence for the heavy chain of human immunoglobulin IgG1 (hinge, CH2 and CH3 regions) (from Dr. Brian Seed, Massachusetts General Hospital, Boston, USA; cf. Damle and Aruffo, *Proc. Natl. Acad. Sci. USA,* 1991, 88:6403) was employed. The soluble fusion protein hVCAM-1 (1-3)-IgG contained the three aminoterminal extracellular immunoglobulin-like domains of human VCAM-1 (Damle and Aruffo, *Proc. Natl. Acad. Sci. USA,* 1991, 88:6403). CD4-IgG (Zettimeissl et al., *DNA and Cell Biology,* 1990, 9:347) was used as the fusion protein for negative controls. The recombinant proteins were expressed as soluble proteins following the DEAE/dextran-mediated transfection of DNA into COS cells (ATCC CRL1651) using standard procedures (Ausubel et a., Current protocols in molecular biology, John Wiley & Sons, Inc., 1994).

2. Assay for Measuring the Adhesion of U937 Cells to hVCAM-1 (1-3)-IgG 2.1 96-well microtiter test plates (Nunc Maxisorb) containing 100 µL/well of a goat anti-human IgG antibody solution (10 µg/mL in 50 mM Tris, pH 9.5) were incubated at room temperature for 1 hour. After the antibody solution had been removed, the plates were washed once with PBS.

2.2 150 µL/well of a blocking buffer (1% BSA in PBS) were incubated on the plates at room temperature for 0.5 hour. After the blocking buffer had been removed, the plates were washed once with PBS.

2.3 100 µL/well of a cell culture supernatant from transfected COS cells were incubated on the plates at room temperature for 1.5 hours. The COS cells were transfected with a plasmid which encodes the three N-terminal immunoglobulin-like domains of VCAM-1 coupled to the Fc moiety of human IgG, (hVCAM-1(1-3)-IgG). The content of hVCAM-1 (1-3)-IgG was approximately 0.5–1 µg/mL. After the culture supernatant had been removed, the plates were washed once with PBS.

2.4 The plates were incubated with 100 µL/well of Fc receptor blocking buffer (1 mg/mL γ-globulin, 100 mM NaCl, 100 µM $MgCl_2$, 100 µM $MnCl_2$, 100 µM $CaCl_2$, 1 mg/mL BSA in 50 mM HEPES, pH 7.5) at room temperature for 20 minutes. After the Fc receptor blocking buffer had been removed, the plates were washed once with PBS.

2.5 20 µL of binding buffer (100 mM NaCl, 100 µM $MgCl_2$, 100 µM $MnCl_2$, 100 µM $CaCl_2$, 1 mg/mL BSA in 50 mM HEPES, pH 7.5) were introduced, the substances to be tested were added in 10 µL of binding buffer, and the plates were incubated for 20 minutes. Antibodies directed against VCAM-1 (BBT, No. BBA6) and against VLA-4 (Immunotech, No. 0764) were used as controls.

2.6 U937 cells were incubated in Fc receptor blocking buffer for 20 minutes and then pipetted in at a concentration of $1\times10^6$/mL and in a quantity of 100 µL per well (final volume: 125 µL/well).

2.7 The plates were slowly immersed, at an angle of 45°, into stop buffer (100 mM NaCl, 100 µM $MgCl_2$, 100 µM $MnCl_2$, 100 µM $CaCl_2$ in 25 mM Tris, pH 7.5) and excess liquid then removed by tapping. The procedure was repeated.

2.8 50 µL/well of a dye solution (16.7 µg/mL of Hoechst dye 33258, 4% formaldehyde, 0.5% Triton-X-100 in PBS)/well were then incubated on the plates for 15 minutes.

2.9 Excess liquid was removed from the plates by tapping and the plates were then slowly immersed, at an angle of 45°, into stop buffer (100 mM NaCl, 100 µM $MgCl_2$, 100 µM $MnCl_2$, 100 µM $CaCl_2$ in 25 mM Tris, pH 7.5). The procedure was repeated. The plates were then measured, with the liquid (stop buffer) present, in a cytofluorimeter (Millipore) (sensitivity: 5, filter: excitation wavelength: 360 nm, emission wavelength: 460 nm).

The intensity of the light emitted by the stained U937 cells is a measure of the number of the U937 cells which have adhered to the hVCAM-1 (1-3)-IgG and thus remained on the plate, and thus is a measure of the ability of the added test substance to inhibit this adhesion. The $IC_{50}$ concentration, which results in the adhesion being inhibited by 50%, was calculated from the inhibition of the adhesion observed at various concentrations of the test substance.

3. Results

The following results were obtained in the U937/VCAM-1 cell adhesion test ($IC_{50}$ values in nM (nanomol/liter)).

| Compound of example no. | $IC_{50}$ (nM) |
|---|---|
| 6 | 66.2 |
| 14 | 8.2 |
| 17 | 24.4 |

The pharmacological properties of the compounds of the formula I also can be investigated in the following models.

B) Leukocyte Adhesion in the Rat

In the rat leukocyte adhesion model, the ability of the compounds of the formula I to influence the adhesion of leukocytes is investigated in rat venules. The adhesion of leukocytes to the endothelium of post-capillary venules is regarded as being an important step in inflammation reactions (J. M. Harlan, *Blood,* 1985, 65:513). A well-coordinated dynamic sequence of events, in which chemotactic cytokines and cellular adhesion molecules play an active role, takes place when leukocytes are recruited from the blood into inflamed regions. It has been found that VCAM-1/VLA-4 interactions play a crucial role in the adhesion and emigration of leukocytes and in the increased permeability of blood vessels to macromolecules, which are induced by various mediator substances and cytokines (D. Seiffge, *Int. J. Microcirc.,* 1995, 15:301). In the present model, local or systemic injections of endotoxins, for example, zymosan, bacterial toxins such as lipopolysaccharides (LPS), or Freund's adjuvant, are used to elicit a generalized inflammation or rheumatoid arthritis, which leads to the leukocytes adhering and emigrating into affected organ regions. The increased adhesion, which is elicited by the endotoxin, to the endothelium of the venules is determined.

A camera inverted microscope (from Zeiss) which is fitted with a video system is used for determining the leukocyte adhesion. Zymosan or bacterial endotoxin is injected into male Sprague-Dawley rats (body weight: approximately 250 g) which have been given a light halothane premedication.

The control animals are given the same volume of 0.9% sodium chloride solution. The animals are then administered the test substance subcutaneously or orally as a single dose or in the form of multiple doses. For carrying out the measurement, the rats are anesthetized with an intramuscular injection of 1.25 g of urethane/kg. They are allowed to breathe spontaneously through an tracheal tube. A regulatable heating blanket is used to keep the body temperature at 37° C. The mesentery is carefully exposed through an abdominal opening, on a thermostated (37° C.) window in the microscope table, and covered with liquid paraffin at 37° C. The ileocecal region of the mesentery is held in position with the aid of three blunt needles and plasticine. After a 30-minute equilibration time, during which the tissue is allowed to stabilize, leukocyte adhesion is determined, in post-capillary venules of 20–30 μm in diameter and approximately 100 μm in length, by counting, in 2–3 segments of the venules, at intervals of 10 minutes over a period of 1 hour. A leukocyte is regarded as adhering to the endothelium when it is stationary for more than 30 seconds. After the experiment, the systemic leukocyte count, and the fibrinogen content of the blood, are determined. The inhibition of leukocyte adhesion brought about by the test substance is given by the decrease (in %) in the number of adherent leukocytes in the treated animals as compared with the number in the control animals.

C) Delayed-Type Hypersensitivity in the Mouse

The delayed-type hypersensitivity (DTH) model is used to investigate the antiallergic or antiinflammatory effect of the compounds of the formula I. DTH is an inflammatory reaction of the skin which is induced by sensitizing with antigenic substances. In order to determine in vivo the corresponding inflammatory reaction, and the recruitment of leukocytes into the inflamed regions, the substances are tested in the following mouse DTH model (see also T. B. Issekutz, *J. Immunol.*, 1991, 147:4178).

Groups of female BALB/c mice (body weight: approximately 20 g) are sensitized epicutaneously, on a shaved part of the skin, with 150 μL of a 3% solution of oxazolone, which induces a strong inflammatory DTH reaction. 6 days later, the reaction is challenged by administering 20 μL of a 1% oxazolone solution to the right ears of the animals. The test substances are in each case administered, subcutaneously or orally, 44 hours before the challenge of the reaction, 20 hours before the challenge of the reaction and 4 hours after the challenge of the reaction. Immediately before the challenge the reaction, and 24 after the challenge, a Mitutoyo Engineering micrometer is used to measure the change in the thickness in the right ear due to the inflammatory swelling of the ear. The difference between these two measurements is determined for each animal in the group. The mean values of the differences of an animal group treated with the test substance, on the one hand, and of an untreated control group, on the other hand, are compared. The percentage inhibition of the ear swelling is taken as a measure of the effect of the substance.

D) Antiasthmatic Effect in the Guinea Pig

The ability of the compounds of the formula I to influence lung function and their antiasthmatic effect can be determined in a guinea pig model which is based on the method described by G. Moacevic, *Arch. Toxicol.*, 1975, 34:1. The technical preparations for this investigation are carried out according to the details described by Moacevic. Male albino guinea pigs having a body weight of 300–500 g are used. The animals are placed in a plethysmograph (from FMI) and three initial values for the parameters respiratory frequency and respiratory amplitude are recorded. In this model, asthmatic respiration is characterized by a decrease in respiratory amplitude (i.e., decrease in respiratory volume due to bronchoconstriction) and an increase in respiratory frequency (i.e., reflex reaction). In asthmatic patients, this condition is known as dyspnea.

22 days before beginning the study, the albino guinea pigs are sensitized with an 0.1% solution of ovalbumin, 1 mL of which is administered per animal on two consecutive days. The experimental asthma attack is induced by the inhalation of an 0.3% ovalbumin solution for 1 minute. After a recovery phase of 40–60 minutes, the animals then inhale the test substance as an aqueous solution. Immediately after that, 0.3% ovalbumin solution is administered for 1 minute. In the following recovery phase of 30 minutes, the animals breathe normal air. This procedure is repeated twice. If the asthma attacks become life-threatening, the animals are administered oxygen.

The antiasthmatic effect in the sheep can be determined as described, for example, by Abraham et al., *J. Clin. Invest.*, 1994, 93:776.

E) The Antiatherosclerotic Effect can be Investigated in the Following Animal Models E1) Cuff Model of Neointima Formation The wild-type mice of the strain C57BL/6J are supplied by the breeding company Charles River Wiga GmbH (Sulzfeld), while the homozygous KO mice of the strain C57BL/6J-ApoE tm1Unc (ApoE KO) are supplied by The Jackson Laboratory (Maine, USA). All the mice are between 10 and 12 weeks of age at the beginning of the experiment and are kept in fully air-conditioned rooms at a temperature of 22° C. The day/night phases of the controlled light program are adjusted to periods of 12 hours in each case. The mice are first anesthetized with 60 mg of pentobarbital sodium/kg of body weight, which is given i.p. (i.e., intraperitoneally). Each animal was then additionally given 0.01 mg of xylazine/10 g of body weight, administered i.m. (i.e., intramuscularly).

The mice are fixed in the supine position and the inner surfaces of each of the two hind legs are shaved and disinfected. The skin on the inner side of the left thigh is now opened by means of a longitudinal incision of about 1 cm in length and the femoral artery is isolated from the surrounding tissue and from the femoral vein and the sciatic nerve. A piece of polyethylene tubing of about 2 mm in length (internal diameter 0.58 mm, external diameter 0.965 mm, Becton Dickinson, Sparks, Md., USA) is then cut open along its length and laid around the femoral artery and fixed using Prolene threads (7/0, 0.5 metric from Ethicon, Norderstedt). The skin is then closed once again using a continuous suture. The right hind leg is operated on in an analogous manner but without a cuff being placed around the femoral artery. The animal is subsequently returned to its cage. From the time of the operation onward, the animals are treated daily with the test substance.

At the end of the experiment, the mice are once again anesthetized with 60 mg of pentobarbital sodium/kg of body weight, given i.p., and 0.01 mg of xylazine/10 g of body weight, given i.m. In order to fix the vessels in situ, each mouse is then given an injection of 4% formalin solution into the abdominal aorta. The right and left femoral arteries are then removed. The section of the artery which encompasses the region about 1 mm proximal to the cuff, the section enclosed by the cuff itself, and the vascular region 1 mm distal to the cuff, is removed on the left side. On the right side, this section corresponds to the region which is only isolated, but not enclosed by a cuff, during the operation.

The sections of the left and right femoral artery, which had been fixed in 4% formalin solution, are now embedded in paraffin. Several sections, which are subsequently stained with hematoxylin and eosin for software-assisted (LeicaQWin from Leica Imaging Systems, Cambridge, GB) morphometric analysis, are prepared from the region of the left artery surrounded by the cuff and from the corresponding region of the right control artery.

Three tissue sections from the cuff-surrounded region of the left femoral artery, and three sections from the corresponding region of the right control artery, are evaluated per mouse. After marking of the external elastic lamina, the internal elastic lamina and the boundary between the lumen and the endothelium, the analytical program calculates the following areas: lumen, neointima and media. The sizes of these areas are given in the unit $\mu m^2$. The effect of a compound is indicated by the reduction in the neointima/media ratio as compared with the control group.

E2) Heart Transplantation

In the allogenic heart transplantation model, transplantations are carried out between two genetically incompatible rat strains. For this, Wistar-Furth rats are used as donor animals and Lewis rats are used as recipient animals. The animals are obtained from the breeding company Charles River Wiga GmbH (Sulzfeld, Germany). Male Lewis rats weighing 270–330 g and aged from 2.5 to 3 months, and male Wistar-Furth rats weighing 200–250 g and aged from 1.5 to 2 months, are kept under constant, controlled conditions (temperature 19–22° C.; relative atmospheric humidity 50–55%; the day/night phases of the controlled light program are adjusted to periods of 12 hours each).

For the operation, the rats are given a combination of 3.3 mg of xylazine/kg of body weight and 115 mg of ketamine/kg of body weight. After the anesthetic has taken effect, the abdomen of the recipient is opened by median incision. The abdominal aorta and the inferior vena cava are separated from each other between the renal artery and vein and the ileolumbar vessels. The aorta is subsequently closed cranially using a vessel clip. At the caudal end, a silk thread is laid around the two vessels and drawn tight. A second silk thread is laid loosely around the cranial end of the inferior vena cava. The donor animal is sacrificed, after the abdominal cavity has been opened, by cutting through the large abdominal blood vessels. This point in time signaled the beginning of the period during which the donor organ was ischemic. The diaphragm is then opened and the heart exposed. The superior and inferior vena cava are ligated and cut through on the side distal to the heart. A silk thread was then used to perform a mass ligature on the pulmonary veins. The pulmonary aorta and artery are then lifted with forceps and cut through. The transplant is now freed from blood residues in the vascular system. The heart is then lifted, separated, together with the mass ligature, from the lung and stored for from one to two minutes in cold physiological NaCl solution. An end-to-side anastomosis of the aorta and the pulmonary artery of the donor organ to the abdominal artery and the inferior vena cava, respectively, of the recipient animal is then performed. After the vessel anastomoses have been completed, the venous circulation, followed by the arterial circulation, are then opened consecutively. Finally, the abdominal cavity is sealed once again using a peritoneum/muscle suture and a skin suture. Following the opening-up of the blood circulation and a brief recovery phase, the transplanted heart beats with a sinus frequency of from approximately 100 to 120 beats/minute. For immunosuppression, cyclosporin A (CSA) is administered either subcutaneously (s.c.) or orally via the drinking water. After the acute rejection period has been surmounted, the dose of 25 mg/kg of body weight can be reduced, from the 15th day p.op. (i.e., post operationem) onward, down to 5 mg/kg of body weight. The injections are performed once a day in the morning in the region of the nape of the neck in the animals.

The change-over from subcutaneous CSA administration to oral CSA administration takes place on the 22nd day p.op., in order to be certain of having surmounted the acute rejection period. The substance to be investigated is administered over a period of 100 days, from the time of the operation onward. After the period of observation (100 days) has come to an end, the animals are anesthetized and the abdominal cavity is opened. The heart is then removed from the abdominal vessels, while preserving the vessel stumps, then cut into slices and stored in 4% formalin solution. After the heart slices have been fixed, they are embedded in paraffin and stained for elastica using van Gieson's standardized histological technique. The neointimal proliferation, and the narrowing of the vascular lumen which is associated therewith, is classified in accordance with Adams et al. (*Transplantation*, 1993, 56:794). Increased tissue formations between the internal elastic lamina and the endothelium are classified. Van Gieson's special stain, which selectively emphasizes the elastic fibers, facilitates the assessment. The effect of a compound is indicated by the reduction in neointimal proliferation, and thus in transplant atherosclerosis, as compared with the control group.

E3) Atherosclerosis Model in ApoE Knock-Out(KO) Mice

The homozygous KO mice of the strain C57BL/6J-ApoE tm1Unc (ApoE KO) are supplied by The Jackson Laboratory (Maine, USA). At the beginning of the experiment, all the mice are between 10 and 12 weeks of age and are kept on standard litter for laboratory animals (Altromin, Lage) in fully air-conditioned rooms at a temperature of 22° C. The day/night phases of the controlled light program are adjusted to a period of 12 hours each. The animals are treated with the test substance for 4 months.

At the end of the experiment, the mice are anesthetized with 60 mg of pentobarbital sodium/kg of body weight, given i.p., and 0.01 mg of xylazine/10 g of body weight, given i.m. The heart and aortic arch, and also the descending thoracic aorta, are then removed and fixed in 4% formalin solution. The descending aorta is treated with Oil Red O, for staining fat lesions. The morphometric analysis of the fat lesions is performed using a microscope (Leitz DM RBE type, from Leica, Bensheim), a camera which is connected to it and which possesses a control unit (CF 15 MCC type, Kappa Messtechnik, Gleichen) and a computer (Leica, Bensheim). The measurements are performed using a computer program for the image analysis (LeicaQWin from Leica Imaging Systems, Cambridge, GB). The heart and the aortic arch are cut longitudinally and stained with hematoxylin and eosin for the morphometric analysis. 15–20 sections are evaluated in each case. Further sections are examined immunohistochemically for macrophages and T lymphocytes. The effect of a compound is indicated by the reduction in plaque formation in the aorta as compared with the control group.

F) The Cardioprotective Effect can be Investigated, for Example, in the Following Animal Model.

Cardiac Infarct Size in the Rat

Male Wistar rats aged from 2.5 to 3 months and having a body weight of 270–330 g are obtained from the breeding company Charles River Wiga GmbH (Sulzfeld, Germany). The animals are kept under constant, controlled conditions (temperature 19–22° C.; relative atmospheric humidity 50–55%; the day/night phases of the controlled light program are adjusted to periods of 12 hours each). For the operation, the rats are given a combination of 3.3 mg of xylazine/kg of body weight and 115 mg of ketamine/kg of body weight. The animals are subsequently intubated and ventilated using 30% oxygen. The thorax is shaved, disinfected and opened by means of a left-lateral thoracotomy. The left coronary artery is either ligated permanently, for 48 hours or for 4 weeks, 2–3 mm below the left auricular appendix, or else it is ligated for 30 minutes and reperfused for 47.5 hours or for 4 weeks.

After the operation, the thorax is closed again and the animals are extubated once spontaneous respiration has begun. The test substance is administered 30 minutes after the ligation or immediately before the reperfusion. The animals are then treated daily with the test substance. At the end of the experiment, the animals are once again anesthetized with a combination of 3.3 mg of xylazine/kg of body weight and 115 mg of ketamine/kg of body weight. For the wall movement analysis, the animals whose hearts were reperfused are examined by means of nuclear magnetic resonance imaging. In the case of animals whose hearts were not reperfused, a tip catheter, for measuring the ventricular pressure and contractility, is introduced, via carotid artery, into the left ventricle. After that, the hearts of all the animals are removed and perfused in a Langendorff apparatus, in a retrograde manner, via the aorta, with 1% Evans Blue solution at 37° C., in order to determine the anatomic area at risk and the nonischemic area. Subsequently, the hearts are cut into 5–6 thin slices and incubated for 15 minutes in 2,3,5-triphenyltetrazolium chloride solution for the purpose of determining the vital heart tissue and the dead heart tissue. The planimetric analysis of the area at risk and of the infarction region is performed using a camera (Leica, Bensheim) and an attached computer unit with analytical software (Leitz, Bensheim). The area at risk is expressed in percent based on the left ventricle plus septum and the infarction region in percent based on the area at risk. The effect of a compound is indicated by the reduction in the infarction region based on the area at risk as compared with the control group.

What is claimed is:

1. A compound of the formula I,

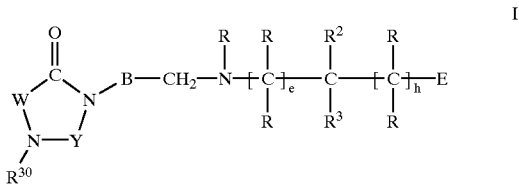

wherein

W is $R^1$-A-C($R^{13}$) or $R^1$-A-C($R^{13}$)=C,

Y is a carbonyl group or thiocarbonyl group;

A is a direct linkage, ($C_1$–$C_6$)-alkylene, or ($C_3$–$C_7$)-cycloalkylene;

B is selected from the group consisting of($C_1$–$C_6$)-alkylene, ($C_2$–$C_6$)-alkenylene, phenylene, phenylene-($C_1$–$C_3$)-alkyl, ($C_1$–$C_3$)-alkylenephenyl, and ($C_1$–$C_3$)-alkylenephenyl-($C_1$–$C_3$)-alkyl, wherein the ($C_1$–$C_6$)-alkylene group and the ($C_2$–$C_6$)-alkenylene group are unsubstituted or substituted by one or more identical or different groups selected from the group consisting of ($C_1$–$C_8$)-alkyl, ($C_2$–$C_8$)-alkenyl, ($C_2$–$C_8$)-alkynyl, ($C_3$–$C_{10}$)-cycloalkyl, ($C_3$–$C_{10}$)-cycloalkyl-($C_1$–$C_6$-alkyl, optionally substituted ($C_6$–$C_{14}$)-aryl, and ($C_6$–$C_{14}$)-aryl-($C_1$–$C_6$)-alkyl which is optionally substituted in the aryl group;

E is tetrazolyl, $R^{10}$CO, HCO, $R^8$O—$CH_2$, $R^8$CO—O—$CH_2$, $R^{8a}$O—CO—O—$CH_2$, or ($R^8$O)$_2$P(O)—O—$CH_2$;

R is hydrogen, ($C_1$–$C_8$)-alkyl, ($C_3$–$C_{12}$)-cycloalkyl, ($C_3$–$C_{12}$)-cycloalkyl-($C_1$–$C_8$)-alkyl, optionally substituted ($C_6$–$C_{14}$)-aryl, or ($C_6$–$C_{14}$)-aryl-($C_1$–$C_8$)-alkyl which is optionally substituted in the aryl group, wherein all the groups R are independent of each other, and the groups R can be identical or different;

$R^1$ is hydrogen, ($C_1$–$C_{10}$)-alkyl which can be optionally monosubstituted or polysubstituted by fluorine, ($C_3$–$C_{12}$)-cycloalkyl, or ($C_3$–$C_{12}$)-cycloalkyl-($C_1$–$C_8$)-alkyl;

$R^2$ is hydrogen or ($C_1$–$C_8$)-alkyl;

$R^3$ is hydrogen, ($C_1$–$C_{10}$)-alkyl which can be optionally monosubstituted or polysubstituted by fluorine, optionally substituted ($C_6$–$C_{14}$)-aryl, ($C_6$–$C_{14}$)-aryl-($C_1$–$C_8$) alkyl which is optionally substituted in the aryl group, or ($C_3$–$C_8$)-cycloalkyl;

$R^8$ is hydrogen, ($C_1$–$C_{10}$)-alkyl, optionally substituted ($C_6$–$C_{14}$)-aryl or ($C_6$–$C_{14}$)-aryl-($C_1$–$C_8$)-alkyl optionally substituted in the aryl group, wherein the groups $R^8$ are independent of each other and can be identical or different;

$R^{8a}$ has, independently of $R^8$, one of the meanings of $R^8$ with the exception of hydrogen;

$R^{10}$ is hydroxyl, ($C_1$–$C_{10}$)-alkoxy, ($C_6$–$C_{14}$)-aryl-($C_1$–$C_8$)-alkoxy optionally substituted in the aryl group, optionally substituted ($C_6$–$C_{14}$-aryloxy, ($C_1$–$C_8$)-alkylcarbonyloxy-($C_1$–$C_6$)-alkoxy, ($C_6$–$C_{14}$)- arylcarbonyloxy-$(C_1-C_6)$-alkoxy which is optionally substituted in the aryl group, $(C_6-C_{14})$-aryl-$(C_1-C_6)$-alkylocarbonyloxy-$(C_1-C_6)$-alkoxy which is optionally substituted in the aryl group, $(C_1-C_8)$-alkoxycarbonyloxy-$(C_1-C_6)$-alkoxy, $(C_6-C_{14})$-aryloxycarbonyloxy-$(C_1-C_6)$-alkoxy which is optionally substituted in the aryl group, $(C_6-C_{14})$-aryl-$(C_1-C_6)$-alkoxycarbonyloxy-$(C_1-C_6)$-alkoxy which is optionally substituted in the aryl group, amino, mono- or di-$((C_1-C_{10})$-alkyl)amino, or $R^8R^8N$—CO—$(C_1-C_6)$-alkoxy in which the groups are independent of each other and can be identical or different;

$R^{13}$ is hydrogen, $(C_1-C_6)$-alkyl which can be optionally monosubstituted or polysubstituted by fluorine, optionally substituted $(C_6-C_{14})$-aryl, $(C_6-C_{14})$-aryl-$(C_1-C_6)$-alkyl which is optionally substituted in the aryl group, $(C_3-C_8)$-cycloalkyl, or $(C_3-C_8)$-cycloalkyl-$(C_1-C_6)$-alkyl;

$R^{30}$ is one of the groups $R^{32}(R)N$—CO—N(R)—$R^{31}$, $R^{32}(R)N$—CS—N(R)—$R^{31}$, $R^{32}(R)N$—S(O)$_n$—N(R)—$R^{31}$, $R^{32}$—CO—N(R)—$R^{31}$, $R^{32}$—CS—N(R)—$R^{31}$, $R^{32}$—S(O)$_n$—N(R)—$R^{31}$, $R^{32}(R)N$—CO—$R^{31}$, $R^{32}(R)N$—CS—$R^{31}$, $R^{32}(R)N$—S(O)$_n$—$R^{31}$, $R^{32}$—CO—$R^{31}$, $R^{32}$—CS—$R^{31}$, $R^{32}$—S(O)$_n$—$R^{31}$ or $R^{12a}$—O—CO—N(R)—$R^{31}$;

$R^{31}$ is the divalent group —$R^{33}$—$R^{34}$—$R^{35}$—$R^{36}$—, wherein $R^{36}$ is bonded to the nitrogen atom in the imidazolidine ring in the formula I;

$R^{32}$ is hydrogen, $(C_1-C_8)$-alkyl which can be optionally substituted by from 1 to 8 fluorine atoms, $(C_2-C_8)$-alkenyl, $(C_2-C_8)$-alkynyl, $(C_3-C_{12})$-cycloalkyl, $(C_3-C_{12})$-cycloalkyl-$(C_1-C_8)$-alkyl, $(C_6-C_{12})$-bicycloalkyl, $(C_6-C_{12})$-bicycloalkyl-$(C_1-C_8)$-alkyl, $(C_6-C_{12})$-tricycloalkyl, $(C_6-C_{12})$-tricycloalkyl-$(C_1-C_8)$-alkyl, optionally substituted $(C_6-C_{14})$-aryl, or $(C_6-C_{14})$-aryl-$(C_1-C_8)$-alkyl which is optionally substituted in the aryl group;

$R^{33}$ is a direct linkage or a divalent $(C_1-C_6)$-alkylene group;

$R^{34}$ is selected from the group consisting of $(C_1-C_8)$-alkylene, $(C_3-C_{12})$-cycloalkylene, $(C_6-C_{12})$-bicycloalkylene, $(C_6-C_{12})$-tricycloalkylene, and optionally substituted $(C_6-C_{14})$-arylene;

$R^{35}$ is a direct linkage or a divalent $(C_1-C_8)$-alkylene group;

$R^{36}$ is a direct linkage, the group —CO—, or the group —S(O)$_n$—;

e and h are, independently of each other, 0 or 1;

n is 1 or 2, wherein, when they occur more than once, the numbers n are independent of each other and can be identical or different;

in any of its stereoisomeric forms or mixtures thereof in any ratio, or its physiologically tolerated salts.

2. The compound of claim 1, wherein W is $R^1$-A-C($R^{13}$)

Y is a carbonyl group or thiocarbonyl group;

A is a direct linkage, $(C_1-C_6)$-alkylene, or $(C_3-C_7)$-cycloalkylene;

B is selected from the group consisting of $(C_1-C_6)$-alkylene, $(C_2-C_6)$-alkenylene, phenylene, phenylene-$(C_1-C_3)$-alkyl, $(C_1-C_3)$-alkylenephenyl, and $(C_1-C_3)$-alkylene-phenyl-$(C_1-C_3)$-alkyl, wherein the $(C_1-C_6)$-alkylene group and the $(C_2-C_6)$-alkenylene group are unsubstituted or are substituted by one or more identical or different groups selected from the group consisting of $(C_1-C_8)$-alkyl, $(C_2-C_8)$-alkenyl, $(C_2-C_8)$-alkynyl, $(C_3-C_{10})$-cycloalkyl, $(C_3-C_{10})$-cycloalkyl-$(C_1-C_6)$-alkyl, optionally substituted $(C_6-C_{14})$-aryl, and $(C_6-C_{14})$-aryl-$(C_1-C_6)$-alkyl which is optionally substituted in the aryl group;

E is $R^8OCH_2$, $R^8CO$—OCH$_2$, or $R^{10}CO$;

R is hydrogen, $(C_1-C_8)$-alkyl, $(C_3-C_{12})$-cycloalkyl, $(C_3-C_{12})$-cycloalkyl-$(C_1-C_8)$-alkyl, optionally substituted $(C_6-C_{14})$-aryl or $(C_6-C_{14})$-aryl-$(C_1-C_8)$-alkyl which is optionally substituted in the aryl group, wherein all the groups R are independent of each other and the groups R can be identical or different;

$R^1$ is hydrogen, $(C_1-C_{10})$-alkyl which can be optionally monosubstituted or polysubstituted by fluorine, $(C_3-C_{12})$-cycloalkyl, or $(C_3-C_{12})$-cycloalkyl-$(C_1-C_8)$-alkyl;

$R^2$ is hydrogen or $(C_1-C_8)$-alkyl;

$R^3$ is hydrogen, $(C_1-C_8)$-alkyl, optionally substituted $(C_6-C_{14})$-aryl-, $(C_6-C_{14})$-aryl-$(C_1-C_8)$-alkyl which is optionally substituted in the aryl group, or $(C_3-C_8)$-cycloalkyl;

$R^8$ is hydrogen, $(C_1-C_{10})$-alkyl, optionally substituted $(C_6-C_{14})$-aryl or $(C_6-C_{14})$-aryl-$(C_1-C_8)$-alkyl optionally substituted in the aryl group, wherein the groups $R^8$ are independent of each other;

$R^{10}$ is hydroxyl, $(C_1-C_8)$-alkoxy, $(C_6-C_{12})$-aryl-$(C_1-C_8)$-alkoxy optionally substituted in the aryl group, optionally substituted $(C_6-C_{12})$-aryloxy, $(C_1-C_8)$-alkylcarbonyloxy-$(C_1-C_6)$-alkoxy, $(C_6-C_{12})$-aryl-$(C_1-C_6)$-alkylcarbonyloxy-$(C_1-C_6)$-alkoxy which is optionally substituted in the aryl group, $(C_1-C_8)$-alkoxycarbonyloxy-$(C_1-C_6)$-alkoxy, $(C_6-C_{12})$-aryl-$(C_1-C_6)$-alkoxycarbonyloxy-$(C_1-C_6)$-alkoxy which is optionally substituted in the aryl group, amino, mono- or di-$((C_1-C_{10})$-alkyl)amino, or $R^8R^8N$—CO—$(C_1-C_6)$-alkoxy wherein the groups $R^8$ are independent of each other and can be identical or different;

$R^{13}$ is hydrogen, $(C_1-C_6)$-alkyl which can be optionally monosubstituted or polysubstituted by fluorine, optionally substituted $(C_6-C_{14})$-aryl, $(C_6-C_{14})$-aryl-$(C_1-C_6)$-alkyl which is optionally substituted in the aryl group, $(C_3-C_8)$-cycloalkyl or $(C_3-C_8)$-cycloalkyl-$(C_1-C_6)$-alkyl;

$R^{30}$ is one of the groups $R^{32}(R)N$—CO—N(R)—$R^{31}$, $R^{32}(R)N$—CS—N(R)—$R^{31}$, $R^{32}$—CO—N(R)—$R^{31}$, $R^{32}$—CS—N(R)—$R^{31}$, $R^{32}(R)N$—CO—$R^{31}$, or $R^{32}(R)N$—CS—$R^{31}$;

$R^{31}$ is —$R^{33}$—$R^{34}$—$R^{35}$—$R^{36}$—, wherein $R^{36}$ is bonded to the nitrogen atom in the imidazolidine ring in the formula I;

$R^{32}$ is hydrogen, $(C_1-C_8)$-alkyl which can be optionally substituted by from 1 to 8 fluorine atoms, $(C_2-C_8)$-alkenyl, $(C_2-C_8)$-alkynyl, $(C_3-C_{12})$-cycloalkyl, $(C_3-C_{12})$-cycloalkyl-$(C_1-C_8)$-alkyl, $(C_6-C_{12})$-bicycloalkyl, $(C_6-C_{12})$-bicycloalkyl-$(C_1-C_8)$-alkyl, $(C_6-C_{12})$-tricycloalkyl, $(C_6-C_{12})$-tricycloalkyl-$(C_1-C_8)$-alkyl, optionally substituted $(C_6-C_{14})$-aryl, or $(C_6-C_{14})$-aryl-$(C_1-C_8)$-alkyl which is optionally substituted in the aryl group;

$R^{33}$ is a direct linkage or a divalent $(C_1-C_6)$-alkylene group;

$R^{34}$ is selected from the group consisting of $(C_1-C_8)$-alkylene, $(C_3-C_{12})$-cycloalkylene, $(C_6-C_{12})$-bicycloalkylene, $(C_6-C_{12})$-tricycloalkylene, and optionally substituted $(C_6-C_{14})$-arylene;

$R^{35}$ is a direct linkage or a divalent $(C_1-C_8)$-alkylene group;

$R^{36}$ is a direct linkage;

e and h are, independently of each other, 0 or 1;

in any of its stereoisomeric forms or mixtures thereof in any ratio, or its physiologically tolerated salts.

3. The compound of claim 1, wherein

W is $R^1$-A-C($R^{13}$);

Y is a carbonyl group;

A is a direct linkage or $(C_1-C_6)$-alkylene;

B is a divalent methylene group, wherein the methylene group is unsubstituted or is substituted by one or two identical or different groups selected from the group consisting of $(C_1-C_8)$-alkyl, $(C_3-C_6)$-cycloalkyl-$(C_1-C_6)$-alkyl, and $(C_6-C_{10})$-aryl-$(C_1-C_6)$-alkyl which is optionally substituted in the aryl group;

E is $R^{10}$CO, HO—$CH_2$, or $R^8$CO—O—$CH_2$;

R is hydrogen or $(C_1-C_8)$-alkyl, wherein all the groups R are independent of each other and the groups R can be identical or different;

$R^1$ is hydrogen or $(C_1-C_{10})$-alkyl which can be optionally monosubstituted or polysubstituted by fluorine;

$R^2$ is hydrogen;

$R^3$ is hydrogen, $(C_1-C_8)$-alkyl which can be optionally substituted by from 1 to 6 fluorine atoms, optionally substituted $(C_6-C_{10})$-aryl, $(C_6-C_{10})$-aryl-$(C_1-C_6)$-alkyl which is optionally substituted in the aryl group, or $(C_3-C_8)$-cycloalkyl;

$R^8$ is hydrogen, $(C_1-C_6)$-alkyl, or phenyl-$(C_1-C_4)$-alkyl which is optionally substituted in the phenyl group;

$R^{10}$ is hydroxyl, $(C_1-C_8)$-alkoxy, $(C_6-C_{10})$-aryl-$(C_1-C_6)$-alkoxy optionally substituted in the aryl group, optionally substituted $(C_6-C_{10})$-aryloxy, $(C_1-C_6)$-alkylcarbonyloxy-$(C_1-C_6)$-alkoxy, or $(C_1-C_6)$-alkoxycarbonyloxy-$(C_1-C_6)$-alkoxy;

$R^{13}$ is hydrogen or $(C_1-C_6)$-alkyl which can be optionally monosubstituted or polysubstituted by fluorine;

$R^{30}$ is one of the groups $R^{32}$(R)N—CO—N(R)—$R^{31}$ or $R^{32}$(R)N—CS—N(R)—$R^{31}$;

$R^{31}$ is —$R^{33}$—$R^{34}$—$R^{35}$—$R^{36}$—, wherein $R^{36}$ is bonded to the nitrogen atom in the imidazolidine ring in the formula I;

$R^{32}$ is hydrogen, $(C_1-C_6)$-alkyl which can be optionally substituted by from 1 to 6 fluorine atoms, optionally substituted $(C_6-C_{10})$-aryl or $(C_6-C_{10})$-aryl-$(C_1-C_6)$-alkyl which is optionally substituted in the aryl group;

$R^{33}$ is a direct linkage or a divalent $(C_1-C_4)$-alkylene group;

$R^{34}$ is selected from the group consisting of $(C_1-C_6)$-alkylene, $(C_5-C_6)$-cycloalkylene and optionally substituted $(C_6-C_{10})$-arylene;

$R^{35}$ is a direct linkage or a divalent $(C_1-C_4)$-alkylene group;

$R^{36}$ is a direct linkage;

e and h are, independently of each other, 0 or 1;

in any of its stereoisomeric forms or mixtures thereof in any ratio, or its physiologically tolerated salts.

4. The compound of claim 1, wherein

W is $R^1$-A-C($R^{13}$);

Y is a carbonyl group;

A is direct linkage;

B is a divalent methylene group which is substituted by isobutyl or cyclopropylmethyl;

E is $R^{10}$CO or HO—$CH_2$;

R is hydrogen;

$R^1$ is methyl or trifluoromethyl;

$R^2$ is hydrogen;

$R^3$ is hydrogen, $(C_1-C_8)$-alkyl which can be optionally substituted by from 1 to 6 fluorine atoms, optionally substituted $(C_6-C_{10})$-aryl, $(C_6-C_{10})$-aryl-$(C_1-C_4)$-alkyl which is optionally substituted in the aryl residue, or $(C_3-C_8)$-cycloalkyl;

$R^{10}$ is hydroxyl, $(C_1-C_8)$-alkoxy, $(C_6-C_{10})$-aryl-$(C_1-C_6)$-alkoxy optionally substituted in the aryl group, optionally substituted $(C_6-C_{10})$-aryloxy, $(C_1-C_6)$-alkylcarbonyloxy-$(C_1-C_6)$-alkoxy or $(C_1-C_6)$-alkoxycarbonyloxy-$(C_1-C_6)$-alkoxy;

$R^{13}$ is methyl or trifluoromethyl;

$R^{30}$ is one of the groups $R^{32}$(R)N—CO—N(R)—$R^{31}$ or $R^{32}$(R)N—CS—N(R)—$R^{31}$;

$R^{31}$ is phenylenemethyl which is optionally substituted in the phenyl group, wherein the methyl group of the phenylenemethyl group is bonded to the nitrogen atom in the imidazolidine ring in the formula I;

e is 0 and h is 1;

in any of its stereoisomeric forms or mixtures thereof in any ratios, or its physiologically tolerated salts.

5. A pharmaceutical preparation, comprising one or more compounds according to claim 1 and a pharmaceutically acceptable carrier.

* * * * *